(12) United States Patent
Kinoshita et al.

(10) Patent No.: US 9,371,452 B2
(45) Date of Patent: Jun. 21, 2016

(54) FILM-FORMING MATERIAL, GROUP IV METAL OXIDE FILM AND VINYLENEDIAMIDE COMPLEX

(75) Inventors: Tomoyuki Kinoshita, Kanagawa (JP); Kohei Iwanaga, Kanagawa (JP); Sachio Asano, Kanagawa (JP); Takahiro Kawabata, Kanagawa (JP); Noriaki Oshima, Kanagawa (JP); Satori Hirai, Kanagawa (JP); Yoshinori Harada, Kanagawa (JP); Kazuyoshi Arai, Kanagawa (JP); Ken-ichi Tada, Kanagawa (JP)

(73) Assignees: TOSOH CORPORATION, Shunan-shi (JP); Sagami Chemical Research Institute, Ayase-shi (JP)

( * ) Notice: Subject to any disclaimer, the term of this patent is extended or adjusted under 35 U.S.C. 154(b) by 0 days.

(21) Appl. No.: 14/342,993

(22) PCT Filed: Sep. 3, 2012

(86) PCT No.: PCT/JP2012/072372
§ 371 (c)(1),
(2), (4) Date: Mar. 5, 2014

(87) PCT Pub. No.: WO2013/035672
PCT Pub. Date: Mar. 14, 2013

(65) Prior Publication Data
US 2014/0227456 A1    Aug. 14, 2014

(30) Foreign Application Priority Data

| Sep. 5, 2011 | (JP) | 2011-192739 |
| Sep. 5, 2011 | (JP) | 2011-192740 |
| Sep. 30, 2011 | (JP) | 2011-218284 |
| Feb. 9, 2012 | (JP) | 2012-026203 |
| Mar. 15, 2012 | (JP) | 2012-058232 |

(51) Int. Cl.
| C07F 7/02 | (2006.01) |
| G21H 5/00 | (2006.01) |
| C09D 1/00 | (2006.01) |
| C01B 33/113 | (2006.01) |
| C07F 7/00 | (2006.01) |
| H01L 21/02 | (2006.01) |

(52) U.S. Cl.
CPC ............... *C09D 1/00* (2013.01); *C01B 33/113* (2013.01); *C07F 7/006* (2013.01); *C07F 7/025* (2013.01); *H01L 21/02164* (2013.01); *H01L 21/02181* (2013.01); *H01L 21/02186* (2013.01); *H01L 21/02189* (2013.01); *H01L 21/02216* (2013.01); *H01L 21/02282* (2013.01)

(58) Field of Classification Search
CPC .......................................................... C09D 1/00
USPC .......................................... 556/410; 427/553
See application file for complete search history.

(56) References Cited

U.S. PATENT DOCUMENTS

| 6,337,301 B1 * | 1/2002 | Ohmori | B01J 21/063 |
| | | | 106/286.4 |
| 2009/0036697 A1 | 2/2009 | Tada et al. | |
| 2011/0011771 A1 | 1/2011 | Litz et al. | |
| 2011/0031164 A1 | 2/2011 | Litz et al. | |
| 2011/0108464 A1 | 5/2011 | Rankin et al. | |
| 2011/0119988 A1 | 5/2011 | Litz et al. | |
| 2012/0029220 A1 | 2/2012 | Tada et al. | |
| 2012/0067777 A1 | 3/2012 | Litz et al. | |
| 2012/0285864 A1 | 11/2012 | Rankin et al. | |
| 2012/0285866 A1 | 11/2012 | Litz et al. | |
| 2013/0048543 A1 | 2/2013 | Litz et al. | |
| 2013/0130892 A1 | 5/2013 | Litz et al. | |
| 2014/0131256 A1 | 5/2014 | Litz et al. | |
| 2014/0216984 A1 | 8/2014 | Litz et al. | |
| 2014/0291199 A1 | 10/2014 | Litz et al. | |
| 2014/0339136 A1 | 11/2014 | Litz et al. | |

FOREIGN PATENT DOCUMENTS

| CN | 101304964 A | 11/2008 |
| CN | 101815720 A | 8/2010 |
| CN | 102066313 A | 5/2011 |
| GB | 2 422 832 A | 8/2006 |
| JP | 2005 307218 | 11/2005 |
| JP | 2007 153872 | 6/2007 |
| JP | 2010 30986 | 2/2010 |

(Continued)

OTHER PUBLICATIONS

QPIDS NPL—Taiwan ISR.*
Steunou, N. et al., "Titanium OXO-Organo Clusters: Precursors for the Preparation of Nanostructured Titanium Oxide Based Materials", Ceramic Transactions, vol. 123, pp. 47-71, ISSN: 1042-1122, (May 2001).
Steunou, N. et al., "Ketones as an oxolation source for the synthesis of titanium-oxo-organo clusters", New J. Chem., vol. 23. No. 11, pp. 1079-1086,(Jan. 1999).
Day, V.W. et al., "Dodecatitanates: A New Family of Stable Polyoxotitanates", J. Am. Chem. Soc., vol. 115, No. 18, pp. 8469-8470, (Sep. 1993).

(Continued)

*Primary Examiner* — Porfirio Nazario Gonzalez
*Assistant Examiner* — Kofi Adzamli
(74) *Attorney, Agent, or Firm* — Oblon, McClelland, Maier & Neustadt, L.L.P.

(57) ABSTRACT

An object of the present invention is to provide a method for producing a Group IV metal oxide film useful as a semiconductor element or an optical element at a low temperature. The present invention relates to a method for producing a Group IV metal oxide film, comprising coating a surface of a substrate with a film-forming material dissolved in an organic solvent, and subjecting the substrate to a heat treatment, an ultraviolet irradiation treatment, or both of these treatments, wherein a film-forming material obtained by reacting a vinylenediamide complex having a specific structure with an oxidizing agent such as oxygen gas, air, ozone, water and hydrogen peroxide is used as the film-forming material.

3 Claims, 3 Drawing Sheets

(56) References Cited

FOREIGN PATENT DOCUMENTS

| JP | 2010 265257 | 11/2010 |
|---|---|---|
| JP | 4633628 | 11/2010 |
| JP | 2011-88851 A | 5/2011 |
| TW | 201000492 (A) | 1/2010 |
| TW | 201036985 (A) | 10/2010 |
| WO | 2005 012215 | 2/2005 |
| WO | WO 2009/012341 A2 | 1/2009 |
| WO | WO 2009/013721 A1 | 1/2009 |
| WO | WO 2010/119827 A1 | 10/2010 |

OTHER PUBLICATIONS

Evans, W. J. et al., "Isolation and structural characterization of the polymetallic zirconium alkoxide complexes", vol. 17, No. 5-6, pp. 869-877, 00289-1, (1998).

Dieck, H.T. et al., "Diazadiene complexes of Group 4 metals. I. Synthesis of momo-, bis- and tris(diazadiene) titanium complexes and the structure of diazadienedichlorotitanium", Inorganica Chimica Acta, vol. 177, No. 2, pp. 191-197, (Nov. 1990).

Katz, H. E. et al. "Titanium Cluster Polymers as Reactive Ion Etch Barriers", Chem. Mater., vol. 7 No. 8 pp. 1534-1538, (Aug. 1995).

Cotton, S. A., "Titanium, zirconium and hafnium", Annu. Rep. Prog. Chem., Sect. A, vol. 104, pp. 145-154, (2008).

Naka, A., et al., "Free Radical Reactions of Stable Silylenes and Germylenes", Organometallics, vol. 23, pp. 6330-6332, (2004).

International Search Report Issued Dec. 4, 2012 in PCT/JP12/072372 filed Sep. 3, 2012.

Combined Chinese Office Action and Search Report issued Feb. 13, 2015 in Patent Application No. 201280054346.9 (with English language translation and English Translation of Category of Cited Documents).

Partial Supplementary European Search Report issued Mar. 6, 2015 in Patent Application No. 12830501.8.

Evans, W. J. et al., "Isolation and structural characterization of the polymetallic zirconium alkoxide complexes", *Polyhedron*, vol. 17, No. 5-6, pp. 869-877, 00289-1, (1998).

Renee Papiernik, et al, "Synthesis and characterization of new titanium hexanuclear oxo carboxylato alkoxides. Molecular structure of [Ti6(u3-O)6-(u-O2CC6H4OPh)6(OEt)6]", J. Chem. Soc., Dalton Trans., 1998, pp. 2285-2287.

Irma Karatchevtseva, et al, "Crystallization of TiO2 powders and thin films prepared from modified titanium alkoxide precursors", J. Am. Ceram. Soc., vol. 91, No. 6, 2008, pp. 2015-2023.

Par I. Laaziz, et al., "Structure de Ti6(CH3COO)8(OiPr)8O4", Acta Cryst., vol. C46, 1990, pp. 2332-2334 (with English Abstract).

Extended European Search Report issued Jul. 6, 2015 in Patent Application No. 12830501.8.

Ken-Ichi Tada, et al., "Diazasilacyclopentene derivative, and method for the preparation thereof" Chemical Abstracts Services, XP002736122, 2010, 12 Pages.

Taiwanese Office Action issued on Dec. 22, 2015 in the corresponding Taiwanese Patent Aplication No. 101132361 with English translation.

\* cited by examiner

US 9,371,452 B2

FILM-FORMING MATERIAL, GROUP IV METAL OXIDE FILM AND VINYLENEDIAMIDE COMPLEX

TECHNICAL FIELD

The present invention relates to a film-forming material such as silicon oxide, titanium oxide, zirconium oxide and hafnium oxide which are used as a semiconductor element, optical element and the like, a vinylenediamide complex useful as a raw material for the formation of a Group IV metal oxide film and an oxide film, and a production method thereof.

BACKGROUND ART

The film of a Group IV metal oxide such as silicon oxide, titanium oxide, zirconium oxide and hafnium oxide shows various electrical properties such as relative permittivity and electrical resistivity, or various optical properties such as light transmittance and refractive index, based on difference in the composition, crystal structure or the like. Therefore, the Group IV metal oxide film is used as a semiconductor element, an optical element or the like in many devices and is expected to hereafter more extend its industrial usefulness. The technique for producing the Group IV metal oxide film is roughly classified into two methods, that is, dry method and wet method. The dry method includes a sputtering method, ion plating, a vapor deposition method, a CVD method, and the like, and these film-forming methods generally require a large vacuum apparatus. The wet method includes a sol-gel method, a metal organic deposition method (Metal Organic Deposition; MOD method), and the like. In the case of forming a Group IV metal oxide film by the wet method, the quality of the obtained Group IV metal oxide film is greatly affected by the kind of film-forming material and the film-forming temperature. Non-Patent Document 1 discloses $Si(^tBuNCH=CHN^tBu)(O^tBu)_2$ having a tert-butoxy group and a synthesis method therefor but is completely silent on using the silicon compound as a material for producing a silicon-containing thin film. Patent Document 1 discloses a diazasilacyclopentene derivative containing an unsubstituted alkyloxy group having a carbon number of 1 to 3, a synthesis method therefor, and a method for producing a silicon oxide thin film by CVD method using the derivative as a material. However, there is absolutely no description stating that a film-forming material suitable for the film forming process by wet method is obtained by reacting the diazasilacyclopentene derivative with an oxidizing agent. Patent Document 2 discloses a titanium complex having a diazatitanacyclopentene skeleton containing an alkyloxy group having a carbon number of 1 to 16, which may be substituted with a fluorine atom, a production method therefor, and a method for producing a titanium oxide thin film by CVD method using the complex as a material. However, there is absolutely no description stating that a film-forming material suitable for the film formation by wet method is obtained by reacting the titanium complex with an oxidizing agent.

In addition, Non-Patent Documents 2, 3 and 4 describe a titanium compound crosslinked by a titanium atom-containing bridging oxygen atom. However, Non-Patent Documents 2 and 3 are completely silent on using the titanium compound as a film-forming material solution or as to a Group IV metal oxide film.

Patent Document 3 describes a solution of a titanium compound crosslinked by a titanium atom-containing bridging oxygen atom, and an oxide film formed of the solution. The oxide film described in Patent Document 3 is an oxide film formed from a sol solution.

Non-Patent Document 5 describes a zirconium compound crosslinked by a zirconium atom-containing bridging oxygen atom. However, Non-Patent Document 5 is completely silent on using the zirconium compound as a film-forming material or as to a Group IV metal oxide film.

BACKGROUND ART DOCUMENT

Patent Document

Patent Document 1: JP-A-2010-265257 (the term "JP-A" as used herein means an "unexamined published Japanese patent application")
Patent Document 2: JP-A-2010-30986
Patent Document 3: Japanese Patent No. 4633628

Non-Patent Document

Non-Patent Document 1: Organometallics, Vol. 23, page 6330 (2004)
Non-Patent Document 2: Journal of the American Chemical Society, Vol. 115, page 8469 (1993)
Non-Patent Document 3: New Journal of Chemistry, Vol. 23, page 1079 (1999)
Non-Patent Document 4: Sol-Gel Commercialization and Applications: Proceedings of the Symposium at the 102nd Annual Meeting of The American Ceramic Society, held May 1-2, 2000, in St. Louis, Mo., Ceramic Transactions, Volume 123, page 49 (2001).
Non-Patent Document 5: polyhedron, Vol. 17, page 869 (1998)

SUMMARY OF INVENTION

Problem that Invention is to Solve

The sol-gel method suffers from disadvantages such as bad reproducibility and large surface roughness of the produced Group IV metal oxide film and in addition, disadvantageously requires a high film-forming temperature. Also, in conventional MOD methods, an alkoxo complex incapable of decomposing in the air at room temperature has been used as a material for the production of a Group IV metal oxide film, but in order to unfailingly achieve thermal decomposition of the complex and thereby produce a highly useful Group IV metal oxide film, a high film-forming temperature is required. But, in the case of producing a semiconductor element or an optical element, a plurality of different metal oxide films are generally stacked, and a thin film must be produced at a temperature as low as possible for preventing a trouble such as interdiffusion and separation between respective layers, as a result, the substrate temperature during film formation is preferably lower. Furthermore, it is recently requested to establish a technique for producing a metal oxide film on the surface of a thermally weak resin substrate or the like. That is, a production method for a Group IV metal oxide, and a Group IV metal oxide film-forming material, ensuring that a Group IV metal oxide film useful as a semiconductor element or an optical element can be produced at a temperature as low as possible, are demanded.

In addition, development of a complex working out to a synthesis raw material for producing an oxide film-forming material satisfying this requirement is demanded.

Means for Solving Problem

As a result of intensive studies to solve these problems, the present inventors have found a film-forming material obtained by reacting a vinylenediamide complex with an oxidizing agent, a film-forming material obtained by ligand exchange of a metal-oxygen bond-containing compound with a specific alcohol, a Group IV metal oxide film obtained using such a film-forming material, and a vinylenediamide complex useful as a film-forming material, and have accomplished the present invention.

That is, the present invention relates to a film-forming material, obtained by reacting a vinylenediamide complex represented by formula (1):

[Chem. 1]

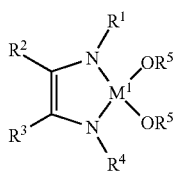

(1)

(wherein $M^1$ represents a titanium atom, a silicon atom, a zirconium atom or a hafnium atom; each of $R^1$ and $R^4$ independently represents an alkyl group having a carbon number of 3 to 12; each of $R^2$ and $R^3$ independently represents a hydrogen atom or an alkyl group having a carbon number of 1 to 4; and $R^5$ represents an alkyl group having a carbon number of 1 to 12, which may be substituted with a fluorine atom) with one or more kinds of oxidizing agents selected from the group consisting of oxygen gas, air, ozone, water and hydrogen peroxide;

a film-forming material, produced by reacting a vinylenediamide complex represented by formula (2):

[Chem. 2]

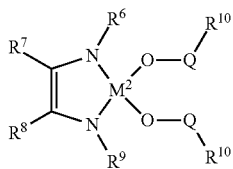

(2)

(wherein $M^2$ represents a titanium atom or a silicon atom; each of $R^6$ and $R^9$ independently represents a $C_1$-$C_{12}$ alkyl group; each of $R^7$ and $R^8$ independently represents a hydrogen atom or a $C_1$-$C_4$ alkyl group; $R^{10}$ represents a $C_1$-$C_6$ alkoxy group or a di($C_1$-$C_6$ alkyl)amino group; and Q represents a $C_2$-$C_6$ methylene group which may be substituted with a $C_1$-$C_3$ alkyl group) with one or more kinds of oxidizing agents selected from the group consisting of oxygen gas, air, ozone, water and hydrogen peroxide; and a Group IV metal oxide film produced using such a film-forming material.

Furthermore, the present invention relates to a vinylenediamide complex represented by formula (2) and a vinylenediamide complex represented by the following formula (7), which are useful for the film-forming material:

[Chem. 3]

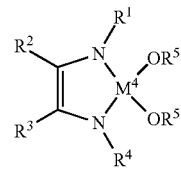

(7)

(wherein $M^4$ represents a zirconium atom or a hafnium atom; $R^1$ to $R^4$ have the same meanings as $R^1$ to $R^4$ in formula (1); and $R^5$ has the same meaning as $R^5$ in formula (1) or $QR^{10}$ in formula (2)).

That is, the gist of the present invention resides in the following <1> to <21>.

<1> A film-forming material, obtained by reacting a vinylenediamide complex represented by formula (1):

[Chem. 4]

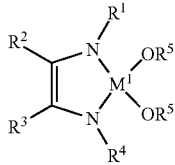

(1)

(wherein $M^1$ represents a titanium atom, a silicon atom, a zirconium atom or a hafnium atom; each of $R^1$ and $R^4$ independently represents an alkyl group having a carbon number of 3 to 12; each of $R^2$ and $R^3$ independently represents a hydrogen atom or an alkyl group having a carbon number of 1 to 4; and $R^5$ represents an alkyl group having a carbon number of 1 to 12, which may be substituted with a fluorine atom) with one or more kinds of oxidizing agents selected from the group consisting of oxygen gas, air, ozone, water and hydrogen peroxide.

<2> The film-forming material as described in <1> above, wherein in formula (1), $M^1$ is preferably a titanium atom, a zirconium atom or a hafnium atom.

<3> A film-forming material, produced by reacting a vinylenediamide complex represented by formula (2):

[Chem. 5]

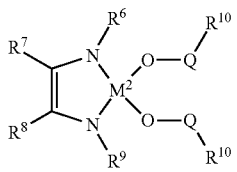

(2)

(wherein $M^2$ represents a titanium atom or a silicon atom; each of $R^6$ and $R^9$ independently represents a $C_1$-$C_{12}$ alkyl group; each of $R^7$ and $R^8$ independently represents a hydrogen atom or a $C_1$-$C_4$ alkyl group; $R^{10}$ represents a $C_1$-$C_6$ alkoxy group or a di($C_1$-$C_6$ alkyl)amino group; and Q represents a $C_2$-$C_6$ methylene group which may be substituted with a $C_1$-$C_3$ alkyl group) with one or more kinds of oxidizing agents selected from the group consisting of oxygen gas, air, ozone, water and hydrogen peroxide.

<4> The film-forming material as described in any one of <1> to <3> above,
wherein the film-forming material is preferably a film-forming material obtained by dissolving a reaction product in an alcohol containing two or more oxygen atoms in a molecule and thereafter, heating a solution.

<5> The film-forming material according to <4> above,
wherein the alcohol is preferably cellosolves.

<6> The film-forming material according to <5> above,
wherein the cellosolves is preferably ethylene glycol monomethyl ether.

<7> A film-forming material, obtained by dissolving a compound having a titanium atom or a zirconium atom, with said metal atoms being bridged by a bridging oxygen atom, in an alcohol containing two or more oxygen atoms in a molecule and thereafter, heating a solution.

<8> The film-forming material as described in <7> above,
wherein the alcohol is preferably cellosolves.

<9> The film-forming material as described in <8> above,
wherein the cellosolves is preferably ethylene glycol monomethyl ether.

<10> A film-forming material solution, comprising:
the film-forming material described in any one of <1> to <9> above and an organic solvent.

<11> The film-forming material solution as described in <10> above,
wherein the organic solvent is preferably alcohols.

<12> The film-forming material solution as described in <11> above,
wherein the alcohols is preferably ethylene glycol monomethyl ether.

<13> A method for producing a Group IV metal oxide film, comprising:
coating the film-forming material solution described in any one of <10> to <12> above on a surface of a substrate; and
subjecting the substrate to a heat treatment, an ultraviolet irradiation treatment, or both of the treatments.

<14> A vinylenediamide complex represented by formula (2):

[Chem. 6]

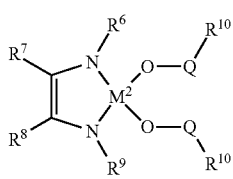

(2)

(wherein $M^2$ represents a titanium atom or a silicon atom; each of $R^6$ and $R^9$ independently represents a $C_3$-$C_{12}$ alkyl group; each of $R^7$ and $R^8$ independently represents a hydrogen atom or a $C_1$-$C_4$ alkyl group; $R^{10}$ represents a $C_1$-$C_6$ alkoxy group or a di($C_1$-$C_6$ alkyl)amino group; and Q represents a $C_2$-$C_6$ methylene group which may be substituted with a $C_1$-$C_3$ alkyl group).

<15> The vinylenediamide complex as described in <14> above,
wherein, preferably, $M^2$ is a titanium atom or a silicon atom; each of $R^6$ and $R^9$ is independently an isopropyl group, a tert-butyl group or a tert-pentyl group; each of $R^7$ and $R^8$ is a hydrogen atom; Q is an ethane-1,2-diyl group or a propane-1,3-diyl group, which may be substituted with a methyl group or an ethyl group; and $R^{10}$ is a $C_1$-$C_4$ alkoxy group, a dimethylamino group or a diethylamino group.

<16> A method for producing the vinylenediamide complex of <14> above, comprising preferably:
reacting a tetraalkoxide represented by formula (3):

$$M^2(OQR^{10})_4 \qquad (3)$$

(wherein $M^2$, Q and $R^{10}$ have the same meanings as $M^2$, Q and $R^{10}$ in formula (2)) with a vinylenediamide alkali metal salt represented by formula (4):

[Chem. 7]

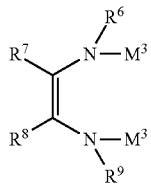

(4)

(wherein $R^6$ to $R^9$ have the same meanings as $R^6$ to $R^9$ in formula (2); and $M^3$ represents an alkali metal atom).

<17> A method for producing the vinylenediamide complex of <14> where $M^2$ in formula (2) is a titanium atom, comprising preferably:
reacting a bis(dialkylamide)titanium complex represented by formula (5):

[Chem. 8]

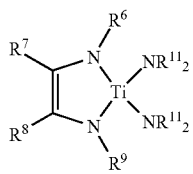

(5)

(wherein $R^6$ to $R^9$ have the same meanings as $R^6$ to $R^9$ in formula (2); and $R^{11}$ represents a $C_1$-$C_6$ alkyl group) with an alcohol represented by formula (6):

$$R^{10}QOH \qquad (6)$$

(wherein $R^{10}$ and Q have the same meanings as $R^{10}$ and Q in formula (2)).

<18> A vinylenediamide complex represented by formula (7):

[Chem. 9]

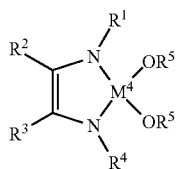

(7)

(wherein $M^4$ represents a zirconium atom or a hafnium atom; $R^1$ to $R^4$ have the same meanings as $R^1$ to $R^4$ in formula (1); and $R^5$ has the same meaning as $R^5$ in formula (1) or $QR^{10}$ in formula (2)).

<19> The vinylenediamide complex as described in <18> above,
wherein, preferably, $M^4$ is a zirconium atom or a hafnium atom; each of $R^1$ and $R^4$ is independently a tert-butyl group or a tert-pentyl group; each of $R^2$ and $R^3$ is a hydrogen atom; and $R^5$ is a tert-butyl group or a tert-pentyl group.

<20> A method for producing the vinylenediamide complex described in <18> above, comprising preferably:
reacting a metal tetraalkoxide represented by formula (8):

$$M^4(OR^5)_4 \quad (8)$$

(wherein $M^4$ and $R^5$ have the same meanings as $M^4$ and $R^5$ in formula (7)) with a metal tetrachloride represented by formula (9):

$$M^4Cl_4 \quad (9)$$

(wherein $M^4$ has the same meaning as $M^4$ in formula (7)) and a vinylenediamide alkali metal salt represented by formula (10):

[Chem. 10]

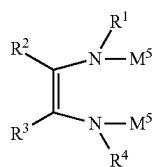

(10)

(wherein $R^1$ to $R^4$ have the same meanings as $R^1$ to $R^4$ in formula (7); and $M^5$ represents an alkali metal atom).

<21> A method for producing the vinylenediamide complex of <18> above where $M^4$ in formula (7) is a zirconium atom, comprising preferably:
reacting tetrachlorobis(tetrahydrofuran)zirconium with a vinylenediamide alkali metal salt represented by formula (10) and a metal alkoxide represented by formula (11):

$$M^6OR^5 \quad (11)$$

(wherein $R^5$ has the same meaning as $R^5$ in formula (7); and $M^6$ represents an alkali metal).

Effects of Invention

By virtue of using a film-forming material produced by reacting a vinylenediamide complex (1) or (2) with one or more kinds of oxidizing agents selected from the group consisting oxygen gas, air, ozone, water and hydrogen peroxide, a Group IV metal oxide film can be obtained even by heat treatment at a low temperature.

MODE FOR CARRYING OUT INVENTION

Figure 1:
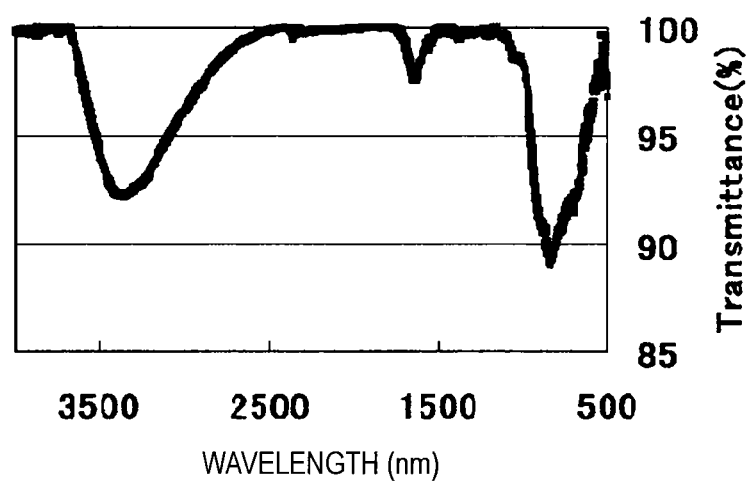
FIG. 1 is a graph showing the IR spectrum of a film.

The present invention is described in detail below.
In the description of the present invention, Group IV is employed as the notation for the periodic table of elements, but in recent years, Group 4 or Group 14 is often used as the notation for the periodic table of elements.
Titanium, zirconium, hafnium and the like belong to Group 4 of the periodic table of elements, and silicon and the like belong to Group 14 of the periodic table of elements.
The definitions of $R^1$, $R^2$, $R^3$, $R^4$ and $R^5$ in formula (1) of the film-forming material are described. The alkyl group having a carbon number of 3 to 12 represented by $R^1$ and $R^4$ may be any of linear, branched and cyclic alkyl groups. Specific examples thereof include a propyl group, an isopropyl group, a cyclopropyl group, a butyl group, a isobutyl group, a sec-butyl group, a tert-butyl group, a cyclobutyl group, a pentyl group, an isopentyl group, a neopentyl group, a tert-pentyl group, a 1-methylbutyl group, a 2-methylbutyl group, a 1,2-dimethylpropyl group, a 1-ethylpropyl group, a cyclopentyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclohexyl group, a cyclopropylmethyl group, a cyclopropylethyl group, a cyclobutylmethyl group, a heptyl group, a cyclohexylmethyl group, a 1,1-diethyl-propyl group, a 2-methylcyclohexyl group, a 4-methylcyclohexyl group, an octyl group, a 1,1-diethyl-2-methylpropyl group, a 2,5-dimethylcyclohexyl group, a 3,5-dimethylcyclohexyl group, a 1,1,3,3-tetramethylbutyl group, a 1-methyl-1-propylbutyl group, a 1,1,2,3,3-pentamethylbutyl group, a 1,1-diethyl-3,3-dimethylbutyl group, an adamantyl group, a 1,1-dimethyloctyl group, a 1,1-dipropylbutyl group, a 1,1-dimethyldecyl group, a 1,1-diethyloctyl group, and a 1-butyl-1-propylpentyl group.

From the standpoint that a Group IV metal oxide film improved in the electrical properties such as electrical conductivity or in the optical properties such as refractive index can be produced, each of $R^1$ and $R^4$ is independently, preferably an alkyl group having a carbon number of 3 to 8, more preferably a secondary or tertiary alkyl group having a carbon number of 3 to 5, still more preferably an isopropyl group, a tert-butyl group or a tert-pentyl group.

Each of $R^2$ and $R^3$ independently represents a hydrogen atom or an alkyl group having a carbon number of 1 to 4. The alkyl group having a carbon number of 1 to 4 may be any of linear, branched and cyclic alkyl groups, and examples thereof include a methyl group, an ethyl group, a propyl group, an isopropyl group, a cyclopropyl group, a butyl group, an isobutyl group, a sec-butyl group, a tert-butyl group, and a cyclobutyl group. From the standpoint that a Group IV metal oxide film improved in the electrical properties such as electrical conductivity or in the optical properties such as refractive index can be produced, each of $R^2$ and $R^3$ is preferably a hydrogen atom.

The alkyl group having a carbon number of 1 to 12 represented by $R^5$ may be any of linear, branched and cyclic alkyl groups, and examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, an isopentyl group, a neopentyl group, a tert-pentyl group, a 1-methylbutyl group, a 2-methylbutyl group, a 1,2-dimethylpropyl group, a 1-ethylpropyl group, a cyclopentyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclohexyl group, a cyclopropylmethyl group, a cyclopropylethyl group, a cyclobutylmethyl group, a heptyl group, a cyclohexylmethyl group, a 1,1-diethyl-propyl group, a 2-methylcyclohexyl group, a 4-methylcyclohexyl group, an octyl group, a nonyl group, a decyl group, an undecyl group, a dodecyl group, a 1,1-diethyl-2-methylpropyl group, a 2,5-dimethylcyclohexyl group, a 3,5-dimethylcyclohexyl group, a 1,1,3,3-tetramethylbutyl group, a 1-methyl-1-propylbutyl group, a 1,1,2,3,3-pentamethylbutyl group, a 1,1-diethyl-3,3-dimethylbutyl group, an adamantyl group, a 1,1-dimethyloctyl group, a 1,1-dipropylbutyl group, a 1,1-dimethyldecyl group, a 1,1-diethyloctyl group, and a 1-butyl-1-propylpentyl group.

These may be substituted with a fluorine atom, and examples thereof include a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group, a perfluoroethyl group, a 1-fluoropropyl group, a 2-fluoropropyl group, a 3-fluoropropyl group, a 1,1-difluoropropyl group, a 2,2-difluoropropyl group, a 3,3-difluoropropyl group, a 3,3,3-trifluoropropyl group, a perfluoropropyl group, a 1-trifluoromethyl-2,2,2-trifluoroethyl group, a perfluoroisopropyl group, a perfluorobutyl group, a perfluoroisobutyl group, a perfluoro-sec-butyl group, a perfluoro-tert-butyl group, a perfluoropentyl group, a perfluoroisopentyl group, a perfluoroneopentyl group, a perfluoro-tert-pentyl group, a perfluorohexyl group, a perfluorocyclohexyl group, a perfluoroheptyl group, a perfluorooctyl group, a perfluorononyl group, a perfluorodecyl group, a perfluoroundecyl group, and a perfluorododecyl group.

From the standpoint that a Group IV metal oxide film improved in the electrical properties such as electrical conductivity or in the optical properties such as refractive index can be produced, when $M^1$ in formula (1) is a titanium atom or a silicon atom, $R^5$ is more preferably a non-fluorine-substituted alkyl group having a carbon number of 1 to 4, still more preferably a methyl group, an ethyl group, a propyl group or an isopropyl group.

From the standpoint that a Group IV metal oxide film improved in the electrical properties such as electrical conductivity or in the optical properties such as refractive index can be produced, when $M^1$ in formula (1) is a zirconium atom or a hafnium atom, $R^5$ is more preferably a non-fluorine-substituted alkyl group having a carbon number of 4 to 7, still more preferably a tert-butyl group or a tert-pentyl group.

In formula (1), $M^1$ represents a titanium atom, a silicon atom, a zirconium atom or a hafnium atom, and among others, is preferably a titanium atom or a zirconium atom.

Specific examples of the vinylenediamide complex represented by formula (1) include (N,N'-diisopropyl-1,2-vinylenediamide-$\kappa^2$N,N')dimethoxytitanium (Ti($^i$PrNCH=CHN$^i$Pr)(OMe)$_2$), (N,N'-di-tert-butyl-1,2-vinylenediamide-$\kappa^2$N,N')dimethoxytitanium(Ti($^t$BuNCH=CHN$^t$Bu)(OMe)$_2$), (N,N'-di-tert-pentyl-1,2-vinylenediamide-$\kappa^2$N,N')dimethoxytitanium(Ti($^t$PeNCH=CHN$^t$Pe)(OMe)$_2$), (N,N'-bis(1,1,3,3-tetramethylbutyl)-1,2-vinylenediamide-$\kappa^2$N,N'-dimethoxytitanium(Ti($^t$OctNCH=CHN$^t$Oct)(OMe)$_2$), (N,N'-diisopropyl-1,2-vinylenediamide-$\kappa^2$N,N')diethoxytitanium(Ti($^i$PrNCH=CHN$^i$Pr)(OEt)$_2$), (N,N'-di-tert-butyl-1,2-vinylenediamide-$\kappa^2$N,N')diethoxytitanium(Ti($^t$BuNCH=CHN$^t$Bu)(OEt)$_2$), (N,N'-di-tert-pentyl-1,2-vinylenediamide-$\kappa^2$N,N')diethoxytitanium(Ti($^t$PeNCH=CHN$^t$Pe)(OEt)$_2$), (N,N'-bis(1,1,3,3-tetramethylbutyl)-1,2-vinylenediamide-$\kappa^2$N,N')diethoxytitanium(Ti($^t$OctNCH=CHN$^t$Oct)(OEt)$_2$), (N,N'-diisopropyl-1,2-vinylenediamide-$\kappa^2$N,N')dipropoxytitanium(Ti($^i$PrNCH=CHN$^i$Pr)(OPr)$_2$), (N,N'-di-tert-butyl-1,2-vinylenediamide-$\kappa^2$N,N')dipropoxytitanium (Ti($^t$BuNCH=CHN$^t$Bu)(OPr)$_2$), (N,N'-di-tert-pentyl-1,2-vinylenediamide-$\kappa^2$N,N')dipropoxytitanium(Ti($^t$PeNCH=CHN$^t$Pe)(OPr)$_2$), (N,N'-bis(1,1,3,3-tetramethylbutyl)-1,2-vinylenediamide-$\kappa^2$N,N')dipropoxytitanium(Ti($^t$OctNCH=CHN$^t$Oct)(OPr)$_2$), (N,N'-diisopropyl-1,2-vinylenediamide-$\kappa^2$N,N')diisopropoxytitanium(Ti($^i$PrNCH=CHN$^i$Pr)(O$^i$Pr)$_2$), (N,N'-di-tert-butyl-1,2-vinylenediamide-$\kappa^2$N,N')diisopropoxytitanium(Ti($^t$BuNCH=CHN$^t$Bu)(O$^i$Pr)$_2$), (N,N'-di-tert-pentyl-1,2-vinylenediamide-$\kappa^2$N,N')diisopropoxytitanium(Ti($^t$PeNCH=CHN$^t$Bu)(O$^i$Pr)$_2$), (N,N'-bis(1,1,3,3-tetramethylbutyl)-1,2-vinylenediamide-$\kappa^2$N,N') diisopropoxytitanium(Ti($^t$OctNCH=CHN$^t$Oct)(O$^i$Pr)$_2$), (N,N'-diisopropyl-1,2-vinylenediamide-$\kappa^2$N,N')di-sec-butoxytitanium(Ti($^i$PrNCH=CHN$^i$Pr)(O$^s$Bu)$_2$), (N,N'-di-tert-butyl-1,2-vinylenediamide-$\kappa^2$N,N')di-sec-butoxytitanium(Ti($^t$BuNCH=CHN$^t$Bu)(O$^s$Bu)$_2$), (N,N'-di-tert-pentyl-1,2-vinylenediamide-$\kappa^2$N,N')di-sec-butoxytitanium (Ti($^t$PeNCH=CHN$^t$Pe)(O$^s$Bu)$_2$), (N,N'-bis(1,1,3,3-tetramethylbutyl)-1,2-vinylenediamide-$\kappa^2$N,N')di-sec-butoxytitanium(Ti($^t$OctNCH=CHN$^t$Oct)(O$^s$Bu)$_2$), (N,N'-diisopropyl-1,2-vinylenediamide-$\kappa^2$N,N')di-tert-butoxytitanium(Ti($^i$PrNCH=CHN$^i$Pr)(O$^t$Bu)$_2$), (N,N'-di-tert-butyl-1,2-vinylenediamide-$\kappa^2$N,N')di-tert-butoxytitanium(Ti($^t$BuNCH=CHN$^t$Bu)(O$^t$Bu)$_2$), (N,N'-di-tert-pentyl-1,2-vinylenediamide-$\kappa^2$N,N')di-tert-butoxytitanium(Ti($^t$PeNCH=CHN$^t$Pe)(O$^t$Bu)$_2$), (N,N'-bis(1,1,3,3-tetramethylbutyl)-1,2-vinylenediamide-$\kappa^2$N,N')di-tert-butoxytitanium(Ti($^t$OctNCH=CHN$^t$Oct)(O$^t$Bu)$_2$), (N,N'-diisopropyl-1,2-vinylenediamide-$\kappa^2$N,N')di-tert-pentyloxytitanium(Ti($^i$PrNCH=CHN$^i$Pr)(O$^t$Pe)$_2$), (N,N'-di-tert-butyl-1,2-vinylenediamide-$\kappa^2$N,N')di-tert-pentyloxytitanium(Ti($^t$BuNCH=CHN$^t$Bu)(O$^t$Pe)$_2$), (N,N'-diisopropyl-1,2-vinylenediamide-$\kappa^2$N,N')bis(2,2,2-trifluoroethyloxy)titanium(Ti($^i$PrNCH=CHN$^i$Pr)(OCH$_2$CF$_3$)$_2$), (N,N'-di-tert-butyl-1,2-vinylenediamide-$\kappa^2$N,N')bis(2,2,2-trifluoroethyloxy)titanium(Ti($^t$BuNCH=CHN$^t$Bu)(OCH$_2$CF$_3$)$_2$), (N,N'-di-tert-pentyl-1,2-vinylenediamide-$\kappa^2$N,N')bis(2,2,2-trifluoroethyloxy)titanium(Ti($^t$PeNCH=CHN$^t$Pe)(OCH$_2$CF$_3$)$_2$), (N,N'-bis(1,1,3,3-tetramethylbutyl)-1,2-vinylenediamide-$\kappa^2$N,N')bis(2,2,2-trifluoroethyloxy)titanium(Ti($^t$OctNCH=CHN$^t$Oct)(OCH$_2$CF$_3$)$_2$), (N,N'-diisopropyl-1,2-vinylenediamide-$\kappa^2$N,N')bis(1,1,1-trifluoropropan-2-yloxy)titanium(Ti($^i$PrNCH=CHN$^i$Pr)(OCH(CF$_3$)Me)$_2$), (N,N'-di-tert-butyl-1,2-vinylenediamide-$\kappa^2$N,N')bis(1,1,1-trifluoropropan-2-yloxy)titanium(Ti($^t$BuNCH=CHN$^t$Bu)(OCH(CF$_3$)Me)$_2$), (N,N'-di-tert-pentyl-1,2-vinylenediamide-$\kappa^2$N,N')bis(1,1,1-trifluoropropan-2-yloxy)titanium(Ti($^t$PeNCH=CHN$^t$Pe)(OCH(CF$_3$)Me)$_2$), (N,N'-bis(1,1,3,3-tetramethylbutyl)-1,2-vinylenediamide-$\kappa^2$N,N')bis(1,1,1-trifluoropropan-2-yloxy)titanium(Ti($^t$OctNCH=CHN$^t$Oct)(OCH(CF$_3$)Me)$_2$), (N,N'-diisopropyl-1,2-vinylenediamide- κ$^2$N,N')bis(1,1,1,3,3,3-hexafluoropropan-2-yloxy)titanium(Ti($^i$PrNCH=CHN$^i$Pr)(OCH(CF$_3$)$_2$)$_2$), (N,N'-di-tert-butyl-1,2-vinylenediamide-κ$^2$N,N')bis(1,1,1,3,3,3-hexafluoropropan-2-yloxy)titanium(Ti($^t$BuNCH=CHN$^t$Bu)(OCH(CF$_3$)$_2$)$_2$), (N,N'-di-tert-pentyl-1,2-vinylenediamide-κ$^2$N,N')bis(1,1,1,3,3,3-hexafluoropropan-2-yloxy)titanium(Ti($^t$PeNCH=CHN$^t$Pe)(OCH(CF$_3$)$_2$)$_2$), (N,N'-bis(1,1,3,3-tetramethylbutyl)-1,2-vinylenediamide-κ$^2$N,N')bis(1,1,3,3,3-hexafluoropropan-2-yloxy)titanium(Ti($^t$OctNCH=CHN$^t$Oct)(OCH(CF$_3$)$_2$)$_2$), (N,N'-diisopropyl-1,2-vinylenediamide-κ$^2$N,N')bis(4,4,4-trifluorobutyloxy)titanium(Ti($^i$PrNCH=CHN$^i$Pr)(OCH$_2$CH$_2$CH$_2$CF$_3$)$_2$), (N,N'-di-tert-butyl-1,2-vinylenediamide-κ$^2$N,N')bis(4,4,4-trifluorobutyloxy)titanium(Ti($^t$BuNCH=CHN$^t$Bu)(OCH$_2$CH$_2$CH$_2$CF$_3$)$_2$), (N,N'-di-tert-pentyl-1,2-vinylenediamide-κ$^2$N,N')bis(4,4,4-trifluorobutyloxy)titanium(Ti($^t$PeNCH=CHN$^t$Pe)(OCH$_2$CH$_2$CH$_2$CF$_3$)$_2$), (N,N'-bis(1,1,3,3-tetramethylbutyl)-1,2-vinylenediamide-κ$^2$N,N')bis(4,4,4-trifluorobutyloxy)titanium(Ti($^t$OctNCH=CHN$^t$Oct)(OCH$_2$CH$_2$CH$_2$CF$_3$)$_2$), (N,N'-di-tert-pentyl-1,2-vinylenediamide-κ$^2$N,N')di-tert-pentyloxytitanium(Ti($^t$PeNCH=CHN$^t$Pe)(O$^t$Pe)$_2$), (N,N'-bis(1,1,3,3-tetramethylbutyl)-1,2-vinylenediamide-κ$^2$N,N')di-tert-pentyloxytitanium(Ti($^t$OctNCH=CHN$^t$Oct)(O$^t$Pe)$_2$), (N,N'-diisopropyl-1,2-vinylenediamide-κ$^2$N,N')dimethoxysilane(Si($^i$PrNCH=CHN$^i$Pr)(OMe)$_2$), (N,N'-di-tert-butyl-1,2-vinylenediamide-κ$^2$N,N')dimethoxysilane(Si($^t$BuNCH=CHN$^t$Bu)(OMe)$_2$), (N,N'-di-tert-pentyl-1,2-vinylenediamide-κ$^2$N,N')dimethoxysilane(Si($^t$PeNCH=CHN$^t$Pe)(OMe)$_2$), (N,N'-bis(1,1,3,3-tetramethylbutyl)-1,2-vinylenediamide-κ$^2$N,N')dimethoxysilane(Si($^t$OctNCH=CHN$^t$Oct)(OMe)$_2$), (N,N'-diisopropyl-1,2-vinylenediamide-κ$^2$N,N')diethoxysilane(Si($^i$PrNCH=CHN$^i$Pr)(OEt)$_2$), (N,N'-di-tert-butyl-1,2-vinylenediamide-κ$^2$N,N')diethoxysilane(Si($^t$BuNCH=CHN$^t$Bu)(OEt)$_2$), (N,N'-di-tert-pentyl-1,2-vinylenediamide-κ$^2$N,N')diethoxysilane(Si($^t$PeNCH=CHN$^t$Pe)(OEt)$_2$), tetramethylbutyl)-1,2-vinylenediamide-κ$^2$N,N')diethoxysilane(Si($^t$OctNCH=CHN$^t$Oct)(OEt)$_2$), (N,N'-diisopropyl-1,2-vinylenediamide-κ$^2$N,N')dipropoxysilane(Si($^i$PrNCH=CHN$^i$Pr)(OPr)$_2$), (N,N'-di-tert-butyl-1,2-vinylenediamide-κ$^2$N,N')dipropoxysilane(Si($^t$BuNCH=CHN$^t$Bu)(OPr)$_2$), (N,N'-di-tert-pentyl-1,2-vinylenediamide-κ$^2$N,N')dipropoxysilane(Si($^t$PeNCH=CHN$^t$Pe)(OPr)$_2$), (N,N'-bis(1,1,3,3-tetramethylbutyl)-1,2-vinylenediamide-κ$^2$N,N')dipropoxysilane(Si($^t$OctNCH=CHN$^t$Oct)(OPr)$_2$), (N,N'-diisopropyl-1,2-vinylenediamide-κ$^2$N,N')diisopropoxysilane(Si($^i$PrNCH=CHN$^i$Pr)(O$^i$Pr)$_2$), (N,N'-di-tert-butyl-1,2-vinylenediamide-κ$^2$N,N')diisopropoxysilane(Si($^t$BuNCH=CHN$^t$Bu)(O$^i$Pr)$_2$), (N,N'-di-tert-pentyl-1,2-vinylenediamide-κ$^2$N,N')diisopropoxysilane(Si($^t$PeNCH=CHN$^t$Pe)(O$^i$Pr)$_2$), (N,N'-bis(1,1,3,3-tetramethylbutyl)-1,2-vinylenediamide-κ$^2$N,N')diisopropoxysilane(Si($^t$OctNCH=CHN$^t$Oct)(O$^i$Pr)$_2$), (N,N'-diisopropyl-1,2-vinylenediamide-κ$^2$N,N')di-sec-butoxysilane(Si($^i$PrNCH=CHN$^i$Pr)(O$^s$Bu)$_2$), (N,N'-di-tert-butyl-1,2-vinylenediamide-κ$^2$N,N')di-sec-butoxysilane(Si($^t$BuNCH=CHN$^t$Bu)(O$^s$Bu)$_2$), (N,N'-di-tert-pentyl-1,2-vinylenediamide-κ$^2$N,N')di-sec-butoxysilane(Si($^t$PeNCH=CHN$^t$Pe)(O$^s$Bu)$_2$), (N,N'-bis(1,1,3,3-tetramethylbutyl)-1,2-vinylenediamide-κ$^2$N,N')di-sec-butoxysilane(Si($^t$OctNCH=CHN$^t$Oct)(O$^s$Bu)$_2$), (N,N'-diisopropyl-1,2-vinylenediamide-κ$^2$N,N')di-tert-butoxysilane(Si($^i$PrNCH=CHN$^i$Pr)(O$^t$Bu)$_2$), (N,N'-di-tert-butyl-1,2-vinylenediamide-κ$^2$N,N')di-tert-butoxysilane(Si($^t$BuNCH=CHN$^t$Bu)(O$^t$Bu)$_2$), (N,N'-di-tert-pentyl-1,2-vinylenediamide-κ$^2$N,N')di-tert-butoxysilane(Si($^t$PeNCH=CHN$^t$Pe)(O$^t$Bu)$_2$), (N,N'-bis(1,1,3,3-tetramethylbutyl)-1,2-vinylenediamide-κ$^2$N,N')di-tert-butoxysilane(Si($^t$OctNCH=CHN$^t$Oct)(O$^t$Bu)$_2$), (N,N'-diisopropyl-1,2-vinylenediamide-κ$^2$N,N')di-tert-pentyloxysilane(Si($^i$PrNCH=CHN$^i$Pr)(O$^t$Pe)$_2$), (N,N'-di-tert-butyl-1,2-vinylenediamide-κ$^2$N,N')di-tert-pentyloxysilane(Si($^t$BuNCH=CHN$^t$Bu)(O$^t$Pe)$_2$), (N,N'-di-tert-pentyl-1,2-vinylenediamide-κ$^2$N,N')di-tert-pentyloxysilane(Si($^t$PeNCH=CHN$^t$Pe)(O$^t$Pe)$_2$), (N,N'-bis(1,1,3,3-tetramethylbutyl)-1,2-vinylenediamide-κ$^2$N,N')di-tert-pentyloxysilane(Si($^t$OctNCH=CHN$^t$Oct)(O$^t$Pe)$_2$), (N,N'-diisopropyl-1,2-vinylenediamide-κ$^2$N,N')bis(2,2,2-trifluoroethyloxy)silane(Si($^i$PrNCH=CHN$^i$Pr)(OCH$_2$CF$_3$)$_2$), (N,N'-di-tert-butyl-1,2-vinylenediamide-κ$^2$N,N')bis(2,2,2-trifluoroethyloxy)silane(Si($^t$BuNCH=CHN$^t$Bu)(OCH$_2$CF$_3$)$_2$), (N,N'-di-tert-pentyl-1,2-vinylenediamide-κ$^2$N,N')bis(2,2,2-trifluoroethyloxy)silane(Si($^t$PeNCH=CHN$^t$Pe)(OCH$_2$CF$_3$)$_2$), (N,N'-bis(1,1,3,3-tetramethylbutyl)-1,2-vinylenediamide-κ$^2$N,N')bis(2,2,2-trifluoroethyloxy)silane(Si($^t$OctNCH=CHN$^t$Oct)(OCH$_2$CF$_3$)$_2$), (N,N'-diisopropyl-1,2-vinylenediamide-κ$^2$N,N')bis(1,1,1-trifluoropropan-2-yloxy)silane(Si($^i$PrNCH=CHN$^i$Pr)(OCH(CF$_3$)Me)$_2$), (N,N'-di-tert-butyl-1,2-vinylenediamide-κ$^2$N,N')bis(1,1,1-trifluoropropan-2-yloxy)silane(Si($^t$BuNCH=CHN$^t$Bu)(OCH(CF$_3$)Me)$_2$), (N,N'-di-tert-pentyl-1,2-vinylenediamide-κ$^2$N,N')bis(1,1,1-trifluoropropan-2-yloxy)silane(Si($^t$PeNCH=CHN$^t$Pe)(OCH(CF$_3$)Me)$_2$), (N,N'-bis(1,1,3,3-tetramethylbutyl)-1,2-vinylenediamide-κ$^2$N,N')bis(1,1,1-trifluoropropan-2-yloxy)silane(Si($^t$OctNCH=CHN$^t$Oct)(OCH(CF$_3$)Me)$_2$), (N,N'-diisopropyl-1,2-vinylenediamide-κ$^2$N,N')bis(1,1,1,3,3,3-hexafluoropropan-2-yloxy)silane(Si($^i$PrNCH=CHN$^i$Pr)(OCH(CF$_3$)$_2$)$_2$), (N,N'-di-tert-butyl-1,2-vinylenediamide-κ$^2$N,N')bis(1,1,1,3,3,3-hexafluoropropan-2-yloxy)silane(Si($^t$BuNCH=CHN$^t$Bu)(OCH(CF$_3$)$_2$)$_2$), (N,N'-di-tert-pentyl-1,2-vinylenediamide-κ$^2$N,N')bis(1,1,1,3,3,3-hexafluoropropan-2-yloxy)silane(Si($^t$PeNCH=CHN$^t$Pe)(OCH(CF$_3$)$_2$)$_2$), (N,N'-bis(1,1,3,3-tetramethylbutyl)-1,2-vinylenediamide-κ$^2$N,N')bis(1,1,1,3,3,3-hexafluoropropan-2-yloxy)silane(Si($^t$OctNCH=CHN$^t$Oct)(OCH(CF$_3$)$_2$)$_2$), (N,N'-diisopropyl-1,2-vinylenediamide-κ$^2$N,N')bis(4,4,4-trifluorobutyloxy)silane(Si($^i$PrNCH=CHN$^i$Pr)(OCH$_2$CH$_2$CH$_2$CF$_3$)$_2$), (N,N'-di-tert-butyl-1,2-vinylenediamide-κ$^2$N,N')bis(4,4,4-trifluorobutyloxy)silane(Si($^t$BuNCH=CHN$^t$Bu)(OCH$_2$CH$_2$CH$_2$CF$_3$)$_2$), (N,N'-di-tert-pentyl-1,2-vinylenediamide-κ$^2$N,N')bis(4,4,4-trifluorobutyloxy)silane(Si($^t$PeNCH=CHN$^t$Pe)(OCH$_2$CH$_2$CH$_2$CF$_3$)$_2$), (N,N'-bis(1,1,3,3-tetramethylbutyl)-1,2-vinylenediamide-κ$^2$N,N')bis(4,4,4-trifluorobutyloxy)silane(Si($^t$OctNCH=CHN$^t$Oct)(OCH$_2$CH$_2$CH$_2$CF$_3$)$_2$), di-tert-butyloxo(N,N'-di-tert-butyl-1,2-vinylenediamide-κ$^2$N,N')hafnium(Hf($^t$BuNCH=CHN$^t$Bu)(O$^t$Bu)$_2$), di-tert-butyloxo(N,N'-di-tert-pentyl-1,2-vinylenediamide-κ$^2$N,N')hafnium(Hf($^t$PeNCH=CHN$^t$Pe)(O$^t$Bu)$_2$), di-tert-pentyloxo(N,N'-di-tert-butyl-1,2-vinylenediamide-κ$^2$N,N')hafnium(Hf($^t$BuNCH=CHN$^t$Bu)(O$^t$Pe)$_2$), di-tert-pentyloxo(N,N'-di-tert-pentyl-1,2-vinylenediamide-κ$^2$N,N')hafnium(Hf($^t$BuNCH=CHN$^t$Bu)(O$^t$Pe)$_2$), di-sec-butyloxo(N,N'-di-tert-butyl-1,2-vinylenediamide-κ$^2$N,N')hafnium(Hf($^t$BuNCH=CHN$^t$Bu)(O$^s$Bu)$_2$), di-sec-butyloxo(N,N'-di-tert-pentyl-1,2-vinylenediamide-κ$^2$N,N')hafnium(Hf($^t$PeNCH=CHN$^t$Pe)(O$^s$Bu)$_2$), dicyclobutyloxo(N,N'-di-tert-butyl-1,2-vinylenediamide-κ$^2$N,N')hafnium(Hf($^t$BuNCH=CHN$^t$Bu)(O(cycloBu))$_2$), dicyclobutyloxo(N, N'-di-tert-pentyl-1,2-vinylenediamide-κ²N,N')hafnium(Hf(ᵗPeNCH=CHNᵗPe)(O(cycloBu))₂), di(1-ethylpropyloxo)(N,N'-di-tert-butyl-1,2-vinylenediamide-κ²N,N')hafnium (Hf(ᵗBuNCH=CHNᵗBu)(OCHEt₂)₂), di(1-ethylpropyloxo)(N,N'-di-tert-pentyl-1,2-vinylenediamide-κ²N,N')hafnium (Hf(ᵗPeNCH=CHNᵗPe)(OCHEt₂)₂), di(1-methylbutyloxo)(N,N'-di-tert-butyl-1,2-vinylenediamide-κ²N,N')hafnium (Hf(ᵗBuNCH=CHNᵗBu)(O(CH(Me)CH₂CH₂CH₃))₂), di(1-methylbutyloxo)(N,N'-di-tert-pentyl-1,2-vinylenediamide-κ²N,N')hafnium(Hf(ᵗPeNCH=CHNᵗPe)(O(CH(Me)CH₂CH₂CH₃))₂), bis(1,1-dimethylbutyloxo)(N,N'-di-tert-butyl-1,2-vinylenediamide-κ²N,N')hafnium (Hf(ᵗBuNCH=CHNᵗBu)(O(C(Me)₂CH₂CH₂CH₃))₂), bis(1,1-dimethylbutyloxo)(N,N'-di-tert-pentyl-1,2-vinylenediamide-κ²N,N')hafnium(Hf(ᵗPeNCH=CHNᵗPe)(O(C(Me)₂CH₂CH₂CH₃))₂), di(1-ethyl-1-methylpropyloxo)-butyloxo(N,N'-di-tert-butyl-1,2-vinylenediamide-κ²N,N')hafnium (Hf(ᵗBuNCH=CHNᵗBu)(O(C(Et)(Me)CH₂CH₃))₂), di(1-ethyl-1-methylpropyloxo)(N,N'-di-tert-pentyl-1,2-vinylenediamide-κ²N,N')hafnium(Hf(ᵗPeNCH=CHNᵗPe)(O(C(Et)(Me)CH₂CH₃))₂), bis(1,1-diethylpropyloxo)(N,N'-di-tert-butyl-1,2-vinylenediamide-κ²N,N')hafnium (Hf(ᵗBuNCH=CHNᵗBu)(OCEt₃)₂), bis(1,1-diethylpropyloxo)(N,N'-di-tert-pentyl-1,2-vinylenediamide-κ²N,N')hafnium (Hf(ᵗPeNCH=CHNᵗPe)(OCEt₃)₂), dicyclohexyloxo(N,N'-di-tert-butyl-1,2-vinylenediamide-κ²N,N')hafnium(Hf(ᵗBuNCH=CHNᵗBu)(OCy)₂), dicyclohexyloxo(N,N'-di-tert-pentyl-1,2-vinylenediamide-κ²N,N')hafnium(Hf(ᵗPeNCH=CHNᵗPe)(OCy)₂), di-tert-butyloxo(N,N'-bis(1,1,3,3-tetramethylbutyl)-1,2-vinylenediamide-κ²N,N')hafnium (Hf(ᵗOctNCH=CHNᵗOct)(OᵗBu)₂)di-tert-pentyloxo(N,N'-bis(1,1,3,3-tetramethylbutyl)-1,2-vinylenediamide-κ²N,N')hafnium(Hf(ᵗOctNCH=CHNᵗOct)(OᵗPe)₂), di-tert-butyloxo(N,N'-di-tert-butyl-1,2-vinylenediamide-κ²N,N')zirconium(Zr(ᵗBuNCH=CHNᵗBu)(OᵗBu)₂), di-tert-butyloxo(N,N'-di-tert-pentyl-1,2-vinylenediamide-κ²N,N')zirconium(Zr(ᵗPeNCH=CHNᵗPe)(OᵗBu)₂), di-tert-pentyloxo(N,N'-di-tert-butyl-1,2-vinylenediamide-κ²N,N')zirconium(Zr(ᵗBuNCH=CHNᵗBu)(OᵗPe)₂), di-tert-pentyloxo(N,N'-di-tert-pentyl-1,2-vinylenediamide-κ²N,N')zirconium(Zr(ᵗPeNCH=CHNᵗPe)(OᵗPe)₂), di-sec-butyloxo(N,N'-di-tert-butyl-1,2-vinylenediamide-κ²N,N')zirconium(Zr(ᵗPeNCH=CHNᵗPe)(OˢBu)₂), di-sec-butyloxo(N,N'-di-tert-pentyl-1,2-vinylenediamide-κ²N,N')zirconium(Zr(ᵗPeNCH=CHNᵗPe)(OˢBu)₂), dicyclobutyloxo(N,N'-di-tert-butyl-1,2-vinylenediamide-κ²N,N')zirconium(Zr(ᵗBuNCH=CHNᵗBu)(O(cycloBu))₂), dicyclobutyloxo(N,N'-di-tert-pentyl-1,2-vinylenediamide-κ²N,N')zirconium(Zr(ᵗPeNCH=CHNᵗPe)(O(cycloBu))₂), di(1-ethylpropyloxo)(N,N'-di-tert-butyl-1,2-vinylenediamide-κ²N,N')zirconium(Zr(ᵗBuNCH=CHNᵗBu)(OCHEt₂)₂), di(1-ethylpropyloxo)(N,N'-di-tert-pentyl-1,2-vinylenediamide-κ²N,N')zirconium(Zr(ᵗPeNCH=CHNᵗPe)(OCHEt₂)₂), di(1-methylbutyloxo)(N,N'-di-tert-butyl-1,2-vinylenediamide-κ²N,N')zirconium(Zr(ᵗBuNCH=CHNᵗBu)(O(CH(Me)CH₂CH₂CH₃))₂), di(1-methylbutyloxo)(N,N'-di-tert-pentyl-1,2-vinylenediamide-κ²N,N')zirconium(Zr(ᵗPeNCH=CHNᵗPe)(O(CH(Me)CH₂CH₂CH₃))₂), bis(1,1-dimethylbutyloxo)(N,N'-di-tert-butyl-1,2-vinylenediamide-κ²N,N')zirconium(Zr(ᵗBuNCH=CHNᵗBu)(O(C(Me)₂CH₂CH₂CH₃))₂), bis(1,1-dimethylbutyloxo)(N,N'-di-tert-pentyl-1,2-vinylenediamide-κ²N,N')zirconium(Zr(ᵗPeNCH=CHNᵗPe)(O(C(Me)₂CH₂CH₂CH₃))₂), di(1-ethyl-1-methylpropyloxo)-butyloxo(N,N'-di-tert-butyl-1,2-vinylenediamide-κ²N,N')zirconium(Zr(ᵗBuNCH=CHNᵗBu)(O(C(Et)(Me)CH₂CH₃))₂), di(1-ethyl-1-methylpropyloxo)(N,N'-di-tert-pentyl-1,2-vinylenediamide-κ²N,N')zirconium(Zr(ᵗPeNCH=CHNᵗPe)(O(C(Et)(Me)CH₂CH₃))₂), bis(1,1-diethylpropyloxo)(N,N'-di-tert-butyl-1,2-vinylenediamide-κ²N,N')zirconium(Zr(ᵗBuNCH=CHNᵗBu)(OCEt₃)₂), bis(1,1-diethylpropyloxo)(N,N'-di-tert-pentyl-1,2-vinylenediamide-κ²N,N')zirconium(Zr(ᵗPeNCH=CHNᵗPe)(OCEt₃)₂), dicyclohexyloxo(N,N'-di-tert-butyl-1,2-vinylenediamide-κ²N,N')zirconium(Zr(ᵗBuNCH=CHNᵗBu)(OCy)₂), dicyclohexyloxo(N,N'-di-tert-pentyl-1,2-vinylenediamide-κ²N,N')zirconium(Zr(ᵗPeNCH=CHNᵗPe)(OCy)₂), di-tert-butyloxo(N,N'-bis(1,1,3,3-tetramethylbutyl)-1,2-vinylenediamide-κ²N,N')zirconium(Zr(ᵗOctNCH=CHNᵗOct)(OᵗBu)₂), and di-tert-pentyloxo(N,N'-bis(1,1,3,3-tetramethylbutyl)-1,2-vinylenediamide-κ²N,N')zirconium(Zr(ᵗOctNCH=CHNᵗOct)(OᵗPe)₂).

Among others, preferred are Ti(ⁱPrNCH=CHNⁱPr)(OMe)₂, Ti(ᵗBuNCH=CHNᵗBu)(OMe)₂, Ti(ᵗPeNCH=CHNᵗPe)(OMe)₂, Ti(ⁱPrNCH=CHNⁱPr)(OEt)₂, Ti(ᵗBuNCH=CHNᵗBu)(OEt)₂, Ti(ᵗPeNCH=CHNᵗPe)(OEt)₂, Ti(ⁱPrNCH=CHNⁱPr)(OPr)₂, Ti(ᵗBuNCH=CHNᵗBu)(OPr)₂, Ti(ᵗPeNCH=CHNᵗPe)(OPr)₂, Ti(ⁱPrNCH=CHNⁱPr)(OⁱPR)₂, Ti(ᵗBuNCH=CHNᵗBu)(OⁱPr)₂, Ti(ᵗPeNCH=CHNᵗPe)(OⁱPr)₂, Ti(ⁱPrNCH=CHNⁱPr)(OˢBu)₂, Ti(ᵗBuNCH=CHNᵗBu)(OˢBu)₂, Ti(ᵗPeNCH=CHNᵗPe)(OˢBu)₂, Ti(ⁱPrNCH=CHNⁱPr)(OᵗBu)₂, Ti(ᵗBuNCH=CHNᵗBu)(OᵗBu)₂, Ti(ᵗPeNCH=CHNᵗPe)(OᵗBu)₂, Si(ⁱPrNCH=CHNⁱPr)(OMe)₂, Si(ᵗBuNCH=CHNᵗBu)(OMe)₂, Si(ᵗPeNCH=CHNᵗPe)(OMe)₂, Si(ⁱPrNCH=CHNⁱPr)(OEt)₂, Si(ᵗBuNCH=CHNᵗBu)(OEt)₂, Si(ᵗPeNCH=CHNᵗPe)(OEt)₂, Si(ⁱPrNCH=CHNⁱPr)(OPr)₂, Si(ᵗBuNCH=CHNᵗBu)(OPr)₂, Si(ᵗPeNCH=CHNᵗPe)(OPr)₂, Si(ⁱPrNCH=CHNⁱPr)(OⁱPr)₂, Si(ᵗBuNCH=CHNᵗBu)(OⁱPr)₂, Si(¹PeNCH=CHNᵗPe)(OⁱPr)₂, Si(ⁱPrNCH=CHNⁱPr)(OˢBu)₂, Si(ᵗBuNCH=CHNᵗBu)(OˢBu)₂, Si(ᵗPeNCH=CHNᵗPe)(OˢBu)₂, Si(ⁱPrNCH=CHNⁱPr)(OᵗBu)₂, Si(ᵗBuNCH=CHNᵗBu)(OᵗBu)₂, Si(ᵗPeNCH=CHNᵗPe)(OᵗBu)₂, Hf(ᵗBuNCH=CHNᵗBu)(OᵗBu)₂, Hf(ᵗPeNCH=CHNᵗPe)(OᵗBu)₂, Hf(ᵗBuNCH=CHNᵗBu)(OᵗPe)₂, Hf(ᵗPeNCH=CHNᵗPe)(OᵗPe)₂, Hf(ᵗBuNCH=CHNᵗBu)(OˢBu)₂, Hf(ᵗPeNCH=CHNᵗPe)(OˢBu)₂, Hf(ᵗBuNCH=CHNᵗBu)(OCHEt₂)₂, Hf(ᵗPeNCH=CHNᵗPe)(OCHEt₂)₂, Hf(ᵗBuNCH=CHNᵗBu)(O(CH(Me)CH₂CH₂CH₃))₂, Hf(ᵗPeNCH=CHNᵗPe)(O(CH(Me)CH₂CH₂CH₃))₂, Hf(ᵗBuNCH=CHNᵗBu)(OCEt₃)₂, Hf(ᵗPeNCH=CHNᵗPe)(OCEt₃)₂, Hf(ᵗBuNCH=CHNᵗBu)(OCy)₂, Hf(ᵗPeNCH=CHNᵗPe)(OCy)₂, Zr(ᵗBuNCH=CHNᵗBu)(OᵗBu)₂, Zr(ᵗPeNCH=CHNᵗPe)(OᵗBu)₂, Zr(ᵗBuNCH=CHNᵗBu)(OᵗPe)₂, Zr(ᵗPeNCH=CHNᵗPe)(OᵗPe)₂, Zr(ᵗBuNCH=CHNᵗBu)(OˢBu)₂, Zr(ᵗPeNCH=CHNᵗPe)(OˢBu)₂, Zr(ᵗBuNCH=CHNᵗBu)(OCHEt₂)₂, Zr(ᵗPeNCH=CHNᵗPe)(OCHEt₂)₂, Zr(ᵗBuNCH=CHNᵗBu)(O(CH(Me)CH₂CH₂CH₃))₂, Zr(ᵗPeNCH=CHNᵗPe)(O(CH(Me)CH₂CH₂CH₃))₂, Zr(ᵗBuNCH=CHNᵗBu)(OCEt₃)₂, Zr(ᵗPeNCH=CHNᵗPe)(OCEt₃)₂, Zr(ᵗBuNCH=CHNᵗBu)(OCy)₂, Zr(ᵗPeNCH=CHNᵗPe)(OCy)₂, and the like, and more preferred are Ti(ᵗBuNCH=CHNᵗBu)(OMe)₂, Ti(ᵗPeNCH=CHNᵗPe)(OMe)₂, Ti(ᵗBuNCH=CHNᵗBu)(OEt)₂, Ti(ᵗPeNCH=CHNᵗPe)(OEt)₂, Ti(ᵗBuNCH=CHNᵗBu)(OPr)₂, Ti(ᵗPeNCH=CHNᵗPe)(OPr)₂, Ti(ᵗBuNCH=CHNᵗBu)(OⁱPr)₂, Ti(ᵗPeNCH=CHN⁴Pe)(OⁱPr)₂, Si(ᵗBuNCH=CHNᵗBu)(OMe)₂, Si(ᵗPeNCH=CHNᵗPe)(OMe)₂, Si(ᵗBuNCH=CHNᵗBu)(OEt)₂, Si(ᵗPeNCH=CHNᵗPe)(OEt)₂, Si(ᵗBuNCH=CHNᵗBu)(OPr)₂, Si(ᵗPeNCH=CHNᵗPe)(OPr)₂, Si(ᵗBuNCH=CHNᵗBu)(OⁱPr)₂, Si(ᵗPeNCH=CHNᵗPe)(OⁱPr)₂, Hf(ᵗBuNCH=CHNᵗBu)(OᵗBu)₂, Hf(ᵗPeNCH=CHNᵗPe)(OᵗBu)₂, Hf(ᵗBuNCH=CHNᵗBu)(OᵗPe)₂, Hf(ᵗPeNCH=CHNᵗPe)(OᵗPr)₂, Zr(ᵗBuNCH=CHNᵗBu)(OᵗBu)₂, Zr(ᵗPeNCH=CHNᵗPe)(OᵗBu)₂, Zr(ᵗBuNCH=CHNᵗBu)(OᵗPe)₂, Zr(ᵗPeNCH=CHNᵗPe)(OᵗPe)₂, and the like.

The vinylenediamide complex (1) for use in the present invention can be produced in accordance with the methods described in Patent Documents 1 and 2.

The vinylenediamide complex where M¹ in formula (1) is a zirconium atom or a hafnium atom can be produced by the production method 1 or 2 for the vinylenediamide complex represented by formula (7):

[Chem. 11]

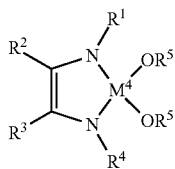

(7)

(wherein M⁴ represents a zirconium atom or a hafnium atom, R¹ to R⁴ have the same meanings as R¹ to R⁴ in formula (1), and R⁵ has the same meaning as R⁵ in formula (1) or QR¹⁰ in formula (2)).

The vinylenediamide complex represented by formula (7) includes, for example, a complex where in the vinylenediamide complex represented by formula (1), M' is a zirconium atom or a hafnium atom, and further includes bis(1,1-dimethyl-2-methoxyethyloxo)(N,N'-di-tert-butyl-1,2-vinylenediamide-κ²N,N')hafnium(Hf(ᵗBuNCH=CHNᵗBu)(OCMe₂CH₂OMe)₂), bis(1,1-dimethyl-2-methoxyethyloxo)(N,N'-di-tert-pentyl-1,2-vinylenediamide-κ²N,N')hafnium (Hf(ⁱPeNCH=CHNᵗPe)(OCMe₂CH₂OMe)₂), (N,N'-di-tert-pentyl-1,2-vinylenediamide-κ²N,N')bis(1-dimethylamino-2-methyl-2-propyloxy)zirconium(Zr(ᵗPeNCH=CHNᵗPe)(OCMe₂CH₂NMe₂)₂), (N,N'-di-tert-butyl-1,2-vinylenediamide-κ²N,N')bis(1-dimethylamino-2-methyl-2-propyloxy)zirconium(Zr(ᵗBuNCH=CHNᵗBu)(OCMe₂CH₂NMe₂)₂), bis(1,1-dimethyl-2-methoxyethyloxo)(N,N'-di-tert-butyl-1,2-vinylenediamide-κ²N,N')zirconium(Zr(ᵗPeNCH=CHNᵗBu)(OCMe₂CH₂OMe)₂), bis(1,1-dimethyl-2-methoxyethyloxo)(N,N'-di-tert-pentyl-1,2-vinylenediamide-κ²N,N')zirconium(Zr(ᵗPeNCH=CHNᵗPe)(OCMe₂CH₂OMe)₂), (N,N'-di-tert-pentyl-1,2-vinylenediamide-κ²N,N')bis(1-dimethylamino-2-methyl-2-propyloxy)zirconium(Zr(ᵗPeNCH=CHNᵗPe)(OCMe₂CH₂NMe₂)₂), (N,N'-di-tert-butyl-1,2-vinylenediamide-κ²N,N')bis(1-dimethylamino-2-methyl-2-propyloxy)zirconium(Zr(ᵗBuNCH=CHNᵗBu)(OCMe₂CH₂NMe₂)₂), and the like.

The production method 1 is a method of reacting a metal tetraalkoxide (8) with a metal tetrachloride (9) and a vinylenediamide alkali metal salt (10) to produce the vinylenediamide complex (7) of the present invention.

Production Method 1:

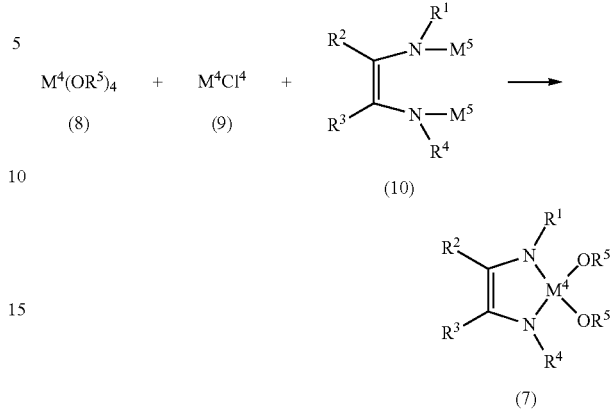

(wherein R¹ to R⁵ and M⁴ have the same meanings as R¹ o R⁵ and M⁴ in formula (7), and M⁵ represents an alkali metal atom).

In the case of producing the vinylenediamide complex (7) by the production method 1, in view of yield of the vinylenediamide complex (7), a metal alkoxide (8) is preferably first reacted with a metal tetrachloride (9) and then reacted with a vinylenediamide alkali metal salt (10).

The molar ratio among metal tetraalkoxide (8), metal tetrachloride (9) and vinylenediamide alkali metal salt (10) is not limited, and in view of yield of the vinylenediamide complex (7), it is preferred to appropriately select the molar ratio of metal tetraalkoxide (8):metal tetrachloride (9) from the range of 4:6 to 6:4 and use the vinylenediamide alkali metal salt (10) in an amount of 0.9 to 1.1 molar times the total molar number of the metal tetraalkoxide (8) and the metal tetrachloride (9).

In terms of good yield of the vinylenediamide complex (7), the production method 1 is preferably performed in an organic solvent in an inert gas atmosphere. Examples of the inert gas include nitrogen gas, helium, neon, and argon. In terms of good yield of the vinylenediamide complex (7), the production method 1 is preferably performed in a nitrogen gas or argon atmosphere.

In the production method 1, as for the metal tetraalkoxide (8) used as a synthesis raw material, a commercial product may be used as it is. Also, a metal tetraalkoxide (8) produced in accordance with the method described, for example, in known literatures such as D.C. Bradley et al., Alkoxo and Aryloxo Derivatives of Metals, first edition, ACADEMIC PRESS, pp. 4-51 (2001), may be used.

Specific examples of the metal tetraalkoxide (8) include tetramethoxohafnium, tetraethoxohafnium, tetrapropoxohafnium, tetraisopropoxohafnium, tetrabutoxohafnium, tetra(isobutyloxo)hafnium, tetra(sec-butyloxo)hafnium, tetra(tert-butyloxo)hafnium, tetra(cyclobutyloxo)hafnium, tetra(pentyloxo)hafnium, tetra(isopentyloxo)hafnium, tetra(1-methylbutyloxo)hafnium, tetra(tert-pentyloxo)hafnium, tetra(neopentyloxo)hafnium, tetra(hexyloxo)hafnium, tetra(cyclohexyloxo)hafnium, tetra(1,3-dimethylbutyloxo)hafnium, tetra(1-ethylpropyloxo)hafnium, tetra(1,1-dimethylbutyloxo)hafnium, tetra(1-ethyl-1-methylpropyloxo)hafnium, tetrakis(1,1-diethylpropyloxo)hafnium, tetrakis(cyclohexyloxo)hafnium, tetrakis(1,1-dimethyl-2-methoxyethyloxo)hafnium, tetrakis(1,1-dimethyl-2-dimethylaminoethyloxo)hafnium, tetramethoxozirconium, tetraisopropoxozirconium, tetrabutoxozirconium, tetra(isobutyloxo)zirconium, tetra(sec-butyloxo)zirconium, tetra(tert-butyloxo)zirconium, tetra(cyclobutyloxo)zirconium, tetra(pentyloxo)zirconium, tetra(isopentyloxo)zirconium, tetra(1-methylbutyloxo)zirconium, tetra(tert-pentyloxo)zirconium, tetra(neopentyloxo)zirconium, tetra(hexyloxo)zirconium, tetra(cyclohexyloxo)zirconium, tetra(1,3-dimethylbutyloxo)zircothum, tetra(1-ethylpropyloxo)zirconium, tetra(1,1-dimethylbutyloxo)zirconium, tetra(1-ethyl-1-methylpropyloxo)zirconium, tetrakis(1,1-diethylpropyloxo)zirconium, tetrakis(cyclohexyloxo)zirconium, tetrakis(1,1-dimethyl-2-methoxyethyloxo)zirconium, and tetrakis(1,1-dimethyl-2-dimethylaminoethyloxo)zirconium. In terms of good yield of the vinylenediamide complex (7) of the present invention, preferred are tetrabutoxohafnium, tetra(isobutyloxo)hafnium, tetra(sec-butyloxo)hafnium, tetra(tert-butyloxo)hafnium, tetra(cyclobutyloxo)hafnium, tetra(pentyloxo)hafnium, tetra(isopentyloxo)hafnium, tetra(1-methylbutyloxo)hafnium, tetra(tert-pentyloxo)hafnium, tetra(neopentyloxo)hafnium, tetra(hexyloxo)hafnium, tetra(cyclohexyloxo)hafnium, tetra(1,3-dimethylbutyloxo)hafnium, tetra(1-ethylpropyloxo)hafnium, tetra(1,1-dimethylbutyloxo)hafnium, tetra(1-ethyl-1-methylpropyloxo)hafnium, tetrakis(1,1-diethylpropyloxo)hafnium, tetrakis(cyclohexyloxo)hafnium, tetrabutoxozirconium, tetra(isobutyloxo)zirconium, tetra(sec-butyloxo)zirconium, tetra(tert-butyloxo)zirconium, tetra(cyclobutyloxo)zirconium, tetra(pentyloxo)zirconium, tetra(isopentyloxo)zirconium, tetra(1-methylbutyloxo)zirconium, tetra(tert-pentyloxo)zirconium, tetra(neopentyloxo)zirconium, tetra(hexyloxo)zirconium, tetra(cyclohexyloxo)zirconium, tetra(1,3-dimethylbutyloxo)zirconium, tetra(1-ethylpropyloxo)zirconium, tetra(1,1-dimethylbutyloxo)zirconium, tetra(1-ethyl-1-methylpropyloxo)zirconium, tetrakis(1,1-diethylpropyloxo)zirconium, and tetrakis(cyclohexyloxo)zirconium, and more preferred are tetra(tert-butyloxo)hafnium, tetra(tert-pentyloxo)hafnium, tetra(tert-butyloxo)zirconium, and tetra(tert-pentyloxo)zirconium.

As for the metal tetrachloride (9) used as a synthesis raw material in the production method 1, a commercial product may be used as it is. The metal tetrachloride specifically includes hafnium tetrachloride and zirconium tetrachloride. In addition, a metal tetrachloride coordinated with ethers such as tetrahydrofuran or nitriles such as acetonitrile may also be used. Examples of the metal tetrachloride coordinated with ethers include tetrachlorobis(tetrahydrofuran)zirconium and tetrachlorobis(tetrahydrofuran)hafnium. Examples of the metal tetrachloride coordinated with nitriles include tetrachlorobis(acetonitrile)zirconium and tetrachlorobis(acetonitrile)hafnium.

The vinylenediamide alkali metal salt (10) and the N,N'-dialkyl-1,4-diaza-1,3-butadiene ($R^1N=CHCH=NR^2$) as a synthesis raw material thereof may be produced in accordance with the method described, for example, in Journal of the American Chemical Society, Vol. 120, page 12714 (1998) or Journal of Organometallic Chemistry, Vol. 301, page 183 (1986). Examples of the alkali metal $M^5$ include a lithium atom, a sodium atom, and a potassium atom. In terms of good yield of the vinylenediamide complex (7), $M^5$ is preferably a lithium atom or a sodium atom, more preferably a lithium atom.

Specific examples of the vinylenediamide alkali metal salt (10) include (N,N'-di-tert-butyl-1,2-vinylenediamide)dilithium, (N,N'-di-tert-butyl-1,2-vinylenediamide)disodium, (N,N'-di-tert-butyl-1,2-vinylenediamide)dipotassium, (N,N'-di-tert-pentyl-1,2-vinylenediamide)dilithium, (N,N'-di-tert-pentyl-1,2-vinylenediamide)disodium, (N,N'-di-tert-pentyl-1,2-vinylenediamide)dipotassium, (N,N'-bis(1,1,3,3-tetramethylbutyl)-1,2-vinylenediamide)dilithium, (N,N'-bis(1,1,3,3-tetramethylbutyl)-1,2-vinylenediamide)disodium, and (N,N'-bis(1,1,3,3-tetramethylbutyl)-1,2-vinylenediamide)dipotassium. In terms of good yield of the vinylenediamide complex (7) of the present invention, preferred are (N,N'-di-tert-butyl-1,2-vinylenediamide)dilithium, (N,N'-di-tert-pentyl-1,2-vinylenediamide)dilithium, and (N,N'-bis(1,1,3,3-tetramethylbutyl)-1,2-vinylenediamide)dilithium.

The production method 1 is preferably performed in an organic solvent in terms of good yield of the vinylenediamide complex (7). The organic solvent which can be used is not limited as long as it is an organic solvent not inhibiting the reaction. Examples of the solvent which can be used include a hydrocarbon solvent such as pentane, hexane, heptane, octane, cyclohexane, methylcyclohexane, ethylcyclohexane, benzene, toluene, xylene and ethylbenzene, and an ether solvent such as diethyl ether, diisopropyl ether, cyclopentyl methyl ether, cyclopentyl ethyl ether, dioxane, tetrahydrofitran, ethylene glycol dimethyl ether and ethylene glycol diethyl ether. One of these may be used alone, or two or more kinds thereof may be mixed at an arbitrary ratio and used. In terms of good yield of the vinylenediamide complex (7), ethers such as diethyl ether, diisopropyl ether, cyclopentyl methyl ether and tetrahydrofuran, and a hydrocarbon solvent such as pentane, hexane, heptane and toluene, are preferred. In the production method 1, the amount of the solvent used is not particularly limited, and the vinylenediamide complex (7) can be produced in good yield by using an appropriately selected amount of solvent.

The reaction temperature and reaction time are not particularly limited and are appropriately selected from the ranges of preferably from −80° C. to 200° C. and from 10 minutes to 120 hours, more preferably from −20° C. to 120° C. and from 1 to 48 hours, whereby the vinylenediamide complex (7) can be produced in good yield.

The vinylenediamide complex (7) produced by the production method 1 may be purified, if desired, by appropriately using a general purification method such as filtration, extraction, distillation, sublimation and crystallization.

When $M^4$ is a zirconium atom, the vinylenediamide complex (7) of the present invention may also be produced according to the production method 2. The production method 2 of the present invention is a method of reacting tetrachlorobis(tetrahydrofuran)zirconium with a vinylenediamide alkali metal salt (10) and a metal alkoxide (11) to produce a vinylenediamide zirconium complex (7-Zr) where $M^4$ in the vinylenediamide complex represented by formula (7) is a zirconium atom.

Production Method 2:

[Chem. 13]

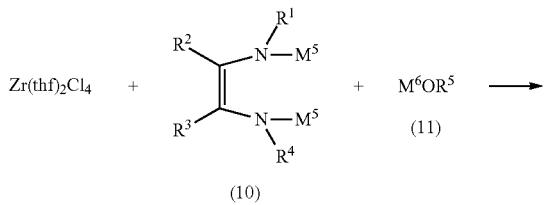

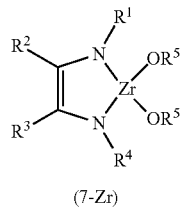

(7-Zr)

(wherein R¹ to R⁴ have the same meanings as R¹ to R⁴ in formula (7), and each of M⁵ and M⁶ represents an alkali metal atom).

The tetrachlorobis(tetrahydrofuran)zirconium can be prepared by reacting zirconium tetrachloride with tetrahydrofuran in a solvent such as diethyl ether, hexane and dichloromethane.

Examples of the alkali metal M⁶ in the metal alkoxide (11) include lithium, sodium, and potassium. As for the metal alkoxide (11), a commercial product may be used as it is and in addition, a metal alkoxide prepared by a known preparation method, for example, by reacting an alkali metal alkyl compound such as butyllithium or an alkali metal amide such as sodium amide with an alcohol, may also be used.

Specific examples of the metal alkoxide (11) include methoxylithium, ethoxylithium, propoxylithium, isopropoxylithium, butoxylithium, isobutyloxylithium, sec-butyloxylithium, tert-butyloxylithium, cyclobutyloxylithium, pentyloxylithium, isopentyloxolithium, 1-methylbutyloxylithium, tert-pentyloxylithium, neopentyloxylithium, hexyloxylithium, cyclohexyloxylithium, 1,3-dimethylbutyloxylithium, 1-ethylpropyloxylithium, 1,1-dimethylbutyloxylithium, 1-ethyl-1-methylpropyloxylithium, 1,1-diethylpropyloxylithium, cyclohexyloxylithium, 1,1-dimethyl-2-methoxyethyloxylithium, 1,1-dimethyl-2-dimethylaminoethyloxylithium, methoxysodium, ethoxysodium, propoxysodium, isopropoxysodium, butoxysodium, isobutyloxysodium, sec-butyloxysodium, tert-butyloxysodium, cyclobutyloxysodium, pentyloxysodium, isopentyloxosodium, 1-methylbutyloxysodium, tert-pentyloxysodium, neopentyloxysodium, hexyloxysodium, cyclohexyloxysodium, 1,3-dimethylbutyloxysodium, 1-ethylpropyloxysodium, 1,1-dimethylbutyloxysodium, 1-ethyl-1-methylpropyloxysodium, 1,1-diethylpropyloxysodium, cyclohexyloxysodium, 1,1-dimethyl-2-methoxyethyloxysodium, 1,1-dimethyl-2-dimethylaminoethyloxysodium, methoxypotassium, ethoxypotassium, propoxypotassium, isopropoxypotassium, butoxypotassium, isobutyloxypotassium, sec-butyloxypotassium, tert-butyloxypotassium, cyclobutyloxypotassium, pentyloxypotassium, isopentyloxopotassium, 1-methylbutyloxypotassium, tert-pentyloxypotassium, neopentyloxypotassium, hexyloxypotassium, cyclohexyloxypotassium, 1,3-dimethylbutyloxypotassium, 1-ethylpropyloxypotassium, 1,1-dimethylbutyloxypotassium, 1-ethyl-1-methylpropyloxypotassium, 1,1-diethylpropyloxypotassium, cyclohexyloxypotassium, 1,1-dimethyl-2-methoxyethyloxypotassium, and 1,1-dimethyl-2-dimethylaminoethyloxypotassium. In view of yield of the vinylenediamide zirconium complex (7-Zr), preferred are butoxylithium, isobutyloxylithium, sec-butyl oxylithium, tert-butyloxylithium, cyclobutyloxylithium, pentyloxylithium, isopentyloxolithium, 1-methylbutyloxylithium, tert-pentyloxylithium, neopentyloxylithium, hexyloxylithium, cyclohexyloxylithium, 1,3-dimethylbutyloxylithium, 1-ethylpropyloxylithium, 1,1-dimethylbutyloxylithium, 1-ethyl-1-methylpropyloxylithium, 1,1-diethylpropyloxylithium and cyclohexyloxylithium, and more preferred are tert-butyloxylithium and tert-pentyloxylithium.

In the production method 2, in terms of good yield of the vinylenediamide zirconium complex (7-Zr), tetrachlorobis(tetrahydrofuran)zirconium is preferably first reacted with a vinylenediamide alkali metal salt and then reacted with a metal alkoxide (11).

In terms of good yield of the vinylenediamide zirconium complex (7-Zr), the production method 2 is preferably performed in an organic solvent in an inert gas atmosphere. Examples of the inert gas include nitrogen gas, helium, neon, and argon. In terms of good yield of the vinylenediamide zirconium complex (7-Zr), the production method 2 is preferably performed in a nitrogen gas or argon atmosphere.

The organic solvent which can be used in the production method 2 is not limited as long as it is an organic solvent not inhibiting the reaction. Examples of the solvent which can be used include a hydrocarbon solvent such as pentane, hexane, heptane, octane, cyclohexane, methylcyclohexane, ethylcyclohexane, benzene, toluene, xylene and ethylbenzene, and an ether solvent such as diethyl ether, diisopropyl ether, cyclopentyl methyl ether, cyclopentyl ethyl ether, dioxane, tetrahydrofuran, ethylene glycol dimethyl ether and ethylene glycol diethyl ether. One of these may be used alone, or two or more kinds thereof may be mixed at an arbitrary ratio and used. In terms of good yield of the vinylenediamide zirconium complex (7-Zr), an ether solvent such as diethyl ether, diisopropyl ether, cyclopentyl methyl ether, tetrahydrofuran and ethylene glycol dimethyl ether is preferred, and it is also preferred to use a mixture of a hydrocarbon solvent such as pentane, hexane, heptane and toluene and an ether solvent such as diethyl ether, diisopropyl ether, cyclopentyl methyl ether, tetrahydrofuran and ethylene glycol dimethyl ether.

In the production method 2, the amount of the solvent used is not particularly limited, and the vinylenediamide zirconium complex (7-Zr) can be produced in good yield by using an appropriately selected amount of solvent. The amount of the metal alkoxide (11) used is preferably 2 equivalents or more per equivalent of tetrachlorobis(tetrahydrofurn)zirconium, because the yield of the vinylenediamide zirconium complex (7-Zr) is good, and the amount used is preferably from 2 to 2.2 equivalents per equivalent of tetrachlorobis(tetrahydrofuran)zirconium, because the reaction can be completed without excess or deficiency. The reaction temperature and reaction time in the production method 2 are not particularly limited and are appropriately selected from the ranges of preferably from −80° C. to 120° C. and from 10 minutes to 120 hours, more preferably from −80° C. to 60° C. and from 1 to 48 hours, whereby the vinylenediamide zirconium complex (7-Zr) can be produced in good yield.

The vinylenediamide zirconium complex (7-Zr) produced by the production method 2 may be purified, if desired, by appropriately using a general purification method such as filtration, extraction, distillation, sublimation and crystallization.

Also, the present invention is a film-forming material produced by reacting a vinylenediamide complex represented by formula (2):

[Chem. 14]

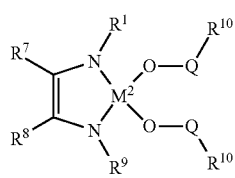

(2)

(wherein $M^2$ represents a titanium atom or a silicon atom, each of $R^6$ and $R^9$ independently represents a $C_1$-$C_{12}$ alkyl group, each of $R^7$ and $R^8$ independently represents a hydrogen atom or a $C_1$-$C_4$ alkyl group, $R^{10}$ represents a $C_1$-$C_6$ alkoxy group or a di($C_1$-$C_6$ alkyl)amino group, and Q represents a $C_2$-$C_6$ methylene group which may be substituted with a $C_1$-$C_3$ alkyl group) with one or more kinds of oxidizing agents selected from the group consisting of oxygen gas, air, ozone, water and hydrogen peroxide.

The present invention is described in more detail below. First, the definitions of $R^6$, $R^7$, $R^8$, $R^9$, $R^{10}$ and Q are described. The $C_3$-$C_{12}$ alkyl group represented by $R^6$ and $R^9$ may be any of linear, branched and cyclic alkyl groups. Specific examples thereof include a propyl group, an isopropyl group, a cyclopropyl group, a butyl group, a isobutyl group, a sec-butyl group, a tert-butyl group, a cyclobutyl group, a pentyl group, an isopentyl group, a neopentyl group, a tert-pentyl group, a 1-methylbutyl group, a 2-methylbutyl group, a 1,2-dimethylpropyl group, a 1-ethylpropyl group, a cyclopentyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclohexyl group, a cyclopropylmethyl group, a cyclopropylethyl group, a cyclobutylmethyl group, a heptyl group, a cyclohexylmethyl group, a 1,1-diethyl-propyl group, a 2-methylcyclohexyl group, a 4-methylcyclohexyl group, an octyl group, a 1,1-diethyl-2-methylpropyl group, a 2,5-dimethylcyclohexyl group, a 3,5-dimethylcyclohexyl group, a 1,1,3,3-tetramethylbutyl group, a 1-methyl-1-propylbutyl group, a 1,1,2,3,3-pentamethylbutyl group, a 1,1-diethyl-3,3-dimethylbutyl group, an adamantyl group, a 1,1-dimethyloctyl group, a 1,1-dipropylbutyl group, a 1,1-dimethyldecyl group, a 1,1-diethyloctyl group, and a 1-butyl-1-propylpentyl group. From the standpoint that the vinylenediamide complex (2) of the present invention can be produced in good yield, each of $R^6$ and $R^9$ is independently, preferably a $C_3$-$C_8$ alkyl group, more preferably a secondary or tertiary $C_3$-$C_5$ alkyl group, still more preferably an isopropyl group, a tert-butyl group or a tert-pentyl group.

Each of $R^7$ and $R^8$ represents a $C_1$-$C_4$ alkyl group. The $C_1$-$C_4$ alkyl group may be any of linear, branched and cyclic alkyl groups, and specific examples thereof include a methyl group, an ethyl group, a propyl group, an isopropyl group, a cyclopropyl group, a butyl group, an isobutyl group, a sec-butyl group, a tert-butyl group, and a cyclobutyl group. From the standpoint that the vinylenediamide complex (2) of the present invention can be produced in good yield, each of $R^7$ and $R^8$ is independently, preferably a hydrogen atom, a methyl group or an ethyl group, more preferably a hydrogen atom.

The $C_1$-$C_6$ alkoxy group represented by $R^{10}$ may be any of linear, branched and cyclic alkoxy groups, and examples thereof include a methoxy group, an ethoxy group, a propoxy group, an isopropyloxy group, a cyclopropyloxy group, a butoxy group, a sec-butyloxy group, an isobutyloxy group, a tert-butyloxy group, a cyclobutyloxy group, a pentyloxy group, a 1,1-dimethylpropyloxy group (tert-pentyloxy group), 1,2-dimethylpropyloxy group, a 2,2-dimethylpropyloxy group (neopentyloxy group), a cyclopentyloxy group, a hexyloxy group, a 1,1-dimethylbutyloxy group, a 2,2-dimethylbutyloxy group, a 3,3-dimethylbutyloxy group, and a cyclohexyloxy group. From the standpoint that the vinylenediamide complex (2) of the present invention can be produced in good yield, the alkoxy group is preferably a $C_1$-$C_4$ alkoxy group, and preferred examples include a methoxy group, an ethoxy group, a propoxy group, an isopropyloxy group, a cyclopropyloxy group, a butoxy group, a sec-butyloxy group, an isobutyloxy group, a tert-butyloxy group, and a cyclobutyloxy group.

The alkyl group in the di($C_1$-$C_6$ alkyl)amino group represented by $R^{19}$ may be any of linear, branched and cyclic alkyl groups, and two $C_1$-$C_6$ alkyl groups may be the same as or different from each other. Examples of the di($C_1$-$C_6$ alkyl) amino group include a dimethylamino group, an ethyl(methyl)amino group, a methyl(propyl)amino group, an isopropyl (methyl)amino group, a cyclopropyl(methyl)amino group, a butyl(methyl)amino group, an isobutyl(methyl)amino group, a sec-butyl(methyl)amino group, a tert-butyl(methyl)amino group, a cyclobutyl(methyl)amino group, a pentyl(methyl) amino group, an isopentyl(methyl)amino group, a methyl (neopentyl)amino group, a tert-pentyl(methyl)amino group, a cyclopentyl(methyl)amino group, a hexyl(methyl)amino group, a cyclohexyl(methyl)amino group, a diethylamino group, an ethyl(propyl)amino group, an ethyl(isopropyl) amino group, a cyclopropyl(ethyl)amino group, a butyl(ethyl)amino group, an ethyl(isobutyl)amino group, a sec-butyl (ethyl)amino group, a tert-butyl(ethyl)amino group, an ethyl (pentyl)amino group, an ethyl(isopentyl)amino group, an ethyl(neopentyl)amino group, an ethyl(tert-pentyl)amino group, an ethyl(hexyl)amino group, a cyclohexyl(ethyl) amino group, a dipropylamino group, a butyl(propyl)amino group, a tert-butyl(propyl)amino group, a pentyl(propyl) amino group, a hexyl(propyl)amino group, a diisopropylamino group, a butyl(isopropyl)amino group, a tert-butyl (isopropyl)amino group, a pentyl(isopropyl)amino group, a hexyl(isopropyl)amino group, a dibutylamino group, a diisobutylamino group, a di(sec-butyl)amino group, a dipentylamino group, a dihexylamino group, and a di(cyclohexyl) amino group. From the standpoint that the vinylenediamide complex (2) can be synthesized in good yield, a di($C_1$-$C_4$ alkyl)amino group is preferred, and a dimethylamino group or a diethylamino group is more preferred.

The $C_2$-$C_6$ methylene group represented by Q includes an ethylene group, a trimethylene group, a tetramethylene group, a pentamethylene group, and a hexamethylene group. These methylene groups may be substituted with a $C_1$-$C_3$ alkyl group. The $C_1$-$C_3$ alkyl group include a methyl group, an ethyl group, a propyl group, an isopropyl group, and a cyclopropyl group. From the standpoint that the vinylenediamide complex (2) of the present invention can be synthesized in good yield, Q is preferably an ethylene group or a trimethylene group, which may be substituted with a methyl group or an ethyl group.

Specific examples of the vinylenediamide complex represented by formula (2) include (N,N'-diisopropyl-1,2-vinylenediamide-$\kappa^2$N,N')bis(2-methoxyethyloxo)titanium(Ti ($^i$PrNCH=CHN$^i$Pr)(OCH$_2$CH$_2$OMe$_2$), (N,N'-di-tert-butyl- 1,2-vinylenediamide-κ²N,N')bis(2-methoxyethyloxo)titanium(Ti(ᵗBuNCH=CHNᵗBu)(OCH₂CH₂OMe)₂), (N,N'-di-tert-pentyl-1,2-vinylenediamide-κ²N,N')bis(2-methoxyethyloxo)titanium(Ti(ᵗPeNCH=CHNᵗPe)(OCH₂CH₂OMe)₂), (N,N'-bis(1,1,3,3-tetramethylbutyl)-1,2-vinylenediamide-κ²N,N')bis(2-methoxyethyloxo)titanium(Ti(ᵗOctNCH=CHNᵗOct)(OCH₂CH₂OMe)₂), (N,N'-diisopropyl-1,2-vinylenediamide-κ²N,N')bis(2-ethoxyethyloxo)titanium(Ti(ⁱPrNCH=CHNⁱPr)(OCH₂CH₂OEt)₂), (N,N'-di-tert-butyl-1,2-vinylenediamide-κ²N,N')bis(2-ethoxyethyloxo)titanium(Ti(ᵗBuNCH=CHNᵗBu)(OCH₂CH₂OEt)₂), (N,N'-di-tert-pentyl-1,2-vinylenediamide-κ²N,N')bis(2-ethoxyethyloxo)titanium(Ti(ᵗPeNCH=CHNᵗPe)(OCH₂CH₂OEt)₂), (N,N'-bis(1,1,3,3-tetramethylbutyl)-1,2-vinylenediamide-κ²N,N')bis(2-ethoxyethyloxo)titanium(Ti(ᵗOctNCH=CHNᵗOct)(OCH₂CH₂OEt)₂), (N,N'-diisopropyl-1,2-vinylenediamide-κ²N,N')bis(2-propoxyethyloxo)titanium(Ti(ⁱPrNCH=CHNⁱPr)(OCH₂CH₂OPr)₂), (N,N'-di-tert-butyl-1,2-vinylenediamide-κ²N,N')bis(2-propoxyethyloxo)titanium(Ti(ᵗBuNCH=CHNᵗBu)(OCH₂CH₂OPr)₂), (N,N'-di-tert-pentyl-1,2-vinylenediamide-κ²N,N')bis(2-propoxyethyloxo)titanium(Ti(ᵗPeNCH=CHNᵗPe)(OCH₂CH₂OPr)₂), (N,N'-bis(1,1,3,3-tetramethylbutyl)-1,2-vinylenediamide-κ²N,N')bis(2-propoxyethyloxo)titanium(Ti(ᵗOctNCH=CHNᵗOct)(OCH₂CH₂OPr)₂), (N,N'-diisopropyl-1,2-vinylenediamide-κ²N,N')bis(2-isopropoxyethyloxo)titanium(Ti(ⁱPrNCH=CHNⁱPr)(OCH₂CH₂OⁱPr)₂), tert-butyl-1,2-vinylenediamide-κ²N,N')bis(2-isopropoxyethyloxo)titanium(Ti(ᵗBuNCH=CHNᵗBu)(OCH₂CH₂OⁱPr)₂), (N,N'-di-tert-pentyl-1,2-vinylenediamide-κ²N,N')bis(2-isopropoxyethyloxo)titanium(Ti(ᵗPeNCH=CHNᵗPe)(OCH₂CH₂OⁱPr)₂),
(N,N'-bis(1,1,3,3-tetramethylbutyl)-1,2-vinylenediamide-κ²N,N')bis(2-isopropoxyethyloxo)titanium(Ti(ᵗOctNCH=CHNᵗOct)(OCH₂CH₂OⁱPr)₂), (N,N'-diisopropyl-1,2-vinylenediamide-κ²N,N')bis(2-tert-butoxyethyloxo)titanium(Ti(ⁱPrNCH=CHNⁱPr)(OCH₂CH₂OᵗBu)₂), (N,N'-di-tert-butyl-1,2-vinylenediamide-κ²N,N')bis(2-tert-butoxyethyloxo)titanium(Ti(ᵗBuNCH=CHNᵗBu)(OCH₂CH₂OᵗBu)₂), (N,N'-di-tert-pentyl-1,2-vinylenediamide-κ²N,N')bis(2-tert-butoxyethyloxo)titanium(Ti(ᵗPeNCH=CHNᵗPe)(OCH₂CH₂OᵗBu)₂), (N,N'-bis(1,1,3,3-tetramethylbutyl)-1,2-vinylenediamide-κ²N,N')bis(2-tert-butoxyethyloxo)titanium(Ti(ᵗOctNCH=CHNᵗOct)(OCH₂CH₂OᵗBu)₂), (N,N'-diisopropyl-1,2-vinylenediamide-κ²N,N')bis(1-methyl-2-methoxyethyloxo)titanium(Ti(ⁱPrNCH=CHNⁱPr)(OCHMeCH₂OMe)₂), (N,N'-di-tert-butyl-1,2-vinylenediamide-κ²N,N')bis(1-methyl-2-methoxyethyloxo)titanium(Ti(ᵗBuNCH=CHNᵗBu)(OCHMeCH₂OMe)₂), (N,N'-di-tert-pentyl-1,2-vinylenediamide-κ²N,N')bis(1-methyl-2-methoxyethyloxo)titanium(Ti(ᵗPeNCH=CHNᵗPe)(OCHMeCH₂OMe)₂), (N,N'-bis(1,1,3,3-tetramethylbutyl)-1,2-vinylenediamide-κ²N,N')bis(1-methyl-2-methoxyethyloxo)titanium(Ti(ᵗOctNCH=CHNᵗOct)(OCHMeCH₂OMe)₂), (N,N'-diisopropyl-1,2-vinylenediamide-κ²N,N')bis(1,1-dimethyl-2-methoxyethyloxo)titanium(Ti(ⁱPrNCH=CHNⁱPr)(OCMe₂CH₂OMe)₂), (N,N'-di-tert-butyl-1,2-vinylenediamide-κ²N,N')bis(1,1-dimethyl-2-methoxyethyloxo)titanium(Ti(ᵗBuNCH=CHNᵗBu)(OCMe₂CH₂OMe)₂), (N,N'-di-tert-pentyl-1,2-vinylenediamide-κ²N,N')bis(1,1-dimethyl-2-methoxyethyloxo)titanium(Ti(ᵗPeNCH=CHNᵗPe)(OCMe₂CH₂OMe)₂), (N,N'-bis(1,1,3,3-tetramethylbutyl)-1,2-vinylenediamide-κ²N,N')bis(1,1-dimethyl-2-methoxyethyloxo)titanium(Ti(ᵗOctNCH=CHNᵗOct)(OCMe₂CH₂OMe)₂), (N,N'-diisopropyl-1,2-vinylenediamide-κ²N,N')bis(3-methoxypropyloxo)titanium(Ti(ⁱPrNCH=CHNⁱPr)(OCH₂CH₂CH₂OMe)₂),
(N,N'-di-tert-butyl-1,2-vinylenediamide-κ²N,N')bis(3-methoxypropyloxo)titanium(Ti(ᵗBuNCH=CHNᵗBu)(OCH₂CH₂CH₂OMe)₂), (N,N'-di-tert-pentyl-1,2-vinylenediamide-κ²N,N')bis(3-methoxypropyloxo)titanium(Ti(ᵗPeNCH=CHNᵗPe)(OCH₂CH₂CH₂OMe)₂), (N,N'-bis(1,1,3,3-tetramethylbutyl)-1,2-vinylenediamide-κ²N,N')bis(3-methoxypropyloxo)titanium(Ti(ᵗOctNCH=CHNᵗOct)(OCH₂CH₂CH₂OMe)₂), (N,N'-diisopropyl-1,2-vinylenediamide-κ²N,N')bis(1-ethyl-2-methoxyethyloxo)titanium(Ti(ⁱPrNCH=CHNⁱPr)(OCHEtCH₂OMe)₂), (N,N'-di-tert-butyl-1,2-vinylenediamide-κ²N,N')bis(1-ethyl-2-methoxyethyloxo)titanium(Ti(ᵗBuNCH=CHNᵗBu)(OCHEtCH₂OMe)₂), (N,N'-di-tert-pentyl-1,2-vinylenediamide-κ²N,N')bis(1-ethyl-2-methoxyethyloxo)titanium(Ti(ᵗPeNCH=CHNᵗPe)(OCHEtCH₂OMe)₂), (N,N'-bis(1,1,3,3-tetramethylbutyl)-1,2-vinylenediamide-κ²N,N')bis(1-ethyl-2-methoxyethyloxo)titanium(Ti(ᵗOctNCH=CHNᵗOct)(OCHEtCH₂OMe)₂), (N,N'-diisopropyl-1,2-vinylenediamide-κ²N,N')bis(2-methoxypropyloxo)titanium(Ti(ⁱPrNCH=CHNⁱPr)(OCH₂CH(OMe)CH₃)₂), (N,N'-di-tert-butyl-1,2-vinylenediamide-κ²N,N')bis(2-methoxypropyloxo)titanium(Ti(ᵗBuNCH=CHNᵗBu)(OCH₂CH(OMe)CH₃)₂), (N,N'-di-tert-pentyl-1,2-vinylenediamide-κ²N,N')bis(2-methoxypropyloxo)titanium(Ti(ᵗPeNCH=CHNᵗPe)(OCH₂CH(OMe)CH₃)₂), (N,N'-bis(1,1,3,3-tetramethylbutyl)-1,2-vinylenediamide-κ²N,N')bis(2-methoxypropyloxo)titanium(Ti(ᵗOctNCH=CHNᵗOct)(OCH₂CH(OMe)CH₃)₂), (N,N'-diisopropyl-1,2-vinylenediamide-κ²N,N')bis(2-methoxybutyloxo)titanium(Ti(ⁱPrNCH=CHNⁱPr)(OCH₂CH(OMe)CH₂CH₃)₂), (N,N'-di-tert-butyl-1,2-vinylenediamide-κ²N,N')bis(2-methoxybutyloxo)titanium(Ti(ᵗBuNCH=CHNᵗBu)(OCH₂CH(OMe)CH₂CH₃)₂), (N,N'-di-tert-pentyl-1,2-vinylenediamide-κ²N,N')bis(2-methoxybutyloxo)titanium(Ti(ᵗPeNCH=CHNᵗPe)(OCH₂CH(OMe)CH₂CH₃)₂), (N,N'-bis(1,1,3,3-tetramethylbutyl)-1,2-vinylenediamide-κ²N,N')bis(2-methoxybutyloxo)titanium(Ti(ᵗOctNCH=CHNᵗOct)(OCH₂CH(OMe)CH₂CH₃)₂),
(N,N'-diisopropyl-1,2-vinylenediamide-κ²N,N')bis(2-(diethylamino)ethyloxo)titanium(Ti(ⁱPrNCH=CHNⁱPr)(OCH₂CH₂NEt₂)₂), (N,N'-di-tert-butyl-1,2-vinylenediamide-κ²N,N')bis(2-(diethylamino)ethyloxo)titanium(Ti(ᵗBuNCH=CHNᵗBu)(OCH₂CH₂NEt₂)₂), (N,N'-di-tert-pentyl-1,2-vinylenediamide-κ²N,N')bis(2-(diethylamino)ethyloxo)titanium(Ti(ᵗPeNCH=CHNᵗPe)(OCH₂CH₂NEt₂)₂), (N,N'-bis(1,1,3,3-tetramethylbutyl)-1,2-vinylenediamide-κ²N,N')bis(2-(diethylamino)ethyloxo)titanium(Ti(ᵗOctNCH=CHNᵗOct)(OCH₂CH₂NEt₂)₂), (N,N'-diisopropyl-1,2-vinylenediamide-κ²N,N')bis(2-(dimethylamino)ethyloxo)titanium(Ti(ⁱPrNCH=CHNⁱPr)(OCH₂CH₂NMe₂)₂), (N,N'-di-tert-butyl-1,2-vinylenediamide-κ²N,N')bis(2-(dimethylamino)ethyloxo)titanium(Ti(ᵗBuNCH=CHNᵗBu)(OCH₂CH₂NMe₂)₂), (N,N'-di-tert-pentyl-1,2-vinylenediamide-κ²N,N')bis(2-(dimethylamino)ethyloxo)titanium(Ti(ᵗPeNCH=CHNᵗPe)(OCH₂CH₂NMe₂)₂), (N,N'-bis(1,1,3,3-tetramethylbutyl)-1,2-vinylenediamide-κ²N,N')bis(2-(dimethylamino)ethyloxo)titanium(Ti(ᵗOctNCH=CHNᵗOct)(OCH₂CH₂NMe₂)₂), (N,N'-diisopropyl-1,2-vinylenediamide-κ²N,N')bis(2-(diethylamino)propyloxo)titanium(Ti(ⁱPrNCH=CHNⁱPr)(OCH₂CH₂CH₂NEt₂)₂), (N,N'-di-tert-butyl-1,2-vinylenediamide-κ²N,N')bis(2-(diethylamino)propyloxo)titanium(Ti (ᵗBuNCH=CHNᵗBu)(OCH₂CH₂CH₂NEt₂)₂), (N,N'-di-tert-pentyl-1,2-vinylenediamide-κ²N,N')bis(2-(diethylamino)propyloxo)titanium(Ti(ᵗPeNCH=CHNᵗPe)(OCH₂CH₂CH₂NEt₂)₂), (N,N'-bis(1,1,3,3-tetramethylbutyl)-1,2-vinylenediamide-κ²N,N')bis(2-(diethylamino)propyloxo)titanium(Ti(ᵗOctNCH=CHNᵗOct)(OCH₂CH₂CH₂NEt₂)₂), (N,N'-diisopropyl-1,2-vinylenediamide-κ²N,N')bis(2-(dimethylamino)propyloxo)titanium(Ti(ⁱPrNCH=CHNⁱPr)(OCH₂CH₂CH₂NMe₂)₂), (N,N'-di-tert-butyl-1,2-vinylenediamide-κ²N,N')bis(2-(dimethylamino)propyloxo)titanium(Ti(ᵗBuNCH=CHNᵗBu)(OCH₂CH₂CH₂NMe₂)₂), (N,N'-di-tert-pentyl-1,2-vinylenediamide-κ²N,N')bis(2-(dimethylamino)propyloxo)titanium(Ti(ᵗPeNCH=CHNᵗPe)(OCH₂CH₂CH₂NMe₂)₂), (N,N'-bis(1,1,3,3-tetramethylbutyl)-1,2-vinylenediamide-κ²N,N')bis(2-(dimethylamino)propyloxo)titanium(Ti(ᵗOctNCH=CHNᵗOct)(OCH₂CH₂CH₂NMe₂)₂), (N,N'-diisopropyl-1,2-vinylenediamide-κ²N,N')bis(2-methoxyethyloxo)silane(Si(ⁱPrNCH=CHNⁱPr)(OCH₂CH₂OMe)₂), (N,N'-di-tert-butyl-1,2-vinylenediamide-κ²N,N')bis(2-methoxyethyloxo)silane(Si(ᵗBuNCH=CHNᵗBu)(OCH₂CH₂OMe)₂), (N,N'-di-tert-pentyl-1,2-vinylenediamide-κ²N,N')bis(2-methoxyethyloxo)silane(Si(ᵗPeNCH=CHNᵗPe)(OCH₂CH₂OMe)₂), (N,N'-bis(1,1,3,3-tetramethylbutyl)-1,2-vinylenediamide-κ²N,N')bis(2-methoxyethyloxo)silane(Si(ᵗOctNCH=CHNᵗOct)(OCH₂CH₂OMe)₂), (N,N'-diisopropyl-1,2-vinylenediamide-κ²N,N')bis(2-ethoxyethyloxo)silane(Si(ⁱPrNCH=CHNⁱPr)(OCH₂CH₂OEt)₂), (N,N'-di-tert-butyl-1,2-vinylenediamide-κ²N,N')bis(2-ethoxyethyloxo)silane(Si(ᵗBuNCH=CHNᵗBu)(OCH₂CH₂OEt)₂), (N,N'-di-tert-pentyl-1,2-vinylenediamide-κ²N,N')bis(2-ethoxyethyloxo)silane(Si(ᵗPeNCH=CHNᵗPe)(OCH₂CH₂OEt)₂), (N,N'-bis(1,1,3,3-tetramethylbutyl)-1,2-vinylenediamide-κ²N,N')bis(2-ethoxyethyloxo)silane(Si(ᵗOctNCH=CHNᵗOct)(OCH₂CH₂OEt)₂), (N,N'-diisopropyl-1,2-vinylenediamide-κ²N,N')bis(2-propoxyethyloxo)silane(Si(ⁱPrNCH=CHNⁱPr)(OCH₂CH₂OPr)₂), (N,N'-di-tert-butyl-1,2-vinylenediamide-κ²N,N')bis(2-propoxyethyloxo)silane(Si(ᵗBuNCH=CHNᵗBu)(OCH₂CH₂OPr)₂), (N,N'-di-tert-pentyl-1,2-vinylenediamide-κ²N,N')bis(2-propoxyethyloxo)silane(Si(ᵗPeNCH=CHNᵗPe)(OCH₂CH₂OPr)₂), (N,N'-bis(1,1,3,3-tetramethylbutyl)-1,2-vinylenediamide-κ²N,N')bis(2-propoxyethyloxo)silane(Si(ᵗOctNCH=CHNᵗOct)(OCH₂CH₂OPr)₂), (N,N'-diisopropyl-1,2-vinylenediamide-κ²N,N')bis(2-isopropoxyethyloxo)silane(Si(ⁱPrNCH=CHNⁱPr)(OCH₂CH₂OⁱPr)₂), (N,N'-di-tert-butyl-1,2-vinylenediamide-κ²N,N')bis(2-isopropoxyethyloxo)silane(Si(ᵗBuNCH=CHNᵗBu)(OCH₂CH₂OⁱPr)₂), (N,N'-di-tert-pentyl-1,2-vinylenediamide-κ²N,N')bis(2-isopropoxyethyloxo)silane(Si(ᵗPeNCH=CHNᵗPe)(OCH₂CH₂OⁱPr)₂), (N,N'-bis(1,1,3,3-tetramethylbutyl)-1,2-vinylenediamide-κ²N,N')bis(2-isopropoxyethyloxo)silane(Si(ᵗOctNCH=CHNᵗOct)(OCH₂CH₂OⁱPr)₂), (N,N'-diisopropyl-1,2-vinylenediamide-κ²N,N')bis(2-tert-butoxyethyloxo)silane(Si(ⁱPrNCH=CHNⁱPr)(OCH₂CH₂OᵗBu)₂), (N,N'-di-tert-butyl-1,2-vinylenediamide-κ²N,N')bis(2-tert-butoxyethyloxo)silane(Si(ᵗBuNCH=CHNᵗBu)(OCH₂CH₂OᵗBu)₂), (N,N'-di-tert-pentyl-1,2-vinylenediamide-κ²N,N')bis(2-tert-butoxyethyloxo)silane(Si(ᵗPeNCH=CHNᵗPe)(OCH₂CH₂OᵗBu)₂), (N,N'-bis(1,1,3,3-tetramethylbutyl)-1,2-vinylenediamide-κ²N,N')bis(2-tert-butoxyethyloxo)silane(Si(ᵗOctNCH=CHNᵗOct)(OCH₂CH₂OᵗBu)₂), (N,N'-diisopropyl-1,2-vinylenediamide-κ²N,N')bis(1-methyl-2-methoxyethyloxo)silane(Si(ⁱPrNCH=CHNⁱPr)(OCHMeCH₂OMe)₂), (N,N'-di-tert-butyl-1,2-vinylenediamide-κ²N,N')bis(1-methyl-2-methoxyethyloxo)silane(Si(ᵗBuNCH=CHNᵗBu)(OCHMeCH₂OMe)₂), (N,N'-di-tert-pentyl-1,2-vinylenediamide-κ²N,N')bis(1-methyl-2-methoxyethyloxo)silane(Si(ᵗPeNCH=CHNᵗPe)(OCHMeCH₂OMe)₂), (N,N'-bis(1,1,3,3-tetramethylbutyl)-1,2-vinylenediamide-κ²N,N')bis(1-methyl-2-methoxyethyloxo)silane(Si(ᵗOctNCH=CHNᵗOct)(OCHMeCH₂OMe)₂), (N,N'-diisopropyl-1,2-vinylenediamide-κ²N,N')bis(1,1-dimethyl-2-methoxyethyloxo)silane(Si(ⁱPrNCH=CHNⁱPr)(OCMe₂CH₂OMe)₂), (N,N'-di-tert-butyl-1,2-vinylenediamide-κ²N,N')bis(1,1-dimethyl-2-methoxyethyloxo)silane(Si(ᵗBuNCH=CHNᵗBu)(OCMe₂CH₂OMe)₂), (N,N'-di-tert-pentyl-1,2-vinylenediamide-κ²N,N')bis(1,1-dimethyl-2-methoxyethyloxo)silane(Si(PeNCH=CHNᵗPe)(OCMe₂CH₂OMe)₂), (N,N'-bis(1,1,3,3-tetramethylbutyl)-1,2-vinylenediamide-κ²N,N')bis(1,1-dimethyl-2-methoxyethyloxo)silane(Si(ᵗOctNCH=CHNᵗOct)(OCMe₂CH₂OMe)₂), (N,N'-diisopropyl-1,2-vinylenediamide-κ²N,N')bis(3-methoxypropyloxo)silane(Si(ⁱPrNCH=CHNⁱPr)(OCH₂CH₂CH₂OMe)₂), (N,N'-di-tert-butyl-1,2-vinylenediamide-κ²N,N')bis(3-methoxypropyloxo)silane(Si(ᵗBuNCH=CHNᵗBu)(OCH₂CH₂CH₂OMe)₂), (N,N'-di-tert-pentyl-1,2-vinylenediamide-κ²N,N')bis(3-methoxypropyloxo)silane(Si(ᵗPeNCH=CHNᵗPe)(OCH₂CH₂CH₂OMe)₂), (N,N'-bis(1,1,3,3-tetramethylbutyl)-1,2-vinylenediamide-κ²N,N')bis(3-methoxypropyloxo)silane(Si(ᵗOctNCH=CHNᵗOct)(OCH₂CH₂CH₂OMe)₂), (N,N'-diisopropyl-1,2-vinylenediamide-κ²N,N')bis(1-ethyl-2-methoxyethyloxo)silane(Si(ⁱPrNCH=CHNⁱPr)(OCHEtCH₂OMe)₂), (N,N'-di-tert-butyl-1,2-vinylenediamide-κ²N,N')bis(1-ethyl-2-methoxyethyloxo)silane(Si(ᵗBuNCH=CHNᵗBu)(OCHEtCH₂OMe)₂), (N,N'-di-tert-pentyl-1,2-vinylenediamide-κ²N,N')bis(1-ethyl-2-methoxyethyloxo)silane(Si(ᵗPeNCH=CHNᵗPe)(OCHEtCH₂OMe)₂), (N,N'-bis(1,1,3,3-tetramethylbutyl)-1,2-vinylenediamide-κ²N,N')bis(1-ethyl-2-methoxyethyloxo)silane(Si(ᵗOctNCH=CHNᵗOct)(OCHEtCH₂OMe)₂), (N,N'-diisopropyl-1,2-vinylenediamide-κ²N,N')bis(2-methoxypropyloxo)silane(Si(ⁱPrNCH=CHNⁱPr)(OCH₂CH(OMe)CH₃)₂), (N,N'-di-tert-butyl-1,2-vinylenediamide-κ²N,N')bis(2-methoxypropyloxo)silane(Si(ᵗBuNCH=CHNᵗBu)(OCH₂CH(OMe)CH₃)₂), (N,N'-di-tert-pentyl-1,2-vinylenediamide-κ²N,N')bis(2-methoxypropyloxo)silane(Si(ᵗPeNCH=CHNᵗPe)(OCH₂CH(OMe)CH₃)₂), (N,N'-bis(1,1,3,3-tetramethylbutyl)-1,2-vinylenediamide-κ²N,N')bis(2-methoxypropyloxo)silane(Si(ᵗOctNCH=CHNᵗOct)(OCH₂CH(OMe)CH₃)₂), (N,N'-diisopropyl-1,2-vinylenediamide-κ²N,N')bis(2-methoxybutyloxo)silane(Si(ⁱPrNCH=CHNⁱPr)(OCH₂CH(OMe)CH₂CH₃)₂), (N,N'-di-tert-butyl-1,2-vinylenediamide-κ²N,N')bis(2-methoxybutyloxo)silane(Si(ᵗBuNCH=CHNᵗBu)(OCH₂CH(OMe)CH₂CH₃)₂), (N,N'-di-tert-pentyl-1,2-vinylenediamide-κ²N,N')bis(2-methoxybutyloxo)silane(Si(ᵗPeNCH=CHNᵗPe)(OCH₂CH(OMe)CH₂CH₃)₂), (N,N'-bis(1,1,3,3-tetramethylbutyl)-1,2-vinylenediamide-κ²N,N')bis(2-methoxybutyloxo)silane(Si(ᵗOctNCH=CHNᵗOct)(OCH₂CH(OMe)CH₂CH₃)₂), (N,N'-diisopropyl-1,2-vinylenediamide-κ²N,N')bis(2-(diethylamino)ethyloxo)silane(Si(ⁱPrNCH=CHNⁱPr)(OCH₂CH₂NEt₂)₂), (N,N'-di-tert-butyl-1,2-vinylenediamide-κ²N,N')bis(2-(diethylamino)ethyloxo)silane(Si(ᵗBuNCH=CHNᵗBu)(OCH₂CH₂NEt₂)₂), (N,N'-di-tert-pentyl-1,2-vinylenediamide-κ²N,N')bis(2-(diethylamino)ethyloxo)silane(Si(ᵗPeNCH=CHNᵗPe)(OCH₂CH₂NEt₂)₂), (N,N'-bis(1,1,3,3-tetramethylbutyl)-1,2-vinylenediamide-κ²N,N')bis(2-(diethylamino)ethyloxo)silane(Si(ᵗOctNCH=CHNᵗOct)(OCH₂CH₂NEt₂)₂), (N,N'-diisopropyl-1,2-vinylenediamide-κ²N,N')bis(2-(dimethylamino)ethyloxo)silane(Si(ⁱPrNCH=CHNⁱPr)(OCH₂CH₂NMe₂)₂), (N,N'-di-tert-butyl-1,2-vinylenediamide-κ²N,N')bis(2-(dimethylamino)ethyloxo)silane(Si(ᵗBuNCH=CHNᵗBu)(OCH₂CH₂NMe₂)₂), (N,N'-di-tert-pentyl-1,2-vinylenediamide-κ²N,N')bis(2-(dimethylamino)ethyloxo)silane(Si(ᵗPeNCH=CHNᵗPe)(OCH₂CH₂NMe₂)₂), (N,N'-bis(1,1,3,3-tetramethylbutyl)-1,2-vinylenediamide-κ²N,N')bis(2-(dimethylamino)ethyloxo)silane(Si(ᵗOctNCH=CHNᵗOct)(OCH₂CH₂NMe₂)₂), (N,N'-diisopropyl-1,2-vinylenediamide-κ²N,N')bis(2-(diethylamino)propyloxo)silane(Si(ⁱPrNCH=CHNⁱPr)(OCH₂CH₂CH₂NEt₂)₂), (N,N'-di-tert-butyl-1,2-vinylenediamide-κ²N,N')bis(2-(diethylamino)propyloxo)silane(Si(ᵗBuNCH=CHNᵗBu)(OCH₂CH₂CH₂NEt₂)₂), (N,N'-di-tert-pentyl-1,2-vinylenediamide-κ²N,N')bis(2-(diethylamino)propyloxo)silane(Si(ᵗPeNCH=CHNᵗPe)(OCH₂CH₂CH₂NEt₂)₂), (N,N'-bis(1,1,3,3-tetramethylbutyl)-1,2-vinylenediamide-κ²N,N')bis(2-(diethylamino)propyloxo)silane(Si(ᵗOctNCH=CHNᵗOct)(OCH₂CH₂CH₂NEt₂)₂), (N,N'-diisopropyl-1,2-vinylenediamide-κ²N,N')bis(2-(dimethylamino)propyloxo)silane(Si(ⁱPrNCH=CHNⁱPr)(OCH₂CH₂CH₂NMe₂)₂), (N,N'-di-tert-butyl-1,2-vinylenediamide-κ²N,N')bis(2-(dimethylamino)propyloxo)silane(Si(ᵗBuNCH=CHNᵗBu)(OCH₂CH₂CH₂NMe₂)₂), (N,N'-di-tert-pentyl-1,2-vinylenediamide-κ²N,N')bis(2-(dimethylamino)propyloxo)silane(Si(ᵗPeNCH=CHNᵗPe)(OCH₂CH₂CH₂NMe₂)₂), and (N,N'-bis(1,1,3,3-tetramethylbutyl)-1,2-vinylenediamide-κ²N,N')bis(2-(dimethylamino)propyloxo)silane(Si(ᵗOctNCH=CHNᴸOct)(OCH₂CH₂CH₂NMe₂)₂).

Among these, preferred are Ti(ⁱPrNCH=CHNⁱPr)(OCH₂CH₂OMe)₂, Ti(ᵗBuNCH=CHNᵗBu)(OCH₂CH₂OMe)₂, Ti(ᵗPeNCH=CHNᵗPe)(OCH₂CH₂OMe)₂), Ti(ᵗOctNCH=CHNᵗOct)(OCH₂CH₂OMe)₂, Ti(ⁱPrNCH=CHNⁱPr)(OCH₂CH₂OEt)₂, Ti(ᵗBuNCH=CHNᵗBu)(OCH₂CH₂OEt)₂, Ti(ᵗPeNCH=CHNᵗPe)(OCH₂CH₂OEt)₂, Ti(ᵗOctNCH=CHNᵗOct)(OCH₂CH₂OEt)₂, Ti(ⁱPrNCH=CHNⁱPr)(OCH₂CH₂OPr)₂, Ti(ᵗBuNCH=CHNᵗBu)(OCH₂CH₂OPr)₂, Ti(ᵗPeNCH=CHNᵗPe)(OCH₂CH₂OPr)₂, Ti(ᵗOctNCH=CHNᵗOct)(OCH₂CH₂OPr)₂, Ti(ⁱPrNCH=CHNⁱPr)(OCH₂CH₂OⁱPr)₂, Ti(ᵗBuNCH=CHNᵗBu)(OCH₂CH₂Oⁱpr)₂, Ti(ᵗPeNCH=CHNᵗPe)(OCH₂CH₂Oⁱpr)₂, Ti(ᵗOctNCH=CHNᵗOct)(OCH₂CH₂Oⁱpr)₂, Ti(ⁱPrNCH=CHNⁱPr)(OCH₂CH₂OᵗBu)₂, Ti(ᵗBuNCH=CHNᵗBu)(OCH₂CH₂OᵗBu)₂, Ti(ᵗPeNCH=CHNᵗPe)(OCH₂CH₂OᵗBu)₂, Ti(ᵗOctNCH=CHNᵗOct)(OCH₂CH₂OᵗBu)₂, Ti(ⁱPrNCH=CHNⁱPr)(OCHMeCH₂OMe)₂, Ti(ᵗBuNCH=CHNᵗBu)(OCHMeCH₂OMe)₂, Ti(ᵗPeNCH=CHNᵗPe)(OCHMeCH₂OMe)₂, Ti(ᵗOctNCH=CHNᵗOct)(OCHMeCH₂OMe)₂, Ti(ⁱPrNCH=CHNⁱPr)(OCMe₂CH₂OMe)₂, Ti(ᵗBuNCH=CHNᵗBu)(OCMe₂CH₂OMe)₂, Ti(ᵗPeNCH=CHNᵗPe)(OCMe₂CH₂OMe)₂, Ti(ᵗOctNCH=CHNᵗOct)(OCMe₂CH₂OMe)₂, Ti(ⁱPrNCH=CHNⁱPr)(OCH₂CH₂CH₂OMe)₂, Ti(ᵗBuNCH=CHNᵗBu)(OCH₂CH₂CH₂OMe)₂, Ti(ᵗPeNCH=CHNᵗPe)(OCH₂CH₂CH₂OMe)₂, Ti(ᵗOctNCH=CHNᵗOct)(OCH₂CH₂CH₂OMe)₂, Ti(ⁱPrNCH=CHNⁱPr)(OCH₂CH₂NEt₂)₂, Ti(ᵗBuNCH=CHNᵗBu)(OCH₂CH₂NEt₂)₂, Ti(ᵗPeNCH=CHNᵗPe)(OCH₂CH₂NEt₂)₂, Ti(OctNCH=CHNᵗOct)(OCH₂CH₂NEt₂)₂, Ti(ⁱPrNCH=CHNⁱPr)(OCH₂CH₂NMe₂)₂, Ti(ᵗBuNCH=CHNᵗBu)(OCH₂CH₂NMe₂)₂, Ti(ᵗPeNCH=CHNᵗPe)(OCH₂CH₂NMe₂)₂, Ti(ᵗOctNCH=CHNᵗOct)(OCH₂CH₂NMe₂)₂, Si(ⁱPrNCH=CHNⁱPr)(OCH₂CH₂OMe)₂, Si(ᵗBuNCH=CHNᵗBu)(OCH₂CH₂OMe)₂, Si(ᵗPeNCH=CHNᵗPe)(OCH₂CH₂OMe)₂), Si(ᵗOctNCH=CHNᵗOct)(OCH₂CH₂OMe)₂, Si(ⁱPrNCH=CHNⁱPr)(OCH₂CH₂OEt)₂, Si(ᵗBuNCH=CHNᵗBu)(OCH₂CH₂OEt)₂, Si(PeNCH=CHNᵗPe)(OCH₂CH₂OEt)₂, Si(ᵗOctNCH=CHNᵗOct)(OCH₂CH₂OEt)₂, Si(ⁱPrNCH=CHNⁱPr)(OCH₂CH₂OPr)₂, Si(ᵗBuNCH=CHNᵗBu)(OCH₂CH₂OPr)₂, Si(PeNCH=CHNᵗPe)(OCH₂CH₂OPr)₂, Si(ᵗOctNCH=CHNᵗOct)(OCH₂CH₂OPr)₂, Si(ⁱPrNCH=CHNⁱPr)(OCH₂CH₂Oⁱpr)₂, Si(BuNCH=CHNᵗBu)(OCH₂CH₂Oⁱpr)₂, Si(ᵗPeNCH=CHNᵗPe)(OCH₂CH₂Oⁱpr)₂, Si(ᵗOctNCH=CHNᵗOct)(OCH₂CH₂Oⁱpr)₂, Si(ⁱPrNCH=CHNⁱPr)(OCH₂CH₂OᵗBu)₂, Si(ᵗBuNCH=CHNᵗBu)(OCH₂CH₂OᵗBu)₂, Si(ᵗPeNCH=CHNᵗPe)(OCH₂CH₂OᵗBu)₂, Si(ⁱPrNCH=CHNⁱPr)(OCH₂CH₂CH₂OMe)₂, Si(ᵗBuNCH=CHNᵗBu)(OCH₂CH₂CH₂OMe)₂, Si(ᵗPeNCH=CHNᵗPe)(OCH₂CH₂CH₂OMe)₂, Si(ᵗOctNCH=CHNᵗOct)(OCH₂CH₂CH₂OMe)₂, Si(ⁱPrNCH=CHNⁱPr)(OCH₂CH₂NEt₂)₂, Si(ᵗBuNCH=CHNᵗBu)(OCH₂CH₂NEt₂)₂, Si(ᵗPeNCH=CHNᵗPe)(OCH₂CH₂NEt₂)₂, Si(ᵗOctNCH=CHNᵗOct)(OCH₂CH₂NEt₂)₂, Si(ⁱPrNCH=CHNⁱPr)(OCH₂CH₂NMe₂)₂, Si(ᵗBuNCH=CHNᵗBu)(OCH₂CH₂NMe₂)₂, Si(ᵗPeNCH=CHNᵗPe)(OCH₂CH₂NMe₂)₂, Si(ᵗOctNCH=CHNᵗOct)(OCH₂CH₂NMe₂)₂, and the like, and more preferred are Ti(ⁱPrNCH=CHNⁱPr)(OCH₂CH₂OMe)₂, Ti(ᵗBuNCH=CHNᵗBu)(OCH₂CH₂OMe)₂, Ti(ᵗPeNCH=CHNᵗPe)(OCH₂CH₂OMe)₂), Ti(ⁱPrNCH=CHNⁱPr)(OCH₂CH₂OEt)₂, Ti(ᵗBuNCH=CHNᵗBu)(OCH₂CH₂OEt)₂, Ti(ᵗPeNCH=CHNᵗPe)(OCH₂CH₂OEt)₂, Ti(ᵗBuNCH=CHNᵗBu)(OCH₂CH₂OPr)₂, Ti(ᵗPeNCH=CHNᵗPe)(OCH₂CH₂OPr)₂, Ti(ⁱPrNCH=CHNⁱPr)(OCH₂CH₂Oⁱpr)₂, Ti(ᵗBuNCH=CHNᵗBu)(OCH₂CH₂Oⁱpr)₂, Ti(ᵗPeNCH=CHNᵗPe)(OCH₂CH₂Oⁱpr)₂, Ti(ⁱPrNCH=CHNⁱPr)(OCH₂CH₂OᵗBu)₂, Ti(ᵗBuNCH=CHNᵗBu)(OCH₂CH₂OᵗBu)₂, Ti(ᵗPeNCH=CHNᵗPe)(OCH₂CH₂OᵗBu)₂, Ti(ⁱPrNCH=CHNⁱPr)(OCHMeCH₂OMe)₂, Ti(ᵗBuNCH=CHNᵗBu)(OCHMeCH₂OMe)₂, Ti(ᵗPeNCH=CHNᵗPe)(OCHMeCH₂OMe)₂, Ti(ⁱPrNCH=CHNⁱPr)(OCMe₂CH₂OMe)₂, Ti(ᵗBuNCH=CHNᵗBu)(OCMe₂CH₂OMe)₂, Ti(ᵗPeNCH=CHNᵗPe)(OCMe₂CH₂OMe)₂, Ti(ⁱPrNCH=CHNⁱPr)(OCH₂CH₂CH₂OMe)₂, Ti(ᵗBuNCH=CHNᵗBu)(OCH₂CH₂CH₂OMe)₂, Ti(ᵗPeNCH=CHNᵗPe)(OCH₂CH₂CH₂OMe)₂, Ti(ⁱPrNCH=CHNⁱPr)(OCH₂CH₂NEt₂)₂, Ti($^t$BuNCH=CHN$^t$Bu)(OCH$_2$CH$_2$NEt$_2$)$_2$,
Ti($^t$PeNCH=CHN$^t$Pe)(OCH$_2$CH$_2$NEt$_2$)$_2$,
Ti($^i$PrNCH=CHN$^i$Pr)(OCH$_2$CH$_2$NMe$_2$)$_2$,
Ti($^t$BuNCH=CHN$^t$Bu)(OCH$_2$CH$_2$NMe$_2$)$_2$,
Ti($^t$PeNCH=CHN$^t$Pe)(OCH$_2$CH$_2$NMe$_2$)$_2$,
Si($^i$PrNCH=CHN$^i$Pr)(OCH$_2$CH$_2$OMe)$_2$,
Si($^t$BuNCH=CHN$^t$Bu)(OCH$_2$CH$_2$OMe)$_2$,
Si($^t$PeNCH=CHN$^t$Pe)(OCH$_2$CH$_2$OMe)$_2$),
Si($^i$PrNCH=CHN$^i$Pr)(OCH$_2$CH$_2$OEt)$_2$,
Si($^t$BuNCH=CHN$^t$Bu)(OCH$_2$CH$_2$OEt)$_2$,
Si($^t$PeNCH=CHN$^t$Pe)(OCH$_2$CH$_2$OEt)$_2$,
Si($^i$PrNCH=CHN$^i$Pr)(OCH$_2$CH$_2$OPr)$_2$,
Si($^t$BuNCH=CHN$^t$Bu)(OCH$_2$CH$_2$OPr)$_2$,
Si($^t$PeNCH=CHN$^t$Pe)(OCH$_2$CH$_2$OPr)$_2$,
Si($^i$PrNCH=CHN$^i$Pr)(OCH$_2$CH$_2$O$^i$Pr)$_2$,
Si($^t$BuNCH=CHN$^t$Bu)(OCH$_2$CH$_2$O$^i$Pr)$_2$,
Si($^t$PeNCH=CHN$^t$Pe)(OCH$_2$CH$_2$O$^i$Pr)$_2$,
Si($^i$PrNCH=CHN$^i$Pr)(OCH$_2$CH$_2$O$^t$Bu)$_2$,
Si($^t$BuNCH=CHN$^t$Bu)(OCH$_2$CH$_2$O$^t$Bu)$_2$,
Si($^t$PeNCH=CHN$^t$Pe)(OCH$_2$CH$_2$O$^t$Bu)$_2$,
Si($^i$PrNCH=CHN$^i$Pr)(OCH$_2$CH$_2$CH$_2$OMe)$_2$,
Si($^t$BuNCH=CHN$^t$Bu)(OCH$_2$CH$_2$CH$_2$OMe)$_2$,
Si($^t$PeNCH=CHN$^t$Pe)(OCH$_2$CH$_2$CH$_2$OMe)$_2$, and the like ($^t$Oct indicates a 1,1,3,3-tetramethylbutyl group).

The production method for the vinylenediamide complex (2) is described. The production method 3 is a method of reacting a tetraalkoxide (3) and a vinylenediamide alkali metal salt (4), which are shown in the formulae below, to produce the vinylenediamide complex (2).

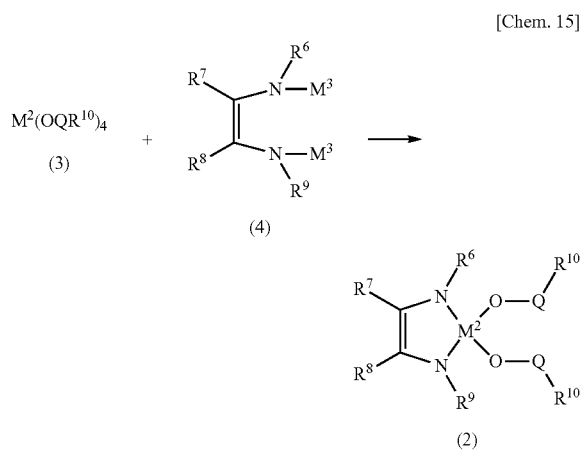

[Chem. 15]

(wherein R$^6$ to R$^{10}$, Q and M$^2$ in formula (3) or (4) have the same meanings as R$^6$ to R$^{10}$, Q and M$^2$ in formula (2), and M$^3$ represents an alkali metal atom).

As for the tetraalkoxide (3) used in the production method 3, a commercial product may be used as it is. Also, a tetraalkoxide (3) produced in accordance with the method described, for example, in known literatures such as D.C. Bradley et al., Alkoxo and Aryloxo Derivatives of Metals, first edition, ACADEMIC PRESS, pp. 4-51 (2001), may be used.

Specific examples of the tetraalkoxide (3) include tetrakis(2-methoxyethyloxo)titanium(Ti(OCH$_2$CH$_2$OMe)$_4$), tetrakis(2-ethoxyethyloxo)titanium(Ti(OCH$_2$CH$_2$OEt)$_4$), tetrakis(2-propoxyethyloxo)titanium(Ti(OCH$_2$CH$_2$OPr)$_4$), tetrakis(2-isopropoxyethyloxo)titanium(Ti(OCH$_2$CH$_2$O$^i$Pr)$_4$), tetrakis(2-tert-butoxyethyloxo)titanium(OCH$_2$CH$_2$O$^t$Bu)$_4$), tetrakis(1-methyl-2-methoxyethyloxo)titanium(Ti(OCHMeCH$_2$OMe)$_4$), tetrakis(1,1-dimethyl-2-methoxyethyloxo)titanium(Ti(OCMe$_2$CH$_2$OMe)$_4$), tetrakis(3-methoxypropyloxo)titanium(Ti(OCH$_2$CH$_2$CH$_2$OMe)$_4$), tetrakis(1-ethyl-2-methoxyethyloxo)titanium(Ti(OCHEtCH$_2$OMe)$_4$), tetrakis(2-methoxypropyloxo)titanium (Ti(OCH$_2$CH(OMe)CH$_3$)$_4$), tetrakis(2-methoxybutyloxo)titanium(Ti(OCH$_2$CH(OMe)CH$_2$CH$_3$)$_4$), tetrakis(2-(diethylamino)ethyloxo)titanium(Ti(OCH$_2$CH$_2$NEt$_2$)$_4$), tetrakis(2-(dimethylamino)ethyloxo)titanium(Ti(OCH$_2$CH$_2$NMe$_2$)$_4$), tetrakis(2-(diethylamino)propyloxo)titanium(Ti(OCH$_2$CH$_2$CH$_2$NEt$_2$)$_4$), tetrakis(2-(dimethylamino)propyloxo)titanium(Ti(OCH$_2$CH$_2$CH$_2$NMe$_2$)$_4$), tetrakis(2-methoxyethyloxy)silane(Si(OCH$_2$CH$_2$OMe)$_4$), tetrakis(2-ethoxyethyloxy)silane(Si(OCH$_2$CH$_2$OEt)$_4$), tetrakis(2-propoxyethyloxy)silane(Si(OCH$_2$CH$_2$OPr)$_4$), tetrakis(2-isopropoxyethyloxy)silane(Si(OCH$_2$CH$_2$O$^i$Pr)$_4$), tetrakis(2-tert-butoxyethyloxy)silane(OCH$_2$CH$_2$O$^t$Bu)$_4$), tetrakis(1-methyl-2-methoxyethyloxy)silane(Si(OCHMeCH$_2$OMe)$_4$), tetrakis(1,1-dimethyl-2-methoxyethyloxy)silane(Si(OCMe$_2$CH$_2$OMe)$_4$), tetrakis(3-methoxypropyloxy)silane(Si(OCH$_2$CH$_2$CH$_2$OMe)$_4$), tetrakis(1-ethyl-2-methoxyethyloxy)silane(Si(OCHEtCH$_2$OMe)$_4$), tetrakis(2-methoxypropyloxy)silane(Si(OCH$_2$CH(OMe)CH$_3$)$_4$), tetrakis(2-methoxybutyloxy)silane(Si(OCH$_2$CH(OMe)CH$_2$CH$_3$)$_4$), tetrakis(2-(diethylamino)ethyloxy)silane (Si(OCH$_2$CH$_2$NEt$_2$)$_4$), tetrakis(2-(dimethylamino)ethyloxy)silane(Si(OCH$_2$CH$_2$NMe$_2$)$_4$), tetrakis(2-(diethylamino)propyloxy)silane(Si(OCH$_2$CH$_2$CH$_2$NEt$_2$)$_4$), and tetrakis(2-(dimethylamino)propyloxy)silane(Si(OCH$_2$CH$_2$CH$_2$NMe$_2$)$_4$). Among these, preferred are Ti(OCH$_2$CH$_2$OMe)$_4$, Ti(OCH$_2$CH$_2$OEt)$_4$, Ti(OCH$_2$CH$_2$OPr)$_4$, Ti(OCH$_2$CH$_2$O$^i$Pr)$_4$, Ti(OCH$_2$CH$_2$O$^t$Bu)$_4$), Ti(OCHMeCH$_2$OMe)$_4$, Ti(OCMe$_2$CH$_2$OMe)$_4$, Ti(OCH$_2$CH$_2$CH$_2$OMe)$_4$, Ti(OCH$_2$CH(OMe)CH$_3$)$_4$, Ti(OCH$_2$CH$_2$NEt$_2$)$_4$, Ti(OCH$_2$CH$_2$NMe$_2$)$_4$, Si(OCH$_2$CH$_2$OMe)$_4$, Si(OCH$_2$CH$_2$OEt)$_4$, Si(OCH$_2$CH$_2$OPr)$_4$, Si(OCH$_2$CH$_2$O$^i$Pr)$_4$, Si(OCH$_2$CH$_2$O$^t$Bu)$_4$, Si(OCH$_2$CH$_2$CH$_2$OMe)$_4$), Si(OCH$_2$CH$_2$NEt$_2$)$_4$, Si(OCH$_2$CH$_2$NMe$_2$)$_4$, and the like.

The vinylenediamide alkali metal salt (4) and the N,N'-dialkyl-1,4-diaza-1,3-butadiene (R$^1$N=CR$^2$CR$^3$=NR$^4$) as a synthesis raw material thereof may be produced in accordance with the method described, for example, in Journal of the American Chemical Society, Vol. 120, page 12714 (1998) or Journal of Organometallic Chemistry, Vol. 301, page 183 (1986). Examples of the alkali metal M$^3$ include a lithium atom, a sodium atom, and a potassium atom. In terms of good yield of the vinylenediamide complex (2), M$^3$ is preferably a lithium atom or a sodium atom, more preferably a lithium atom.

Specific examples of the vinylenediamide alkali metal salt (4) include (N,N'-diisopropyl-1,2-vinylenediamide)dilithium, (N,N'-di-isopropyl-1,2-vinylenediamide)disodium, (N,N'-di-isopropyl-1,2-vinylenediamide)dipotassium, (N,N'-di-tert-butyl-1,2-vinylenediamide)dilithium, (N,N'-di-tert-butyl-1,2-vinylenediamide)disodium, (N,N'-di-tert-butyl-1,2-vinylenediamide)dipotassium, (N,N'-di-tert-pentyl-1,2-vinylenediamide)dilithium, (N,N'-di-tert-pentyl-1,2-vinylenediamide)disodium, (N,N'-di-tert-pentyl-1,2-vinylenediamide)dipotassium, (N,N'-bis(1,1,3,3-tetramethylbutyl)-1,2-vinylenediamide)dilithium, (N,N'-bis(1,1,3,3-tetramethylbutyl)-1,2-vinylenediamide)disodium, and (N,N'-bis(1,1,3,3-tetramethylbutyl)-1,2-vinylenediamide)dipotassium. Among these, preferred are (N,N'-di-tert-butyl-1,2-vinylenediamide)dilithium, (N,N'-di-tert-pentyl-1,2-vinylenediamide)dilithium, (N,N'-bis(1,1,3,3-tetramethylbutyl)-1,2-vinylenediamide)dilithium, and the like.

The production method 3 is preferably performed in an inert gas atmosphere in terms of good yield of the vinylenediamide complex (2). Examples of the inert gas include nitrogen, helium, neon, and argon. In terms of good yield of the vinylenediamide complex (2), the production method 3 is preferably performed in a nitrogen or argon atmosphere.

Also, the production method 3 is preferably performed in an organic solvent in terms of good yield of the vinylenediamide complex (2). The organic solvent which can be used is not limited as long as it is an organic solvent not inhibiting the reaction. Examples of the solvent which can be used include a hydrocarbon solvent such as pentane, hexane, heptane, octane, cyclohexane, methylcyclohexane, ethylcyclohexane, benzene, toluene, xylene and ethylbenzene, and an ether solvent such as diethyl ether, diisopropyl ether, cyclopentyl methyl ether, cyclopentyl ethyl ether, dioxane, tetrahydrofuran, ethylene glycol dimethyl ether and ethylene glycol diethyl ether. One of these may be used alone, or two or more kinds thereof may be mixed at an arbitrary ratio and used. In terms of good yield of the vinylenediamide complex (2), it is also preferred to use a mixture of an ether solvent such as tetrahydrofuran, diisopropyl ether and cyclopentyl methyl ether and a hydrocarbon solvent such as hexane and heptane. In the production method 3, the amount of the solvent used is not particularly limited, and the vinylenediamide complex (2) can be produced in good yield by using an appropriately selected amount of solvent.

The molar ratio between the tetraalkoxide (3) and the vinylenediamide alkali metal salt (4) is not limited and in terms of good conversion rate of tetraalkoxide, the molar ratio of tetraalkoxide (3):vinylenediamide alkali metal salt (4) is preferably from 1:1 to 1:1.5.

The reaction temperature and reaction time in the production method 3 are not particularly limited and are appropriately selected from the ranges of preferably from −80° C. to 200° C. and from 10 minutes to 120 hours, more preferably from −20° C. to 120° C. and from 1 to 48 hours, whereby the vinylenediamide complex (2) can be produced in good yield.

The vinylenediamide complex (2) produced by the production method 3 may be purified, if desired, by appropriately selecting and using a general purification method such as filtration, extraction, distillation, sublimation and crystallization.

The production method 4 is described below. The production method 4 is a method of reacting a bis(dialkylamide) titanium complex (5) and an alcohol (6), which are shown in the formulae below, to produce a vinylenediamide titanium complex (2-Ti) where $M^2$ in formula (2) is a titanium atom.

[Chem. 16]

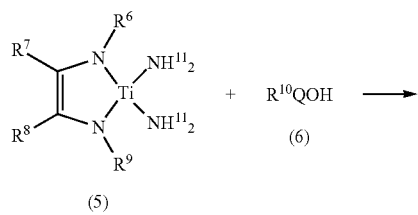

(5)

+ $R^{10}QOH$ (6)

⟶

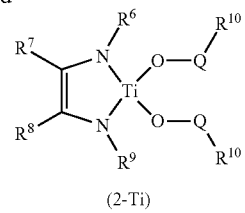

(2-Ti)

(wherein $R^6$ to $R^9$ in formula (5) and $R^{10}$ and Q in formula (6) have the same meanings as $R^6$ to $R^{10}$ and Q in formula (2), and $R^{11}$ represents a $C_1$-$C_6$ alkyl group).

The bis(dialkylamide)titanium complex (5) can be produced in accordance with the methods described in JP-A-2007-153872 and JP-A-2011-88851. The definition of $R^{11}$ is described. The alkyl group with a carbon number of $C_1$-$C_6$ represented by $R^{11}$ may be any of linear, branched and cyclic alkyl groups, and examples thereof include a methyl group, an ethyl group, a propyl group, an isopropyl group, a cyclopropyl group, a butyl group, an isobutyl group, a sec-butyl group, a tert-butyl group, a cyclobutyl group, a tert-pentyl group, a cyclopentyl group, a cyclohexyl group, and a 1,3-dimethylbutyl group. In terms of good yield of the vinylenediamide titanium complex (2-Ti), a methyl group or an ethyl group is preferred.

Specific examples of the bis(dialkylamide) complex represented by formula (5) include (N,N'-diisopropyl-1,2-vinylenediamide-$\kappa^2$N,N')bis(dimethylamide)titanium(Ti($^i$PrNCH=CHN$^i$Pr)(NMe$_2$)$_2$), (N,N'-di-tert-butyl-1,2-vinylenediamide-$\kappa^2$N,N')bis(dimethylamide)titanium(Ti($^t$BuNCH=CHN$^t$Bu)(NMe$_2$)$_2$), (N,N'-di-tert-pentyl-1,2-vinylenediamide-$\kappa^2$N,N')bis(dimethylamide)titanium(Ti($^t$PeNCH=CHN$^t$Pe)(NMe$_2$)$_2$), (N,N'-bis(1,1,3,3-tetramethylbutyl)-1,2-vinylenediamide-$\kappa^2$N,N')bis(dimethyl amide)titanium(Ti($^t$OctNCH=CHN$^t$Oct)(NMe$_2$)$_2$), (N,N'-diisopropyl-1,2-vinylenediamide-$\kappa^2$N,N')bis(diethylamide)titanium(Ti($^i$PrNCH=CHN$^i$Pr)(NEt$_2$)$_2$), (N,N'-di-tert-butyl-1,2-vinylenediamide-$\kappa^2$N,N')bis(diethylamide)titanium(Ti($^t$BuNCH=CHN$^t$Bu)(NEt$_2$)$_2$), (N,N'-di-tert-pentyl-1,2-vinylenediamide-$\kappa^2$N,N')bis(diethylamide)titanium(Ti($^t$PeNCH=CHN$^t$Pe)(NEt$_2$)$_2$), (N,N'-bis(1,1,3,3-tetramethylbutyl)-1,2-vinylenediamide-$\kappa^2$N,N')bis(diethylamide)titanium(Ti($^t$OctNCH=CHN$^t$Oct)(NEt$_2$)$_2$), (N,N'-diisopropyl-1,2-vinylenediamide-$\kappa^2$N,N')bis(ethylmethylamide)titanium(Ti($^i$PrNCH=CHN$^i$Pr)(NEtMe)$_2$), (N,N'-di-tert-butyl-1,2-vinylenediamide-$\kappa^2$N,N')bis(ethylmethylamide)titanium(Ti($^t$BuNCH=CHN$^t$Bu)(NEtMe)$_2$), (N,N'-di-tert-pentyl-1,2-vinylenediamide-$\kappa^2$N,N')bis(ethylmethylamide)titanium(Ti($^t$PeNCH=CHN$^t$Pe)(NEtMe)$_2$), (N,N'-bis(1,1,3,3-tetramethylbutyl)-1,2-vinylenediamide-$\kappa^2$N,N')bis(ethylmethylamide)titanium(Ti($^t$OctNCH=CHN$^t$Oct)(NEtMe)$_2$), (N,N'-diisopropyl-1,2-vinylenediamide-$\kappa^2$N,N')bis(butylmethylamide)titanium(Ti($^i$PrNCH=CHN$^i$Pr)(NBuMe)$_2$), (N,N'-di-tert-butyl-1,2-vinylenediamide-$\kappa^2$N,N')bis(butylmethylamide)titanium(Ti($^t$BuNCH=CHN$^t$Bu)(NBuMe)$_2$), (N,N'-di-tert-pentyl-1,2-vinylenediamide-$\kappa^2$N,N')bis(butylmethylamide)titanium(Ti($^t$PeNCH=CHN$^t$Pe)(NBuMe)$_2$), and (N,N'-bis(1,1,3,3-tetramethylbutyl)-1,2-vinylenediamide-$\kappa^2$N,N')bis(butylmethylamide)titanium(Ti($^t$OctNCH=CHN$^t$Oct)(NBuMe)$_2$). Among these, Ti($^t$BuNCH=CHN$^t$Bu)(NMe$_2$)$_2$, Ti($^t$PeNCH=CHN$^t$Pe)(NMe$_2$)$_2$, Ti($^t$OctNCH=CHN$^t$Oct)(NMe$_2$)$_2$, and the like are preferred.

Examples of the alcohol represented by formula (6) include 2-methoxyethanol, 2-ethoxyethanol, 2-propoxyethanol, 2-isopropoxyethanol, 2-tert-butoxyethanol, 1-methyl-2-methoxyethanol, 3-methoxypropanol, 3-ethoxypropanol, 4-methoxybutanol, 5-methoxypentyl alcohol, 6-methoxyhexyl alcohol, 1-ethyl-2-methoxyethanol, 2-methoxypropanol, 2-methoxybutanol, 3-methoxybutanol, 2-(diethylamino)ethanol, 2-(dimethylamino)ethanol, 2-(diethylamino)propanol, 2-(ethylmethylamino)ethanol, 2-(diisopropylamino)ethanol, 2-(dibutylamino)ethanol, 2-(dipentylamino)ethanol, 2-(dihexylamino)ethanol, 2-(dimethylamino)propanol, 4-dimethylaminobutanol, 5-(dimethylamino)pentyl alcohol, 6-(dimethylamino)hexyl alcohol, 1,1-dimethyl-2-methoxyethanol, 1,1-dimethyl-2-(dimethylamino)ethanol, and 1,1-dimethyl-2-(diethylamino)ethanol. Among these, preferred are 2-methoxyethanol, 2-ethoxyethanol, 2-propoxyethanol, 2-isopropoxyethanol, 2-tert-butoxyethanol, 1-methyl-2-methoxyethanol, 3-methoxypropanol, 3-ethoxypropanol, 1-ethyl-2-methoxyethanol, 2-methoxypropanol, 2-methoxybutanol, 2-(diethylamino)ethanol, 2-(dimethylamino)ethanol, 2-(diethylamino)propanol, 2-(dimethylamino)propanol, 1,1-dimethyl-2-methoxyethanol, 1,1-dimethyl-2-(dimethylamino)ethanol and the like, and more preferred are 2-methoxyethanol, 2-ethoxyethanol, 3-methoxypropanol, 3-ethoxypropanol, 2-(dimethylamino)ethanol, 1,1-dimethyl-2-methoxyethanol, 1,1-dimethyl-2-(dimethylamino)ethanol and the like.

The production method 4 is preferably performed in an inert gas atmosphere in terms of good yield of the vinylenediamide titanium complex (2-Ti). Examples of the inert gas include nitrogen, helium, neon, and argon. In terms of good yield of the vinylenediamide titanium complex (2-Ti), the production method 4 is preferably performed in a nitrogen or argon atmosphere.

Furthermore, the production method 4 is preferably performed in an organic solvent in terms of good yield of the vinylenediamide titanium complex (2-Ti). The organic solvent which can be used is not limited as long as it is an organic solvent not inhibiting the reaction. Examples of the solvent which can be used include a hydrocarbon solvent such as pentane, hexane, heptane, octane, cyclohexane, methylcyclohexane, ethylcyclohexane, benzene, toluene, xylene and ethylbenzene, and an ether solvent such as diethyl ether, diisopropyl ether, cyclopentyl methyl ether, cyclopentyl ethyl ether, dioxane, tetrahydrofuran, ethylene glycol dimethyl ether and ethylene glycol diethyl ether. One of these may be used alone, or two or more kinds thereof may be mixed at an arbitrary ratio and used. In terms of good yield of the vinylenediamide titanium complex (2-Ti), it is also preferred to use a hydrocarbon solvent such as hexane and heptane alone or use a mixture of a hydrocarbon solvent such as hexane and heptane and an ether solvent such as tetrahydrofuran. In the production method 4, the amount of the solvent used is not particularly limited, and the vinylenediamide titanium complex (2-Ti) can be produced in good yield by using an appropriately selected amount of solvent.

In the production method 4, in terms of good yield of the vinylenediamide titanium complex (2-Ti), the bis(dialkylamide)titanium complex (5) and the alcohol (6) are reacted at a molar ratio of preferably from 1:1.8 to 1:2.2, more preferably from 1:1.9 to 1:2.1.

The reaction temperature and reaction time in the production method 4 are not particularly limited and are appropriately selected from the ranges of preferably from −80° C. to 100° C. and from 10 minutes to 120 hours, more preferably from −70° C. to 50° C. and from 1 to 24 hours, whereby the vinylenediamide titanium complex (2-Ti) can be produced in good yield.

The vinylenediamide titanium complex (2-Ti) produced by the production method 4 may be purified, if desired, by appropriately selecting and using a general purification method such as filtration, extraction, distillation, sublimation and crystallization.

The film-forming material of the present invention is a film-forming material obtained by reacting a vinylenediamide complex represented by formula (1) or (2) with one or more kinds of oxidizing agents selected from the group consisting of oxygen gas, air, ozone, water and hydrogen peroxide.

The reaction of the vinylenediamide complex (1) or (2) with an oxidizing agent may be performed either in a solvent or without a solvent. In the case of performing the reaction in a solvent, the solvent used is not limited as long as it is a solvent not harming the reaction, and examples thereof include an alkane-based solvent such as pentane, hexane, cyclohexane, heptane, methylcyclohexane, ethylcyclohexane and octane, a benzene-based solvent such as benzene, toluene, ethylbenzene, xylene and trifluoromethylbenzene, and an ether-based solvent such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran. One kind of these may be used alone, or two or more kinds of solvents may be mixed at an arbitrary ratio and used.

From the standpoint that a Group IV metal oxide film improved in the electrical properties such as electrical conductivity or in the optical properties such as refractive index can be produced, an alkane-based solvent or an ether-based solvent is preferred. The amount of the organic solvent used is not limited and in terms of good time efficiency of the reaction, the solvent is preferably used in an amount of 100 mL or less, more preferably 20 mL or less, per 10 gram of the vinylenediamide complex (1) or (2).

The oxidizing agent which can be used in the production method of the present invention includes oxygen gas, air, ozone, water, and hydrogen peroxide. One kind of these may be used alone, or two ore more kinds may be mixed at an arbitrary ratio and used. In terms of good time efficiency of the reaction with the vinylenediamide complex (1) or (2), oxygen gas, air or water is preferably used.

As for the molar ratio between the vinylenediamide complex (1) or (2) and the oxidizing agent, from the standpoint that a Group IV metal oxide film improved in the electrical properties such as electrical conductivity or in the optical properties such as refractive index can be produced, an equimolar or greater amount of oxidizing agent is preferably reacted with 1 mol of the vinylenediamide complex (1) or (2). In the case where the oxidizing agent is a gas such as oxygen gas or air, it is more preferred to react with oxygen molecule in an amount of 5 molar times or more per mol of the vinylenediamide complex (1) or (2).

At the time of reacting the vinylenediamide complex (1) or (2) with an oxidizing agent, if desired, an inert gas such as helium, neon, argon, krypton, xenon and nitrogen gas may be used as the reaction atmosphere. In the case of using an inert gas, when the oxidizing agent is a gas such as oxygen gas and air, the mixing ratio of the oxidizing agent and the inert gas is not particularly limited, and the volume ratio of oxidizing agent:inert gas is appropriately selected from the range of preferably from 1:99 to 99:1, more preferably from 20:80 to 80:20, whereby a Group IV metal oxide film improved in the electrical properties such as electrical conductivity or in the optical properties such as refractive index can be produced.

The temperature in the reaction of the vinylenediamide complex (1) or (2) with an oxidizing agent is not particularly limited, and the reaction is performed at a temperature appropriately selected according to the kind of the vinylenediamide complex (1) or (2) or the oxidizing agent, whereby a film-forming material can be produced. From the standpoint that a Group IV metal oxide film improved in the electrical properties such as electrical conductivity or in the optical properties such as refractive index can be produced, the reaction temperature is typically from −30° C. to 350° C., preferably from 0 to 120° C., more preferably from 10 to 80° C.

Also, if desired, pyridines such as pyridine, 2-methylpyridine, 3-methylpyridine, 4-methylpyridine and 4-dimethylaminopyridine may be added. In the case of adding pyridines, the amount added thereof is not particularly limited and by using the pyridines in an amount appropriately selected from the range of 0.1 to 50 molar times per mol of the vinylenediamide complex (1) or (2), a Group IV metal oxide film improved in the electrical properties such as electrical conductivity or in the optical properties such as refractive index can be produced.

From the standpoint that a Group IV metal oxide film improved in the electrical properties such as electrical conductivity or in the optical properties such as refractive index can be produced, the film-forming material obtained from the vinylenediamide complex represented by formula (1) or (2) of the present invention is preferably a film-forming material obtained by reacting the vinylenediamide complex (1) or (2) with an oxidizing agent, then dissolving the reaction product in an alcohol containing two or more oxygen atoms in the molecule, and heating the resulting solution.

Examples of the alcohol include cellosolves such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monomethyl ether, propylene glycol monoethyl ether, propylene glycol monopropyl ether, propylene glycol monobutyl ether, 2-dimethylaminoethanol and 2-diethylaminoethanol, diols such as ethylene glycol, 1,3-propanediol, 1,2-butanediol, 1,3-butanediol, 1,4-butanediol, 2,3-butanediol, 1,5-pentanediol, 1,2-hexanediol, 1,5-hexanediol, 1,6-hexanediol, 2,5-hexanediol, 1,7-heptanediol, 1,2-octanediol, 1,8-octanediol, 1,3-nonanediol, 1,9-nonanediol, 1,2-decanediol, 1,10-decanediol, 2,7-dimethyl-3,6-octanediol, 2,2-dibutyl-1,3-propanediol, 1,2-dodecanediol, 1,12-dodecanediol, 1,2-tetradecanediol, 1,14-tetradecanediol, 2,2,4-trimethyl-1,3-pentanediol, 2,4-pentanediol, 1,2-cyclohexanedimethanol, 1,3-cyclohexanedimethanol, 1-hydroxymethyl-2-(2-hydroxyethyl)cyclohexane, 1-hydroxy-2-(3-hydroxypropyl)cyclohexane, 1-hydroxy-2-(2-hydroxyethyl)cyclohexane, 1-hydroxymethyl-2-(2-hydroxyethyl)benzene, 1-hydroxymethyl-2-(3-hydroxypropyl)benzene, 1-hydroxy-2-(2-hydroxyethyl)benzene, 1,2-benzyldimethylol, 1,3-benzyldimethylol, 1,2-cyclohexanediol, 1,3-cyclohexanediol and 1,4-cyclohexanediol, triols such as glycerin, 1,2,6-hexanetriol and 3-methyl-1,3,5-pentanetriol, and tetraols such as 1,3,5,7-cyclooctanetetraol. From the standpoint that an oxide film improved in the electrical properties such as electrical conductivity or in the optical properties such as refractive index can be produced, cellosolves are preferred, and ethylene glycol monomethyl ether is more preferred.

Also, the film-forming material may be film-forming material obtained by dissolving a compound having a titanium atom or a zirconium atom, with the metal atoms being bridged by a bridging oxygen atom, in an alcohol containing two or more oxygen atoms in the molecule and thereafter, heating the solution. In this case, the bridging oxygen atom indicates an oxygen atom coordinated to two, three or four metal atoms by bridge coordination (bridging oxo ligand, triple-bridging oxo ligand and quadruply-bridging oxo ligand). The film-forming material includes, for example, a titanium atom-containing compound such as $Ti_3O(O^iPr)_{10}$, $Ti_3O(OMe)(O^iPr)_9$, $Ti_3O(OH)(O^iPr)_9$, $Ti_3O_2(O^iPr)_9$, $Ti_3O(O^iPr)_7$(dmheot), $Ti_6O_4(OEt)_8(OCOCH_3)_{13}$, $Ti_6O_4(O^iPr)_8(OCOCH_3)_8$, $Ti_6O_4(O^nBu)_8(OCOCH_3)_8$, $Ti_6O_4(O^iPr)_{12}(OCOCH_3)_4Ti_7O_4(OEt)_{20}$, $Ti_8O_6(OCH_2C_6H_5)_{20}$, $Ti_9O_8(O^nPr)_4(OMc)_4$, $Ti_{10}O_8(OEt)_{24}$, $Ti_{11}O_{13}(O^iPr)_{18}$, $Ti_{11}O_{13}(O^iPr)_{13}(OEt)_5$, $Ti_{14}O_{19}(OH)(O^iBu)_{13}(OCOCH_3)_4$, $Ti_{16}O_{16}(OEt)_{32}$, $Ti_{17}O_{24}(O^iPr)_{20}$, $Ti_{18}O_{28}(H)(O^tBu)_{17}$, $Ti_{18}O_{28}(O^tBu)_{16}(^tBuOH)$, $Ti_{18}O_{25}(O^tBu)_{12}(OCOCH_3)_{10}$, $Ti_{18}O_{22}(O^nBu)_{26}(acac)_2$ and $Ti_{28}O_{40}(O^tBu)_{20}(OCOCH_3)_{12}$, and a zirconium atom-containing compound such as $Zr_3O(OH)(O^tBu)_9$, $Zr_3O(O^tBu)_{10}$, $Zr_4O(O^nPr)_{10}(acac)_4$, $Zr_4O_2(OMc)_{12}$, $Zr_6O_4(OH)_4(OMc)_{12}$, $Zr_{10}O_6(OH)_4(O^nPr)_{18}(aaa)_6$ and $Zr_{13}O_8(OMe)_{36}$. Among these, from the standpoint that an oxide film having good optical properties can be produced at a low temperature, $Ti_{10}O_8(OEt)_{24}$, $Ti_{11}O_{13}(O^iPr)_{18}$, $Ti_{11}O_{13}(O^iPr)_{13}$ (OEt)$_5$, $Ti_{14}O_{19}(OH)(O^iBu)_{13}(OCOCH_3)_4$, $Ti_{16}O_{16}(OEt)_{32}$, $Ti_{17}O_{24}(O^iPr)_{20}$, $Ti_{18}O_{28}(H)(O^tBu)_{17}$, $Ti_{18}O_{28}(O^tBu)_{16}(^tBuOH)$, $Ti_8O_{25}(O^tBu)_{12}(OCOCH_3)_{10}$, $Ti_{18}O_{22}(O^nBu)_{26}(acac)_2$, $Ti_{28}O_{40}(O^tBu)_{20}(OCOCH_3)_{12}$, $Zr_6O_4(OH)_4(OMc)_{12}$ and $Zr_{13}O_8(OMe)_{36}$ are preferred. Here, (dmheto) stands for a 2,6-dimethylheptan-3-en-2,4,6-tris(olato) ligand, (OMc) stands for methacrylato ligand, (aaa) stands for oct-7-ene-2,4-dionato ligand ($CH_3COCHCOCH_2CH_2CHCH_2$), and (acac) stands for acetylacetonato ligand.

The alcohol containing two or more oxygen atoms in the molecule includes, for example, the same alcohols as the alcohols used after reacting the vinylenediamide complex (1) or (2) with an oxidizing agent.

The film-forming material solution is characterized by containing the above-described film-forming material and an organic solvent.

The organic solvent that may be contained in the film-forming material solution of the present invention includes alcohols, hydrocarbons, ethers, ketones, carboxylic acid, and esters.

Examples of the alcohols include monools such as methanol, ethanol, propanol, isopropyl alcohol, butanol, sec-butyl alcohol, isobutyl alcohol, tert-butyl alcohol, tert-pentyl alcohol, cyclopentyl alcohol, hexanol, cyclohexyl alcohol and octanol, cellosolves such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monomethyl ether, propylene glycol monoethyl ether, propylene glycol monopropyl ether, propylene glycol monobutyl ether, 2-dimethylaminoethanol and 2-diethylaminoethanol, diols such as ethylene glycol, 1,3-propanediol, 1,2-butanediol, 1,3-butanediol, 1,4-butanediol, 2,3-butanediol, 1,5-pentanediol, 1,2-hexanediol, 1,5-hexanediol, 1,6-hexanediol, 2,5-hexanediol, 1,7-heptanediol, 1,2-octanediol, 1,8-octanediol, 1,3-nonanediol, 1,9-nonanediol, 1,2-decanediol, 1,10-decanediol, 2,7-dimethyl-3,6-octanediol, 2,2-dibutyl-1,3-propanediol, 1,2-dodecanediol, 1,12-dodecanediol, 1,2-tetradecanediol, 1,14-tetradecanediol, 2,2,4-trimethyl-1,3-pentanediol, 2,4-pentanediol, 1,2-cyclohexanedimethanol, 1,3- cyclohexanedimethanol, 1-hydroxymethyl-2-(2-hydroxyethyl)cyclohexane, 1-hydroxy-2-(3-hydroxypropyl)cyclohexane, 1-hydroxy-2-(2-hydroxyethyl)cyclohexane, 1-hydroxymethyl-2-(2-hydroxyethyl)benzene, 1-hydroxymethyl-2-(3-hydroxypropyl)benzene, 1-hydroxy-2-(2-hydroxyethyl)benzene, 1,2-benzyldimethylol, 1,3-benzyldimethylol, 1,2-cyclohexanediol, 1,3-cyclohexanediol and 1,4-cyclohexanediol, triols such as glycerin, 1,2,6-hexanetriol and 3-methyl-1,3,5-pentanetriol, and tetraols such as 1,3,5,7-cyclooctanetetraol.

Examples of the hydrocarbons include pentane, hexane, heptane, octane, nonane, cyclohexane, methylcyclohexane, ethylcyclohexane, benzene, toluene, ethylbenzene, and xylene.

Examples of the ethers include diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane, tetrahydrofuran, 2-methoxyethyl acetate, and 3-methoxypropyl acetate.

Examples of the ketones include acetone, methyl ethyl ketone, diethyl ketone, methyl diisopropyl ketone, tert-butyl methyl ketone, acetylacetone, and diacetyl.

Examples of the carboxylic acid include formic acid, acetic acid, propionic acid, butyric acid, malonic acid, and oxalic acid.

Examples of the esters include a formic acid ester such as methyl formate, ethyl formate, propyl formate and isopropyl formate, an acetic acid ester such as methyl acetate, ethyl acetate, propyl acetate and isopropyl acetate, and a cyclic ester such as γ-butyrolactone.

Also, out of these organic solvents, arbitrary two or more kinds may be mixed at an arbitrary ratio and used.

The organic solvent preferred in terms of good lubricity at the coating on a substrate includes esters and alcohols, and the organic solvent is preferably an acetic acid ester or cellosolves, more preferably ethyl acetate or ethylene glycol monomethyl ether.

In terms of good solubility of the film-forming material, the organic solvent is preferably ethers or ketones, more preferably tetrahydrofuran, γ-butyrolactone or propylene glycol monomethyl acetate.

In the film-forming material solution of the present invention, a leveling agent, a defoaming agent, a thickener, and a modifier such as rheology modifier may be added.

Examples of the leveling agent include a fluorine-containing surfactant, silicone, an organic modified polysiloxane, acrylic resin, methyl acrylate, methyl methacrylate, ethyl acrylate, ethyl methacrylate, propyl acrylate, propyl methacrylate, isopropyl acrylate, isopropyl methacrylate, butyl acrylate, butyl methacrylate, sec-butyl acrylate, sec-butyl methacrylate, isobutyl acrylate, isobutyl methacrylate, tert-butyl acrylate, tert-butyl methacrylate, allyl acrylate, allyl methacrylate, benzyl acrylate, benzyl methacrylate, cyclohexyl acrylate, and cyclohexyl methacrylate.

Examples of the defoaming agent include silicone, a surfactant, a polyether, a higher alcohol, a glycerin higher fatty acid ester, a glycerin acetic acid higher fatty acid ester, a glycerin lactic acid higher fatty acid ester, a glycerin citric acid higher fatty acid ester, a glycerin succinic acid higher fatty acid ester, a glycerin diacetyl tartaric acid higher fatty acid ester, a glycerin acetic acid ester, a polyglycerin higher fatty acid ester, and a polyglycerin condensed ricinoleate.

Examples of the thickener include a polyvinyl alcohol, an acrylic resin, a polyethylene glycol, a polyurethane, a hydrogenated castor oil, an aluminum stearate, a zinc stearate, an aluminum octylate, a fatty acid amide, a polyethylene oxide, a dextrin fatty acid ester, a dibenzylidene sorbitol, a vegetable oil-type polymerized oil, a surface-treated calcium carbonate, an organic bentonite, silica, a hydroxyethyl cellulose, a methyl cellulose, a carboxymethyl cellulose, a sodium alginate, casein, a sodium caseinate, a xanthane gum, a urethane-modified polyether, a poly(acrylic acid-acrylate), and montmorillonite.

Examples of the rheology modifier include an oxidized polyolefin amide, a fatty acid amide type, an oxidized polyolefin type, a urea-modified urethane, methylene diisocyanate, trimethylene diisocyanate, tetramethylene diisocyanate, hexamethylene diisocyanate, ω,ω'-dipropylether diisocyanate, thiodipropyl diisocyanate, cyclohexyl-1,4-diisocyanate, dicyclohexylmethane-4,4'-diisocyanate, 1,5-dimethyl-2,4-bis(isocyanatomethyl)benzene, 1,5-dimethyl-2,4-bis(ω-isocyanatoethyl)benzene, 1,3,5-trimethyl-2,4-bis(isocyanatomethyl)benzene, and 1,3,5-triethyl-2,4-bis(isocyanatomethyl)benzene.

The concentration of the film-forming material in the film-forming material solution is appropriately selected according to the kind of the film-forming material or organic solvent. For example, when the film-forming material is prepared from a vinylenediamide complex represented by formula (1) or (2) and the organic solvent is ethylene glycol monomethyl ether, the concentration of the film-forming material is arbitrary, and a concentration of 0.1 to 33 wt % is preferred, because the thickness of the Group IV metal oxide film can be easily controlled.

After dissolving the film-forming material in an organic solvent, the solution may be subjected to a pretreatment such as heating and filtration, if desired. From the standpoint that a Group IV metal oxide film improved in the electrical properties such as electrical conductivity or in the optical properties such as refractive index can be produced, the film-forming material solution is preferably filtered to remove insoluble matters and then coated on a surface of the later-described substrate.

Also, the film-forming material solution of the present invention may be a solution using and dissolving two or more kinds of film-forming materials in an organic solvent, in addition to a solution using and dissolving one kind of a film-forming material in an organic solvent. By virtue of using two or more kinds of film-forming materials, a composite oxide thin film can be produced.

The Group IV metal oxide film of the present invention is a metal oxide film obtained by coating the above-described film-forming material solution on a surface of a substrate, and subjecting the substrate to a heat treatment, an ultraviolet irradiation treatment, or both of these treatments.

As the method for coating the film-forming material solution on a surface of a substrate, a method generally employed in the thin film production process by wet method can be used. Specific examples thereof include a spin coating method, a dip coating method, a spray coating method, a flow coating method, a roll coating method, a curtain coating method, a bar coating method, an ultrasonic coating method, a screen printing method, brush coating, and sponge coating. From the standpoint that the cost merit is high and a Group IV metal oxide film improved in the electrical properties such as electrical conductivity or in the optical properties such as refractive index can be produced, a spin coating method, a dip coating method, a spray coating method and a bar coating method are preferred.

The kind of the substrate which can be used in the production method of the present invention is not particularly limited, and, for example, a resin substrate such as polyimide resin, polyethylene terephthalate resin, polyethylene resin, polypropylene resin, polycarbonate resin, acrylic resin, polyester resin, ABS resin, AAS resin, polyvinyl chloride resin and polyethylene naphthalate, and a composite resin substrate formed of a composite resin thereof may be used. In addition, an inorganic substrate such as glass, quartz, porcelain or other ceramics, silicon, various metals, various metal oxides and a composite material thereof may be used. It is also possible to use a composite substrate formed by combining a resin substrate and an inorganic substrate.

The temperature in the heat treatment is not particularly limited and is preferably not more than the thermal deformation temperature of the substrate used. Also, by using the production method of the present invention, a Group IV metal oxide film can be produced even by heat treatment at a low temperature. The low temperature is, specifically, preferably from 20 to 1,000° C., more preferably from 20 to 700° C., still more preferably from 20 to 400° C., yet still more preferably from 20 to 200° C.

The heat treatment time is not particularly limited and is preferably from 1 minute to 5 hours, and is more preferably from 1 to 30 minutes, because a necessary and sufficient heat treatment can be applied, and in view of efficiency.

In the case of applying an ultraviolet irradiation treatment, the atmosphere thereof is not particularly limited, and, for example, a gas such as air, oxygen gas, nitrogen gas, hydrogen gas, argon, neon and helium can be used as the atmosphere. The ultraviolet irradiation treatment can also be performed in vacuum without using the gas above as the atmosphere. The irradiation wavelength of ultraviolet ray is not particularly limited, and a Group IV metal oxide film improved in the electrical properties such as electrical conductivity or in the optical properties such as refractive index can be produced by appropriately selecting the wavelength not affecting the substrate from the range of preferably from 200 to 400 nm, more preferably from 250 to 400 nm. The illuminance of ultraviolet ray is not particularly limited and is preferably 100 mJ/cm$^2$ or more, more preferably 500 mJ/cm$^2$ or more. Incidentally, in a Group IV metal oxide film obtained by the irradiation with an ultraviolet ray through a pattern mask (mask substrate), a fine-line pattern in high resolution can be also formed by after-treatment such as etching.

In the case of applying both a heat treatment and an ultraviolet irradiation treatment, the order thereof is not particularly limited and from the standpoint that a Group IV metal oxide film improved in the electrical properties such as electrical conductivity or in the optical properties such as refractive index can be produced, it is preferred to first perform an ultraviolet irradiation treatment and then perform a heat treatment. At this time, the wavelength of ultraviolet ray is preferably from 200 to 400 nm, and the temperature of heat treatment is preferably from 20 to 200° C.

In addition, from the standpoint that a Group IV metal oxide film improved in the electrical properties such as electrical conductivity or in the optical properties such as refractive index can be produced, a method of performing a heat treatment, then performing an ultraviolet irradiation treatment, and further performing, if desired, a re-heating treatment is also preferred. The wavelength of ultraviolet ray in this case is not particularly limited and is preferably from 200 to 400 nm. The temperature of heat treatment in this case is not particularly limited, and a Group IV metal oxide film can be produced even by a heat treatment at a low temperature. The low temperature as used herein is, specifically, preferably from 20 to 700° C., more preferably from 20 to 400° C., still more preferably from 20 to 200° C., yet still more preferably from 20 to 100° C., even yet still more preferably from 20 to 50° C. In the case of performing a re-heating treatment, the temperature thereof is not limited and is preferably The low temperature is, specifically, preferably from 20 to 700° C., more preferably from 20 to 400° C., still more preferably from 20 to 200° C. The re-heating treatment time is not particularly limited and is preferably from 1 minute to 5 hours, and is more preferably from 1 to 30 minutes, because a necessary and sufficient heat treatment can be applied, and in view of efficiency.

In the production method of the present invention, a pattern film of a Group IV metal oxide can be produced by performing an etching treatment in combination with a heat treatment, an ultraviolet irradiation treatment or both of these treatments. In this case, the order among the etching treatment, the heat treatment and the ultraviolet irradiation treatment is not limited and from the standpoint that a pattern film with good resolution can be produced, an order of performing a heat treatment or an ultraviolet irradiation treatment or performing both of these treatments, then performing an etching treatment, and further performing, if desired, a re-heating treatment is preferred. An order of performing a heat treatment, performing an ultraviolet ray irradiation treatment, and then performing an etching treatment is more preferred, and an order of performing a heat treatment, then applying irradiation with an ultraviolet ray, further performing an etching treatment, and finally performing a re-heating treatment is still more preferred.

As the etching treatment method, a general method employed in this technical field can be used. Specific examples thereof include dry etching and wet etching. The method for producing a pattern film by dry etching is described below by referring to one example. A crude film produced by coating a film-forming material of a Group IV metal oxide on an Si wafer substrate and applying an ultraviolet irradiation treatment through a pattern mask (mask substrate) is placed in a chamber of an etching apparatus, and an etching gas is introduced into the chamber to generate plasma. This plasma removes the masking Group IV metal oxide film, and etching proceeds. Incidentally, as the etching gas, a general gas employed in this technical field can be used, and specific examples thereof include hydrogen chloride, hydrogen bromide, hydrogen iodide, chlorine, chlorine trifluoride, iodine pentafluoride, a mixed gas of methane and hydrogen, tetrafluoromethane, difluoromethane, trifluoromethane, hexafluoroethane, octafluoropropane, octafluorocyclobutane, octafluorocyclopentane, iodomethane, trifluoroiodomethane, nitrogen trifluoride, and boron trifluoride. Also, examples of the plasma which can be used include inductively coupled plasma, capacitively coupled plasma, ECR plasma, and microwave plasma. As the plasma source gas, a general gas employed in this technical field can be used, and, for example, an inert gas such as helium, argon, krypton, neon and xenon may be used together with an etching gas.

Next, the method for producing a pattern film by wet etching is described below by referring to one example. A crude film produced by coating a film-forming material of a Group IV metal oxide on an Si wafer substrate and applying an ultraviolet irradiation treatment through a pattern mask is dipped in an etching solution, whereby etching proceeds. As the etching solution, a general etching solution in this technical field can be used. Specifically, for example, an aqueous acid or alkali solution capable of dissolving the Group IV metal oxide film can be used, and specific examples thereof include, but are not limited to, an aqueous acid solution such as aqueous hydrogen peroxide, hydrochloric acid, nitric acid, sulfuric acid, oxalic acid, hydrofluoric acid, hydrobromic acid, hydrocyanic acid, hypochlorous acid and aqua regia, and an aqueous alkali solution such as aqueous potassium iodide solution, aqueous ammonium chloride solution, aqueous tetramethylammonium hydroxide solution, aqueous sodium carbonate solution, aqueous sodium hydroxide solution and aqueous potassium hydroxide solution. Furthermore, the etching solution may also be performed by appropriately mixing a compatible organic solvent for etching with the aqueous acid or alkali solution. The compatible organic solvent for etching includes, for example, an alcohol, a diol, an ether, an imide, a cyclic imide, and a carbonic acid ester. Examples thereof include, but are not limited to, ethylene glycol, propylene glycol, diethylene glycol, 1,2-propanediol, 1,4-butanediol, 2,3-butanediol, ethylene glycol monomethyl ether, ethylene glycol monoethyl ether, N-methylformamide, N,N-dimethylformamide, N,N-diethylformamide, N-methylacetamide, N,N-dimethylacetamide, N-methylpropionamide, N-methyl-2-pyrrolidinone, 2-pyrrolidinone, 1,3-dimethyl-2-imidazolidinone, quinoline, ethylene carbonate, propylene carbonate, and γ-butyrolactone. Furthermore, the etching treatment may also be performed by appropriately mixing a functional agent having a function of, for example, decreasing the surface tension of an etching solution for microfabrication treatment. Examples of the functional agent include, but are not limited to, an organic acid such as formic acid, acetic acid, propionic acid, oxalic acid, malonic acid and succinic acid, and a surfactant such as dodecylbenzenesulfonic acid and polyoxyethylene glycol ether. The dip-etching time is not particularly limited and is preferably from 1 second to 1 hour, more preferably from 5 seconds to 30 minutes. The dip-etching temperature is not particularly limited as long as it is a temperature not involving solidification or evaporation of the etching solution, and the dip-etching temperature is preferably from −10° C. to 50° C., more preferably from 0 to 30° C.

According to the production method of a Group IV metal oxide film of the present invention, not only a single layer film but also a multilayer film of two or more layers can be produced. For producing a multilayer film, either a sequential lamination method where a method of coating one layer and applying a heat treatment, an ultraviolet irradiation treatment or both of these treatments is repeated, or a lamination method where coating is repeated to form multiple layers and thereafter, the layers are en bloc subjected to a heat treatment, an ultraviolet irradiation treatment or both of these treatments, can be employed.

The Group IV metal oxide film obtained by the method above is a film having a small surface roughness. The value of surface roughness is preferably from 0.2 to 1 nm, more preferably from 0.2 to 0.5 nm.

The Group IV metal oxide film produced by the present invention can be used, for example, as an antireflection film of a touch panel and the like, a transparent electroconductive film of a solar cell and the like, a hard coating agent, a scratch repairing material for glass and the like, a gas barrier material, a photocatalytic member, or a protective coating material against plasma and a hydrofluoric acid solution. Specific examples of the industrial product for which the film is used include electric appliances such as television, radio, computer and cellular phone, interior and exterior materials for building, interior and exterior materials for vehicle, ship, aircraft and the like, various glasses such glass fiber, glass powder and glass sheet, window members for vehicle, ship, aircraft and the like, lighting devices, tiles, medical devices, medical instruments, medical materials, hygienic articles, deposition devices for the production of semiconductor and the like, plasma treatment devices (plasma etching device, plasma cleaning device and ashing device), optical cells, and microfluidic chips.

EXAMPLES

The present invention is described in greater detail below by referring to Examples, but the present invention is not limited thereto. Incidentally, in the description of the present invention, Me, Et, Pr, $^{i}$Pr, Bu, $^{i}$Bu, $^{s}$Bu, $^{t}$Bu, $^{t}$Pe and $^{t}$Oct stand for a methyl group, an ethyl group, a propyl group, an isopropyl group, a butyl group, an isobutyl group, a sec-butyl group, a tert-butyl group, a tert-pentyl group, and a 1,1,3,3-tetramethylbutyl group (tert-octyl group), respectively.

Example-1

In an argon atmosphere, 829 mg (2.48 mmol) of N,N'-di-tert-butyl-1,2-vinylenediamide-$\kappa^2$N,N')diisopropoxytitanium(Ti($^{t}$BuNCH=CHN$^{t}$Bu)(O$^{i}$Pr)$_2$) and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 15 hours while keeping the connection of the balloon to the Schlenk tube, the inside of the Schlenk was depressurized to 10 Pa under heating at 80° C., and 2 mL of hexane was added to and dissolved in the obtained residue. The resulting solution was passed through a syringe filter (SLLGM25NS, manufactured by Millipore, pore size: 0.20 μm) to remove insoluble matters by filtration, and the syringe filter used was washed twice with 2 mL of hexane. The filtrate and the washing liquid were combined and concentrated to obtain 510 mg of a yellow solid.

The obtained yellow solid was dissolved in 3 mL of ethylene glycol monomethyl ether in an argon atmosphere and heated at 80° C. for 14 hours, and while heating the reaction vessel by immersion in an oil bath at 70° C., the solution was evaporated to dryness over 5 hours under reducing the pressure inside the reaction vessel to 10 Pa to obtain 470 mg of Film-forming Material 1 as a black solid. Film-Forming Material 1 (470 mg) was dissolved in 3 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-01 was obtained. The black solid above is a film-forming material obtained by dissolving the yellow solid in ethylene glycol monomethyl ether that is an alcohol containing two or more oxygen atoms in the molecule, and then heating the solution.

Also, 0.30 g of a yellow solid obtained in the same manner as above was transferred to a Schlenk tube, and the yellow solid was dissolved in 0.8 ml of diethyl ether. After immersing the Schlenk tube in an ice bath for 3 hours, the Schlenk tube is cooled to −30° C. to obtain a white needle-like crystal. Incidentally, the single-crystal X-ray structural analysis revealed that the needle-like crystal is $Ti_{11}O_{13}(O^{i}Pr)_{18}$ having 11 titanium atoms which are bridged by a $\mu_3$ bridging oxygen atom.

(X-Ray Crystal Analysis)

The molecular structure and crystal structure of the obtained crystal were determined using a single-crystal X-ray structural analyzer (Rigaku R-Axis RAPID II). The final R value in the structural analysis and refinement was 0.14. The final Rw value was 0.36.

Compositional formula: $C_{54}H_{126}O_{13}Ti_{11}$
Crystal system: monoclinic
Space group: $P2_1/C$
Lattice constant: a=25.74 Å, b=14.19 Å, c=26.66 Å, $\alpha=\gamma=90°$, $\beta=108°$ Example-2

Film-Forming Material 1 (2.24 g) obtained by the same method as in Example-1 from 3.98 g (11.90 mmol) (N,N'-di-tert-butyl-1,2-vinylenediamide-$\kappa^2$N,N')diisopropoxytitanium(Ti($^t$BuNCH=CHN$^t$Bu)(O$^i$Pr)$_2$) was dissolved in 4.8 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-02 was obtained.

Example-3

Film-Forming Material 1 (2.24 g) obtained by the same method as in Example-1 from 3.98 g (11.90 mmol) (N,N'-di-tert-butyl-1,2-vinylenediamide-$\kappa^2$N,N')diisopropoxytitanium(Ti($^t$BuNCH=CHN$^t$Bu)(O$^i$Pr)$_2$) was dissolved in 9.6 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-03 was obtained.

Example-4

Film-Forming Material 1 (2.24 g) obtained by the same method as in Example-1 from 3.98 g (11.90 mmol) (N,N'-di-tert-butyl-1,2-vinylenediamide-$\kappa^2$N,N')diisopropoxytitanium(Ti($^t$BuNCH=CHN$^t$Bu)(O$^i$Pr)$_2$) was dissolved in 29 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-04 was obtained.

Example-5

Film-Forming Material 1 (2.24 g) obtained by the same method as in Example-1 from 3.98 g (11.90 mmol) (N,N'-di-tert-butyl-1,2-vinylenediamide-$\kappa^2$N,N')diisopropoxytitanium(Ti($^t$BuNCH=CHN$^t$Bu)(O$^i$Pr)$_2$) was dissolved in 24 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-05 was obtained.

Example-6

Film-Forming Material 1 (2.24 g) obtained by the same method as in Example-1 from 3.98 g (11.90 mmol) (N,N'-di-tert-butyl-1,2-vinylenediamide-$\kappa^2$N,N')diisopropoxytitanium(Ti($^t$BuNCH=CHN$^t$Bu)(O$^i$Pr)$_2$) was dissolved in 12 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-06 was obtained.

Example-7

In an argon atmosphere, 10.7 g (32.1 mmol) of N,N'-di-tert-butyl-1,2-vinylenediamide-$\kappa^2$N,N')diisopropoxytitanium(Ti($^t$BuNCH=CHN$^t$Bu)(O$^i$Pr)$_2$), 14 ml of toluene and a magnetic stirrer were put in a 50-ml Schlenk tube to prepare a toluene solution of vinylenediamide complex, and a mixed gas of oxygen and argon (oxygen: 20 vol %) was flowed at a flow rate of 100 ml/min to the toluene solution through a Teflon (registered trademark) tube with stirring. After 3 hours, the flowing of gas was stopped, and the toluene solution was cooled to room temperature. The toluene solution was removed under reduced pressure, and 40 ml of acetonitrile was added to the residue. Insoluble matters were collected by filtration, and the insoluble matters collected were dried under reduced pressure to obtain 3.49 g of a gray-white solid. The obtained gray-white solid (1.56 g) was dissolved in 9.1 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 1.58 g of Film-forming Material 2 as an orange solid. Film-Forming Material 2 (1.58 g) was dissolved in 6.5 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-07 was obtained.

Example-8

In an argon atmosphere, 2.9 g (9.6 mmol) of N,N'-di-tert-butyl-1,2-vinylenediamide-$\kappa^2$N,N')diethoxytitanium(Ti($^t$BuNCH=CHN$^t$Bu)(OEt)$_2$) and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 15 hours while keeping the connection of the balloon to the Schlenk tube, the inside of the Schlenk was depressurized to 10 Pa under heating at 80° C., and 2 mL of hexane was added to and dissolved in the obtained residue. The resulting solution was passed through a syringe filter (SLLGM25NS, manufactured by Millipore, pore size: 0.20 μm) to remove insoluble matters by filtration, and the syringe filter used was washed twice with 2 mL of hexane. The filtrate and the washing liquid were combined and concentrated to obtain 1.5 g of a yellow solid, and 1.1 g of the obtained yellow solid was dissolved in 10 mL of ethylene glycol monomethyl ether in an argon atmosphere. The resulting solution was heated at 80° C. for 14 hours and further evaporated to dryness over 5 hours under reducing the pressure inside the reaction vessel to 10 Pa at 80° C. to obtain 1.4 g of Film-forming Material 3 as a black solid. Film-Forming Material 3 (1.4 g) was dissolved in 12 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-08 was obtained.

Example-9

In an argon atmosphere, 2.9 g (8.7 mmol) of N,N'-di-tert-butyl-1,2-vinylenediamide-$\kappa^2$N,N')di-normal-propyltitanium(Ti($^t$BuNCH=CHN$^t$Bu)(O$^n$Pr)$_2$) and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 15 hours while keeping the connection of the balloon to the Schlenk tube, the inside of the Schlenk was depressurized to 10 Pa under heating at 80° C., and 2 mL of hexane was added to and dissolved in the obtained residue. The resulting solution was passed through a syringe filter (SLLGM25NS, manufactured by Millipore, pore size: 0.20 μm) to remove insoluble matters by filtration, and the syringe filter used was washed twice with 2 mL of hexane. The filtrate and the washing liquid were combined and concentrated to obtain 1.2 g of a yellow solid. Thereafter, 0.90 g of obtained yellow solid was dissolved in 10 mL of ethylene glycol monomethyl ether in an argon atmosphere, and the resulting solution was heated at 80° C. for 14 hours and further evaporated to dryness over 5 hours under reducing the pressure inside the reaction vessel to 10 Pa at 80° C. to obtain 0.87 g of Film-forming Material 4 as a black solid. Film-Forming Material 4 (0.87 g) was dissolved in 8 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Ti-09 was obtained.

Example-10

In an argon atmosphere, 1.80 g (6.28 mmol) of N,N'-di-tert-butyl-1,2-vinylenediamide-κ$^2$N,N')diethoxysilane(Si($^t$BuNCH=CHN$^t$Bu)(OEt)$_2$) and a magnetic stirrer were put in a 50-mL Schlenk tube, and the inside of the Schlenk tube was depressurized to 20 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 65 hours while keeping the connection of the balloon to the Schlenk tube, the inside of the Schlenk was depressurized to 10 Pa under heating at 80° C. to obtain 0.63 g of a white suspension. Film-Forming Material 5 (0.63 g of white suspension) was dissolved in 10 mL of ethylene glycol monomethyl ether and passed through a syringe filter (SLLGM25NS, manufactured by Millipore, pore size: 0.20 μm) to remove insoluble matters by filtration, whereby Film-Forming Material Solution Si-01 was obtained.

Example-11

In an argon atmosphere, 5.0 g (32.1 mmol) of N,N'-di-tert-butyl-1,2-vinylenediamide-κ$^2$N,N')diethoxysilane(Si($^t$BuNCH=CHN$^t$Bu)(OEt)$_2$), 20 ml of toluene and a magnetic stirrer were put in a 50-ml Schlenk tube to prepare a toluene solution of vinylenediamide complex, and a mixed gas of oxygen and argon (oxygen: 20 vol %) was flowed at a flow rate of 100 ml/min to the toluene solution through a Teflon (registered trademark) tube with stirring. After 4 hours, the flowing of gas was stopped, and the toluene solution was cooled to room temperature. The toluene solution was removed under reduced pressure, and the residue was vacuum dried for 7 hours under reduced pressure of 10 Ps while heating it at 80° C. to obtain 3.18 g of a colorless liquid. The obtained colorless liquid (0.61 g) was dissolved in 3.1 mL of ethylene glycol monomethyl ether in an argon atmosphere, and the resulting solution was heated at 80° C. for 18 hours and further stirred over 10 hours under reducing the pressure inside the reaction vessel to 10 Pa at 22° C. to obtain 0.62 g of Film-Forming Material Solution 6 as a colorless liquid. Film-Forming Material 6 (0.62 g of colorless liquid) was dissolved in 2.5 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Si-02 was obtained.

Examples-12 to 50 and Comparative Examples-1 to 3

Each of the film-forming material solutions produced by the methods described in Example-1 to Example-11 and a TiO$_2$ film-forming material solution SYM-01 (SYM-T105 produced by Kojundo Chemical Lab. Co., Ltd.: 0.5 mol/L) as Comparative Example was coated on a surface of a substrate by spin coating method, and the substrate was heat-treated to produce a Group IV metal oxide film. Evaluation results of the obtained metal oxide films are shown in Tables 1 to 3. The film thickness and refractive index were determined by performing multilayer film analysis of the spectrum at a wavelength of 300 to 800 nm measured by means of an ellipsometer (MEL-30S, manufactured by JASCO Corporation).

Examples-51 to 54

Film-Forming Material Solution Ti-05 or Ti-06 produced by the method described in Example-5 or 6 was coated on a surface of a substrate by spin coating method and after subjecting the substrate to an ultraviolet irradiation treatment, a heat treatment was performed only in Examples-53 and 54 to produce a Group N metal oxide film. Evaluation results of the obtained Group IV metal oxide films are shown in Table 4. The film thickness and refractive index were determined by performing multilayer film analysis of the spectrum at a wavelength of 300 to 800 nm measured by means of an ellipsometer (MEL-30S, manufactured by JASCO Corporation).

Test Example-1

Characteristics of a Group IV metal oxide film obtained by coating Film-Forming Material Solution Ti-01 or Film-Forming Material Solution Si-01 produced by the method described in Example-1 or 10 on a surface of a substrate by spin coating method and heat-treating the substrate are shown in Table 5. Items in Table 5 are described below. The transmittance and reflectance of the Group IV metal oxide film were determined based on the spectrum measured by means of a spectrometer (U-4100, manufactured by HITACHI). The pencil hardness (JIS K5600-5-4) was determined based on the maximum pencil hardness above which the Group IV metal oxide film is marred when scratched by a pencil under a load of 750 g. The surface roughness Ra was determined based on the results of observation of every each 2 μm×2 μm width by using a scanning probe microscope NanoScope IIIa (manufactured by Veeco). In the cross-cut test (JIS K5400), 100 squares in total were incised in the film by a cutter knife, with one square being a 1 mm square, a cellophane adhesive tape of about 5 cm was adhered to the grid of squares and then instantaneously peeled off at an angle of 90° C. with respect to the coated surface, and the number of squares not peeled off among 100 squares is shown.

Test Example-2

A Group IV metal oxide film obtained by coating Film-Forming Material Solution Ti-01 produced by the method described in Example-1 on a surface of a substrate by spin coating method and heat-treating the substrate was measured for the transmittance in the ultraviolet region, and the result is shown in Table 6.

Test Example-3

A Group IV metal oxide film obtained by coating Film-Forming Material Solution Ti-05 produced by the method described in Example-5 on a surface of a substrate by spin coating method and heat-treating the substrate was subjected to a durability test. The film was placed in a constant-temperature constant-humidity bath at 80° C. and 95% RH, and the refractive indexes before and after placement were measured. The results are shown in Table 7. In Table 7, "test time: 0 hour" indicates before placement, and "test time: 100 h" on the next line indicates after placement.

Test Example 4

Film-Forming Material Solution Ti-05 produced by the method described in Example 5 was evaluated for the storage stability in air. Each of solutions obtained by exposing Film-Forming Material Solution Ti-05 to air for the time shown in Table 8 and then passing it through a syringe filter (SLLGM25NS, manufactured by Millipore, pore size: 0.20 µm) to remove insoluble matters by filtration was coated on a surface of a substrate by spin coating method, and the substrate was heat-treated to produce a Group IV metal oxide film. Evaluation results of obtained Group IV metal oxide films are shown in Table 8.

Example-55

Figure 2:
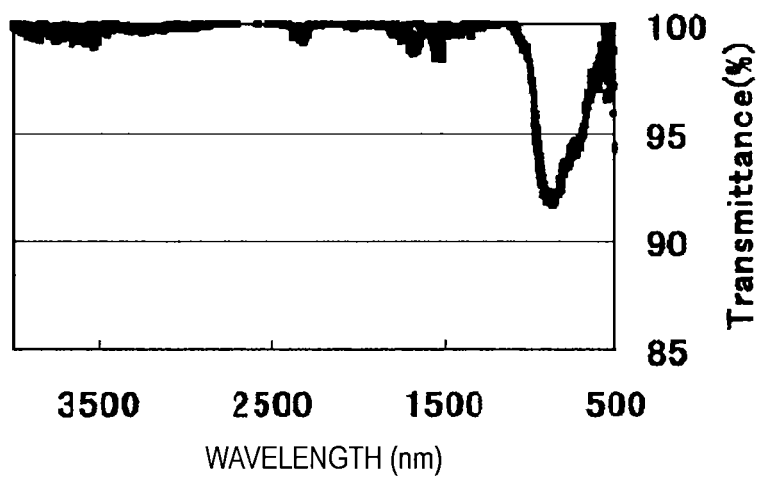
FIG. 2 is a graph showing the IR spectrum of a film.

A group IV metal oxide film obtained by coating Film-Forming Material Solution Ti-06 produced by the method described in Example-6 on an Al substrate by spin coating method and subjecting the substrate to irradiation with a high-pressure mercury lamp (47 J/cm$^2$) of 365 nm and then to a heat treatment at 200° C. for 30 minutes was measured for the IR spectrum. FIG. 2 shows the results. A signal based on O—H stretching vibration of a hydroxyl group or C—H stretching vibration of an organic group was scarcely observed, and it was understood that water or an organic group does not remain in the film. Incidentally, at the coating, conditions where the substrate is processed at a rotation speed of 200 rpm for 15 seconds and then processed at a rotation speed of 2,000 rpm for 30 seconds, were used.

Comparative Example-4

A sample obtained by coating Film-Forming Material Solution Ti-06 produced by the method described in Example-6 on an Al substrate by spin coating method and applying neither a heat treatment nor an ultraviolet irradiation treatment was measured for the IR spectrum. FIG. 1 shows the results. A signal based on O—H stretching vibration of a hydroxyl group or C—H stretching vibration of an organic group was observed in the vicinity of 3,600 to 2,500 cm$^{-1}$ and in the vicinity of 1,600 cm$^{-1}$. Incidentally, at the coating, conditions where the substrate is processed at a rotation speed of 200 rpm for 15 seconds and then processed at a rotation speed of 2,000 rpm for 30 seconds, were used.

Example-56

Figure 3:
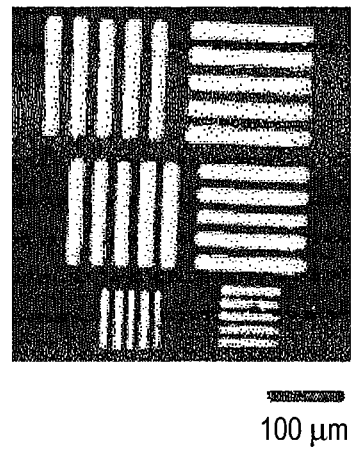
FIG. 3 is a view showing the results when a film having formed therein a pattern with a resolution of 5 μm or more is observed by an optical microscope.

Film-Forming Material Solution Ti-06 produced by the method described in Example-6 was coated on an Si wafer substrate by spin coating method (under the conditions where the substrate is processed at a rotation speed of 200 rpm for 15 seconds and then processed at a rotation speed of 2,000 rpm for 30 seconds) and thereafter, irradiated with an ultraviolet lamp (UPE-2002, manufactured by Ushio Inc.; wavelengths of 200 to 400 nm are mixed) (900 mJ/cm$^2$) through a pattern mask (mask substrate) to obtain a crude film. The obtained crude film was first dipped in ethylene glycol monomethyl ether for 20 minutes, then in an aqueous 2.5% tetramethylammonium hydroxide solution for 80 seconds and further in pure water for 5 minutes and thereafter, left standing still in a drier kept at 50° C. to produce a pattern film. This pattern film was observed by an optical microscope, as a result, the resolution was found to be 5 µm or more. FIG. 3 shows the results of observation of the pattern film by an optical microscope.

Example-57

Figure 4:
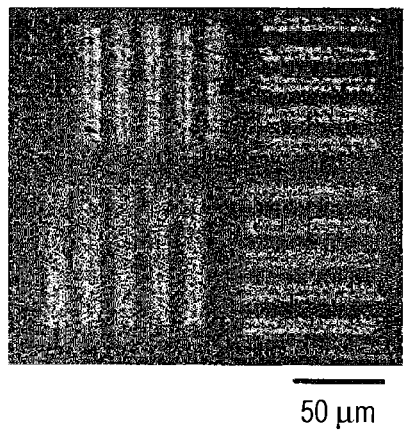
FIG. 4 is a view showing the results when a film having formed therein a pattern with a resolution of 4 μm or more is observed by an optical microscope.

Film-Forming Material Solution Ti-03 produced by the method described in Example-3 was coated on an Si wafer substrate by spin coating method (under the conditions where the substrate is processed at a rotation speed of 200 rpm for 15 seconds and then processed at a rotation speed of 2,000 rpm for 30 seconds) and thereafter, the Si wafer substrate was heat-treated (at 40° C. for 10 minutes). This Si wafer was irradiated with an ultraviolet lamp (UPE-2002, manufactured by Ushio Inc.; wavelengths of 200 to 400 nm are mixed) (400 mJ/cm$^2$) through a pattern mask (mask substrate) to obtain a crude film. The obtained crude film was etched by dipping it in an aqueous 2.4% tetramethylammonium hydroxide solution for 24 minutes, further dipped in pure water for 5 minutes and thereafter, left standing still in a drier kept at 50° C. to produce a pattern crude film. This pattern crude film was subjected to a re-heating treatment at 230° C. for 30 minutes to produce a pattern film. The produced pattern film was observed by an optical microscope, as a result, the resolution was found to be 4 µm or more. FIG. 4 shows the results of observation of the pattern film by an optical microscope.

Example-58

Figure 5:
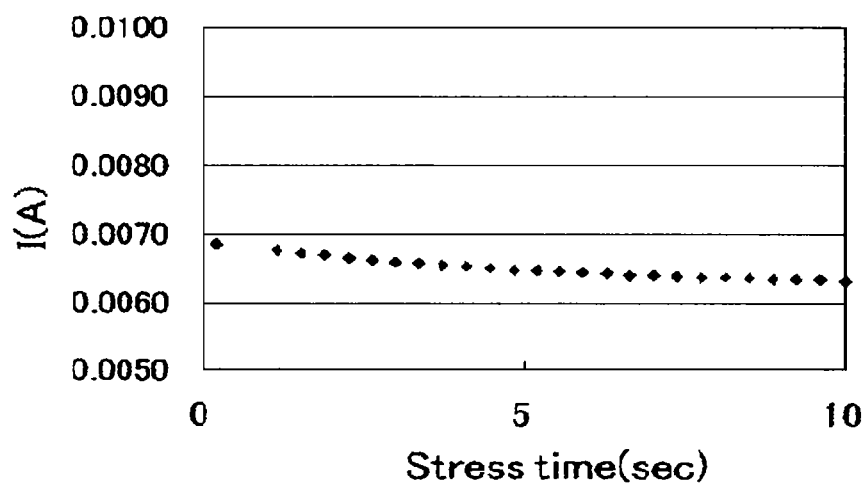
FIG. 5 is a graph showing the withstand voltage properties of a film.

Film-Forming Material Solution Ti-06 produced by the method described in Example-6 was coated on an Si wafer substrate by spin coating method (under the conditions where the substrate is processed at a rotation speed of 200 rpm for 15 seconds and then processed at a rotation speed of 2,000 rpm for 30 seconds) and thereafter, irradiated with an ultraviolet lamp (UPE-2002, manufactured by Ushio Inc.; wavelengths of 200 to 400 nm are mixed) (900 mJ/cm$^2$). This Si wafer substrate was heat-treated at 300° C. for 30 minutes to produce a Group IV metal oxide film. Furthermore, an Al electrode was formed on a surface of the produced film, whereby a specimen for test was produced. A voltage of 15 V was applied to the test specimen for 10 seconds, and the withstand voltage properties were measured, as a result, the specimen was found to have a sufficient withstand voltage. FIG. 5 shows the withstand voltage properties.

Example-59

Figure 6:
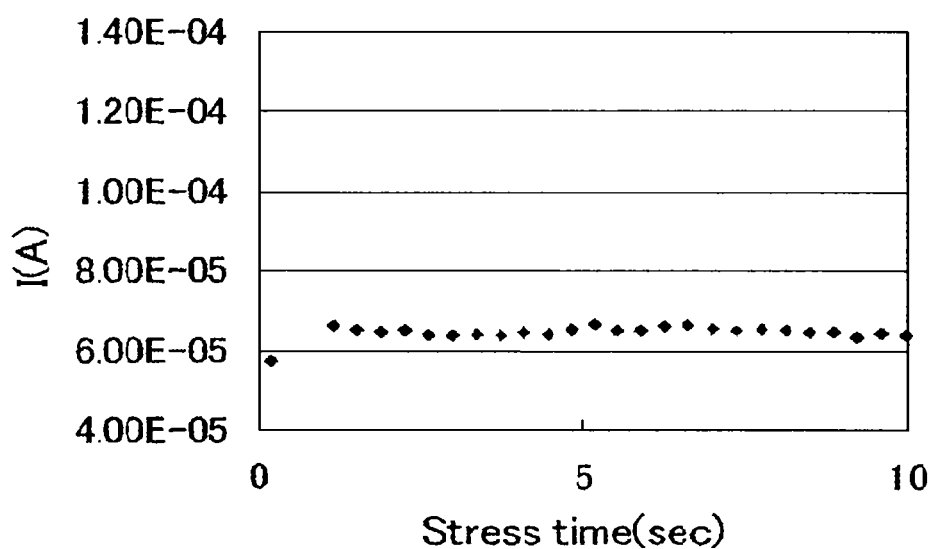
FIG. 6 is a graph showing the withstand voltage properties of a film.

Film-Forming Material Solution Ti-06 produced by the method described in Example-6 was coated on an Si wafer substrate by spin coating method (under the conditions where the substrate is processed at a rotation speed of 200 rpm for 15 seconds and then processed at a rotation speed of 2,000 rpm for 30 seconds) and thereafter, irradiated with an ultraviolet lamp (UPE-2002, manufactured by Ushio Inc.; wavelengths of 200 to 400 nm are mixed) (900 mJ/cm$^2$). This substrate was heat-treated at 500° C. for 30 minutes to produce a Group IV metal oxide film on the substrate. Furthermore, an Al electrode was formed on a surface of the produced film, whereby a specimen for test was produced. A voltage of 15 V was applied to the test specimen for 10 seconds, and the withstand voltage properties were measured, as a result, the specimen was found to have a sufficient withstand voltage. FIG. 6 shows the withstand voltage properties.

Example-60

Figure 7:
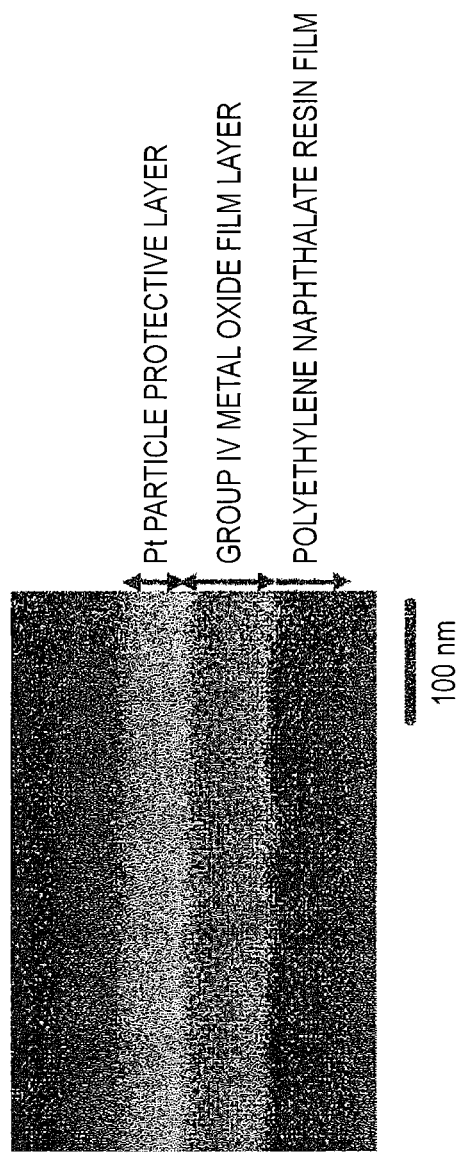
FIG. 7 is a view showing the results of cross-sectional SEM observation of a film.

Film-Forming Material Solution Ti-05 produced by the method described in Example-5 was coated on a surface of a polyethylene naphthalate resin film substrate (Teonex 200, Q65FA, produced by Teijin DuPont Films Japan Limited) by wire bar coating method (PM-9050MC, manufactured by SMT Corporation; coating speed: 9.5 m/min), and the substrate was heat-treated at 180° C. for 30 minutes to produce a Group IV metal oxide film on the polyethylene naphthalate resin film. The film thickness and refractive index thereof were measured using an ellipsometer (MEL-30S, manufactured by JASCO Corporation). These were examined based on multilayer film analysis of the spectrum at a wavelength of 300 to 800 nm, as a result, the film thickness was 69 nm and the refractive index at a wavelength of 633 nm was 1.95. Also, FIG. 7 shows the results of cross-sectional SEM observation of the Group IV metal oxide film.

Test Example-5

A Group IV metal oxide film obtained by coating Film-Forming Material Solution Ti-01 or Ti-05 produced by the method described in Example-1 or 5 on a surface of a substrate by spin coating method and heat-treating the substrate was subjected to a plasma resistance test. A Kapton tape was attached to the central part on the substrate surface to serve as a mask, and plasma etching of this substrate was performed at an output of 300 W for 2 minutes while flowing a mixed gas of $CF_4$ (flow rate: 25.2 sccm)-$O_2$ (flow rate: 6.34 sccm)-Ar (flow rate: 126 stem) by using a parallel plate reactive ion etching apparatus (DEM-451, manufactured by ANELVA). After the plasma etching, the Kapton tape was peeled off, and the step generated at the interface between the Kapton tape-attached part and the non-attached part was measured at three portions in the same sample by using a contact surface roughness meter (DEKTAK3030, manufactured by Sloan). The average value thereof was taken as the plasma etching amount, and a value obtained by dividing the plasma etching amount by the etching time was taken as the plasma etching speed. Incidentally, when plasma etching was performed under the same conditions, the plasma etching speed of quartz glass used as the substrate was 60.0 nm/min. The results of this test are shown in Table 9.

Test Example-6

A Group IV metal oxide film obtained by coating Film-Forming Material Solution Ti-01 produced by the method described in Example 1 on a surface of a substrate by spin coating method and heat-treating the substrate for 0.5 hours was subjected to a hydrofluoric acid solution resistance test. A Kapton tape was attached to the central part on the substrate surface to serve as a mask, and this substrate was dipped in an aqueous 0.5 wt % hydrofluoric acid solution at 20° C., thereby performing wet etching. After the etching for a predetermined time, the Kapton tape was peeled off, and the step generated at the interface between the Kapton tape-attached part and the non-attached part was measured at three portions in the same sample by using a contact surface roughness meter (DEK-TAK3030, manufactured by Sloan). The average value thereof was taken as the wet etching amount, and a value obtained by dividing the wet etching amount by the etching time was taken as the wet etching speed. Incidentally, when wet etching was performed under the same conditions, the wet etching speed of quartz glass used as the substrate was 1.5 nm/min. The results of this test are shown in Table 10.

Test Example-7

A Group IV metal oxide film was obtained by coating Film-Forming Material Solution Ti-03 produced by the method described in Example-3 on a surface of a Corning glass substrate by spin coating method (under the conditions where the substrate is processed at a rotation speed of 200 rpm for 15 seconds and then processed at a rotation speed of 2,000 rpm for 30 seconds) and subjecting the substrate to irradiation with a high-pressure mercury lamp (47 J/cm$^2$) with a main wavelength of 365 nm and then to a heat treatment at 130° C. for 30 minutes. The contact angle test of the obtained Group IV metal oxide film was performed in conformity with the standard of JIS R 1703-1:2007. First, five test pieces where a film was formed on a 5 cm-square coating substrate, were prepared. Subsequently, five test pieces were washed with ethanol (produced by Wako Pure Chemical Industries, Ltd., first grade), then naturally dried for 24 hours, and irradiated with an ultraviolet ray at an illuminance of 2.0 mW/cm$^2$ for 24 hours by using an ultraviolet irradiation apparatus (ultraviolet illuminance meter: controller part: C-9546-01 and sensor part: H9958-01, both manufactured by Hamamatsu Photonics K.K., black light: FL10BLB manufactured by Toshiba, two tubes). Thereafter, 0.5 mg of oleic acid was coated on each of test pieces. The test pieces after the coating of oleic acid were contacted with water to form a waterdrop and measured for the contact angle by a contact angle measuring apparatus (DM-300, manufactured by Kyowa Interface Science Co., Ltd.). The contact angle was measured at 5 points in the test piece, and the average value thereof was taken as the initial contact angle. Irradiation of the test piece with ultraviolet ray (illuminance: 2.0 mW/cm$^2$) was started, and the contact angle (average value of 5 points in the test piece) was measured every 8 hours. The results are shown in Table 11.

Test Example-8

Film-Forming Material Solution Ti-03 produced by the method described in Example-3 was coated on a surface of a Corning glass substrate by spin coating method (under the conditions where the substrate is processed at a rotation speed of 200 rpm for 15 seconds and then processed at a rotation speed of 2,000 rpm for 30 seconds) and heat-treated at 700° C. for 30 minutes. A contact angle test of the produced Group IV metal oxide film was performed. The test method was the same as in Test Example-7. The change in contact angle of this test piece is shown in Table 12.

TABLE 1

| Example | Sample | Rotation Condition | Substrate | Heat Treatment Temperature | Heat Treatment Time | Film Thickness (nM) | Refractive Index |
|---|---|---|---|---|---|---|---|
| Example-12 | Ti-01 | A | Si wafer | 200° C. | 30 min | 101 | 1.93 |
| Example-13 | Ti-01 | B | Corning glass | 200° C. | 30 min | 181 | 1.91 |
| Example-14 | Ti-02 | C | Corning glass | 200° C. | 30 min | 309 | 1.88 |
| Example-15 | Ti-02 | A | Corning glass | 200° C. | 30 min | 506 | 1.91 |
| Example-16 | Ti-02 | B | Corning glass | 200° C. | 30 min | 782 | 1.96 |
| Example-17 | Ti-02 | D | Corning glass | 200° C. | 30 min | 1248 | 1.89 |
| Example-18 | Ti-03 | C | Corning glass | 200° C. | 30 min | 98 | 1.89 |
| Example-19 | Ti-03 | A | Corning glass | 200° C. | 30 min | 158 | 1.88 |
| Example-20 | Ti-03 | B | Corning glass | 200° C. | 30 min | 261 | 1.88 |
| Example-21 | Ti-03 | D | Corning glass | 200° C. | 30 min | 396 | 1.87 |
| Example-22 | Ti-04 | C | Corning glass | 200° C. | 30 min | 38 | 1.90 |
| Example-23 | Ti-04 | A | Corning glass | 200° C. | 30 min | 60 | 1.90 |
| Example-24 | Ti-04 | B | Corning glass | 200° C. | 30 min | 89 | 1.90 |
| Example-25 | Ti-04 | D | Corning glass | 200° C. | 30 min | 128 | 1.96 |
| Example-26 | Ti-05 | E | Corning glass | 200° C. | 2 min | 110 | 1.90 |
| Example-27 | Ti-05 | E | Corning glass | 200° C. | 5 min | 110 | 1.91 |
| Example-28 | Ti-05 | E | Corning glass | 200° C. | 10 min | 107 | 1.91 |
| Example-29 | Ti-05 | E | Corning glass | 200° C. | 30 min | 106 | 1.93 |

TABLE 2

| Example | Sample | Rotation Condition | Substrate | Heat Treatment Temperature | Heat Treatment Time | Film Thickness (nm) | Refractive Index |
|---|---|---|---|---|---|---|---|
| Example-30 | Ti-01 | A | Corning glass | 120° C. | 30 min | 227 | 1.81 |
| Example-31 | Ti-01 | A | Corning glass | 150° C. | 30 min | 169 | 1.93 |
| Example-32 | Ti-01 | A | Corning glass | 200° C. | 30 min | 120 | 1.87 |
| Example-33 | Ti-01 | A | Corning glass | 400° C. | 30 min | 67 | 2.15 |
| Example-34 | Ti-01 | A | Corning glass | 700° C. | 30 min | 64 | 2.16 |
| Example-35 | Ti-07 | F | Corning glass | 120° C. | 30 min | 80 | 1.87 |
| Example-36 | Ti-07 | F | Corning glass | 200° C. | 30 min | 63 | 2.09 |
| Example-37 | Ti-07 | F | Corning glass | 400° C. | 30 min | 48 | 2.24 |
| Example-38 | Ti-07 | F | Corning glass | 700° C. | 30 min | 50 | 2.23 |
| Example-39 | Ti-08 | F | Corning glass | 120° C. | 30 min | 83 | 1.85 |
| Example-40 | Ti-08 | F | Corning glass | 200° C. | 30 min | 73 | 1.89 |
| Example-41 | Ti-08 | F | Corning glass | 400° C. | 30 min | 48 | 2.10 |
| Example-42 | Ti-08 | F | Corning glass | 700° C. | 30 min | 43 | 2.10 |
| Example-43 | Ti-09 | F | Corning glass | 120° C. | 30 min | 121 | 1.79 |

TABLE 2-continued

| Example | Sample | Rotation Condition | Substrate | Heat Treatment Temperature | Heat Treatment Time | Film Thickness (nm) | Refractive Index |
|---|---|---|---|---|---|---|---|
| Example-44 | Ti-09 | F | Corning glass | 200° C. | 30 min | 108 | 1.84 |
| Example-45 | Ti-09 | F | Corning glass | 400° C. | 30 min | 68 | 2.08 |
| Example-46 | Ti-09 | F | Corning glass | 700° C. | 30 min | 63 | 2.12 |
| Comparative Example-1 | SYM-01 | A | Corning glass | 150° C. | 30 min | 252 | 1.66 |
| Comparative Example-2 | SYM-01 | A | Corning glass | 200° C. | 30 min | 161 | 1.70 |
| Comparative Example-3 | SYM-01 | A | Corning glass | 550° C. | 30 min | 210 | 2.09 |

TABLE 3

| Example | Sample | Rotation Condition | Substrate | Heat Treatment Temperature | Heat Treatment Time | Film Thickness (nm) | Refractive Index |
|---|---|---|---|---|---|---|---|
| Example-47 | Si-01 | B | quartz glass | 200° C. | 30 min | 37 | 1.41 |
| Example-48 | Si-01 | B | quartz glass | 400° C. | 30 min | 25 | 1.41 |
| Example-49 | Si-02 | E | Si wafer | 200° C. | 30 min | 143 | 1.37 |
| Example-50 | Si-02 | E | Si wafer | 400° C. | 30 min | 160 | 1.31 |

TABLE 4

| No. | Sample | Rotation Condition | Substrate | Ultraviolet Wavelength (nm) | Ultraviolet Time (nm) | Heat Treatment Temperature | Heat Treatment Time | Film Thickness (nm) | Refractive Index (634 nm) |
|---|---|---|---|---|---|---|---|---|---|
| Example-51 | Ti-05 | F | Si wafer | 365 | 30 | — | — | 85 | 1.73 |
| Example-52 | ↑ | F | Si wafer | 254 | 30 | — | — | 77 | 1.69 |
| Example-53 | Ti-06 | F | Corning glass | 365 | 30 | 200° C. | 0.5 h | 129 | 2.00 |
| Example-54 | ↑ | F | Corning glass | 254 | 30 | 200° C. | 0.5 h | 121 | 2.04 |

TABLE 5

| Sample | Rotation Condition | Substrate | Heat Treatment Temperature | Heat Treatment Time | Transmittance (634 nm) | Reflectance (634 nm) | Pencil Hardness | Surface Ra | Cross-Cut Test |
|---|---|---|---|---|---|---|---|---|---|
| Ti-01 | A | quartz glass | 200° C. | 0.5 h | 86.4 | 13.2 | 5 H | 0.21 nm | 100/100 |
| Si-01 | B | quartz glass | 200° C. | 0.5 h | 93.5 | 6.5 | 2 H | — | — |
| Si-01 | B | quartz glass | 400° C. | 0.5 h | 91.1 | 8.9 | 10 H | — | — |

TABLE 6

| Sample | Rotation Condition | Substrate | Heat Treatment Temperature | Heat Treatment Time | Transmittance (250 nm) |
|---|---|---|---|---|---|
| Ti-01 | A | quartz glass | 120° C. | 0.5 h | 1.0 |
| Ti-01 | A | quartz glass | 150° C. | 0.5 h | 0.2 |
| Ti-01 | A | quartz glass | 200° C. | 0.5 h | 1.3 |
| Ti-01 | A | quartz glass | 400° C. | 0.5 h | 2.4 |
| Ti-01 | A | quartz glass | 700° C. | 0.5 h | 1.8 |

TABLE 7

| Sample | Test Time | Rotation Condition | Substrate | Heat Treatment Temperature | Heat Treatment Time | Film Thickness (nm) | Refractive Index (634 nm) |
|---|---|---|---|---|---|---|---|
| Ti-05 | 0 | B | Corning glass | 200° C. | 0.5 h | 98 | 1.88 |
| Ti-05 | 100 h | B | Corning glass | 200° C. | 0.5 h | 97 | 1.83 |
| Ti-05 | 0 | B | Corning glass | 300° C. | 0.5 h | 69 | 2.07 |
| Ti-05 | 100 h | B | Corning glass | 300° C. | 0.5 h | 77 | 2.01 |
| Ti-05 | 0 | B | Corning glass | 400° C. | 0.5 h | 62 | 2.02 |
| Ti-05 | 100 h | B | Corning glass | 400° C. | 0.5 h | 63 | 2.00 |
| Ti-05 | 0 | B | Corning glass | 700° C. | 0.5 h | 55 | 2.12 |
| Ti-05 | 100 h | B | Corning glass | 700° C. | 0.5 h | 56 | 2.12 |

TABLE 8

| Sample | Test Time | Rotation Condition | Substrate | Heat Treatment Temperature | Heat Treatment Time | Film Thickness (nm) | Refractive Index (634 nm) |
|---|---|---|---|---|---|---|---|
| Ti-05 | 0 | G | Corning glass | 200° C. | 0.5 h | 121 | 1.79 |
| Ti-05 | 5 h | G | Corning glass | 200° C. | 0.5 h | 116 | 1.76 |
| Ti-06 | 24 h | G | Corning glass | 200° C. | 0.5 h | 134 | 1.79 |

TABLE 9

| Sample | Rotation Condition | Substrate | Heat Treatment Temperature | Heat Treatment Time | Etching Speed (nm/min) |
|---|---|---|---|---|---|
| Ti-01 | H | quartz glass | 300° C. | 0.5 h | 24.0 |
| Ti-01 | B | quartz glass | 500° C. | 0.5 h | 9.1 |
| Ti-05 | B | quartz glass | 700° C. | 0.5 h | 9.7 |

TABLE 10

| Sample | Rotation Condition | Substrate | Heat Treatment Temperature | Heat Treatment Time | Etching Amount | Etching Speed |
|---|---|---|---|---|---|---|
| Ti-01 | I | quartz glass | 500° C. | 53 min 20 sec | <10 nm | <0.2 nm/min |
| Ti-01 | I | quartz glass | 700° C. | 52 min 00 sec | <10 nm | <0.2 nm/min |

TABLE 11

| Irradiation Time (h) | Contact Angle (°) |
|---|---|
| 0 | 55.9 |
| 8 | 59.9 |
| 16 | 62.0 |
| 24 | 63.3 |
| 32 | 64.1 |
| 40 | 65.0 |
| 48 | 67.9 |
| 56 | 76.0 |
| 64 | 84.7 |
| 72 | 88.2 |
| 80 | 62.6 |
| 88 | 50.3 |
| 96 | 42.4 |
| 104 | 33.9 |
| 112 | 29.9 |
| 120 | 26.3 |
| 128 | 22.7 |
| 136 | 22.1 |
| 144 | 21.9 |
| 152 | 21.3 |
| 160 | 21.5 |

TABLE 12

| Irradiation Time (h) | Contact Angle (°) |
|---|---|
| 0 | 54.3 |
| 8 | 50.5 |
| 16 | 31.3 |
| 24 | 16.4 |
| 32 | 5.3 |
| 40 | 3.0 |

The "Rotation Condition" in Tables 1 to 10 is the conditions in coating the film-forming material solution on a surface of a substrate by spin coating method and is as follows.

A: The substrate is processed at a rotation speed of 200 rpm for 15 seconds and then processed at 2,000 rpm for 60 seconds.

B: The substrate is processed at a rotation speed of 200 rpm for 15 seconds and then processed at 1,000 rpm for 60 seconds.

C: The substrate is processed at a rotation speed of 200 rpm for 15 seconds and then processed at 5,000 rpm for 60 seconds.

D: The substrate is processed at a rotation speed of 200 rpm for 15 seconds and then processed at 500 rpm for 60 seconds.

E: The substrate is processed at a rotation speed of 500 rpm for 15 seconds and then processed at 2,000 rpm for 30 seconds.

F: The substrate is processed at a rotation speed of 200 rpm for 15 seconds and then processed at 2,000 rpm for 30 seconds.

G: The substrate is processed at a rotation speed of 200 rpm for 15 seconds and then processed at 1,000 rpm for 30 seconds.

H: The substrate is processed at a rotation speed of 500 rpm for 15 seconds and then processed at 2,000 rpm for 60 seconds.

I: The substrate is processed at a rotation speed of 500 rpm for 15 seconds and then processed at 5,000 rpm for 60 seconds.

Reference Example-1

A hexane solution of butyllithium (1.63 M, 101 mL, 165 mmol) was cooled to −70° C. and after adding 17.2 g (165 mmol) of 1,1-dimethyl-2-methoxyethanol and 10 mL of tetrahydrofuran, the system was stirred at room temperature for 13 hours to prepare a 1,1-dimethyl-2-methoxyethyloxy-lithium solution. A toluene solution of titanium tetrachloride (1.01 M, 40.0 mL, 40.4 mmol) was put in another flask and cooled to 0° C., and the 1,1-dimethyl-2-methoxyethyloxy-lithium solution was slowly added. After stirring this mixed solution at room temperature for 24 hours, insoluble matters were separated by filtration, and the filtrate was concentrated under reduced pressure. The resulting concentrate was distilled under reduced pressure (distillation temperature: 122° C., pressure: $1.2 \times 10^2$ Pa), whereby tetrakis(1,1-dimethyl-2-methoxyethyloxy)titanium(Ti(OCMe$_2$CH$_2$OMe)$_4$) was obtained as a colorless liquid. Yield: 16.9 g (percentage yield: 91%).

$^1$H NMR (500 MHz, C$_6$D$_6$) δ 3.31 (s, 8H), 3.25 (s, 12H), 1.46 (s, 24H). $^{13}$C NMR (125 MHz, C$_6$D$_6$) δ 82.6, 82.0, 59.3, 28.4.

Example-61

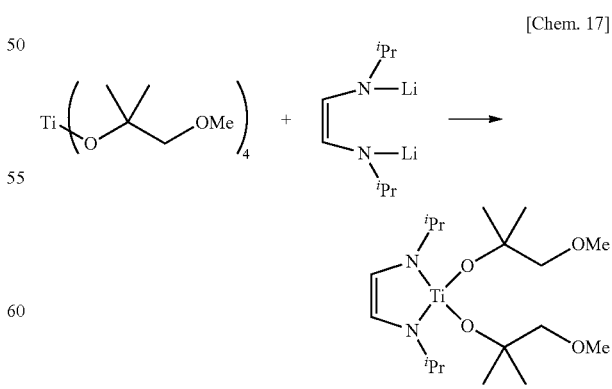

[Chem. 17]

1.80 g (12.8 mmol) of N,N'-diisopropyl-1,4-diaza-1,3-butadiene ($^i$PrN=CHCH=N$^i$Pr) was dissolved in a mixture of 10 mL of tetrahydrofuran and 5 mL of hexane and after adding 187 mg (26.9 mmol) of lithium, the system was stirred at room temperature for 14 hours to prepare a vinylenediamide alkali metal salt solution. In another flask, a solution obtained by diluting 5.60 g (12.2 mmol) of Ti(OCMe$_2$CH$_2$OMe)$_4$ obtained in Reference Example-1 with 15 mL of hexane was prepared and cooled to 0° C., and the vinylenediamide alkali metal salt solution was slowly added. After stirring this mixed solution at room temperature for 7 hours, 2.80 g (25.8 mmol) of chlorotrimethylsilane was added, and the system was stirred for 10 hours. The produced insoluble matters were separated by filtration, and the filtrate was concentrated under reduced pressure. The resulting concentrate was distilled under reduced pressure (distillation temperature: 115° C., pressure: 9.3×10$^1$ Pa), whereby (N,N'-diisopropyl-1,2-vinylenediamide-κ$^2$N,N')bis(1,1-dimethyl-2-methoxyethyloxo)titanium(Ti($^i$PrNCH=CHN$^i$Pr)(OCMe$_2$CH$_2$OMe)$_2$) was obtained as a dark red liquid. Yield: 3.69 g (percentage yield: 77%).

$^1$H NMR (500 MHz, C$_6$D$_6$) δ 5.80 (s, 2H), 3.60 (sept, J=6 Hz, 2H), 3.24 (s, 4H), 3.21 (s, 6H), 1.40 (s, 12H), 1.27 (d, J=6 Hz, 12H). $^{13}$C NMR (125 MHz, C$_6$D$_6$) δ 105.6, 83.5, 80.9, 59.3, 56.8, 29.3, 25.8.

Example-62

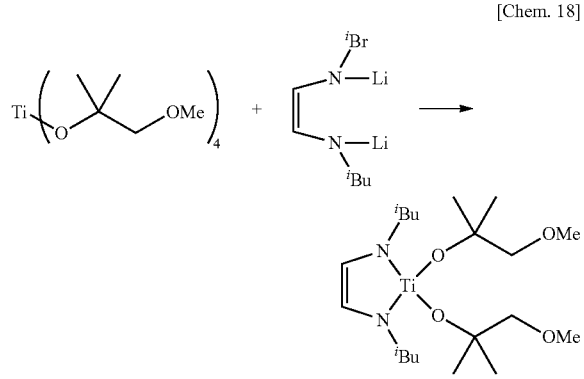

[Chem. 18]

2.05 g (12.2 mmol) of N,N'-di(tert-butyl)-1,4-diaza-1,3-butadiene ($^t$BuN=CHCH=N$^t$Bu) was dissolved in a mixture of 5 mL of tetrahydrofuran and 15 mL of hexane and after adding 178 mg (25.6 mmol) of lithium, the system was stirred at room temperature for 14 hours to prepare a vinylenediamide alkali metal salt solution. In another flask, a solution obtained by diluting 5.60 g (12.2 mmol) of Ti(OCMe$_2$CH$_2$OMe)$_4$ obtained in Reference Example-1 with 15 mL of hexane was prepared and cooled to 0° C., and the vinylenediamide alkali metal salt solution was slowly added. After stirring this mixed solution at room temperature for 7 hours, 2.65 g (24.4 mmol) of chlorotrimethylsilane was added, and the system was stirred for 10 hours. The produced insoluble matters were separated by filtration, and the filtrate was concentrated under reduced pressure. The resulting concentrate was distilled under reduced pressure (distillation temperature: 112° C., pressure: 1.2×10$^2$ Pa), whereby (N,N'-di-tert-butyl-1,2-vinylenediamide-κ$^2$N,N')bis(1,1-dimethyl-2-methoxyethyloxo)titanium(Ti($^t$BuNCH=CHN$^t$Bu)(OCMe$_2$CH$_2$OMe)$_2$) was obtained as a dark red liquid. Yield: 4.96 g (percentage yield: 96%).

$^1$H NMR (500 MHz, C$_6$D$_6$) δ 5.94, (s, 2H), 3.80-2.80 (br, 4H), 3.21 (br, s, 6H), 2.00-0.90 (br, 12H), 1.31 (s, 18H). $^{13}$C NMR (125 MHz, C$_6$D$_6$) δ 103.0, 83.4, 80.9 (br), 59.3, 57.5, 31.8, 29.3.

Example-63

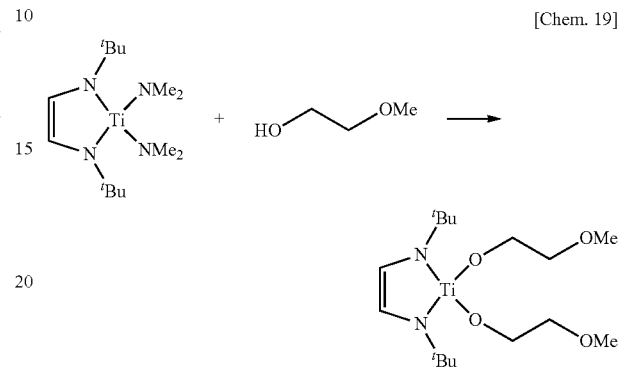

[Chem. 19]

A solution obtained by dissolving 4.17 g (13.7 mmol) of (N,N'-di-tert-butyl-1,2-vinylenediamide-κ$^2$N,N')bis(dimethylamide)titanium(Ti($^t$BuNCH=CHN$^t$Bu)(NMe$_2$)$_2$) in 20 mL of hexane was cooled to −70° C., and 2.09 g (27.5 mmol) of 2-methoxyethanol was slowly added with stirring. This mixed solution was stirred at room temperature for 4 hours and concentrated under reduced pressure. The resulting concentrate was distilled under reduced pressure (distillation temperature: 120° C., pressure: 1.3×10$^2$ Pa), whereby (N,N'-di-tert-butyl-1,2-vinylenediamide-κ$^2$N,N')bis(2-methoxyethyloxo)titanium(Ti($^t$BuNCH=CHN$^t$Bu)(OCH$_2$CH$_2$OMe)$_2$) was obtained as a dark red liquid. Yield: 4.73 g (percentage yield: 94%).

$^1$H NMR (500 MHz, C$_6$D$_6$) δ 6.01 (s, 2H), 4.30-3.70 (br, 4H), 3.39 (br, s, 4H), 3.18 (s, 6H), 1.30 (s, 18H). $^{13}$C NMR (125 MHz, C$_6$D$_6$) δ 102.3, 76.0, 71.9 (br), 76.0, 58.5, 58.4, 31.5.

Example-64

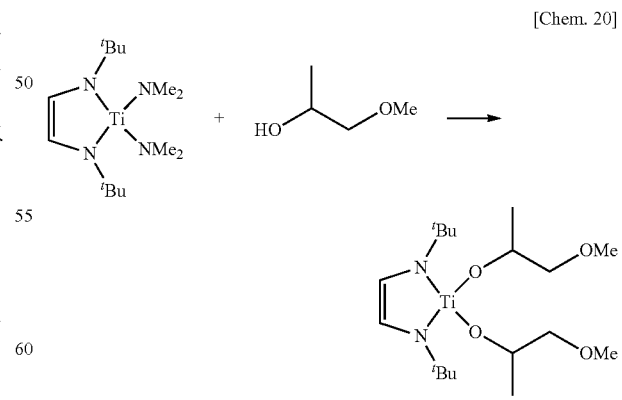

[Chem. 20]

A solution obtained by dissolving 6.01 g (19.7 mmol) of Ti($^t$BuNCH=CHN$^t$Bu)(NMe$_2$)$_2$ in 15 mL of hexane was cooled to −70° C., and 3.57 g (39.6 mmol) of 1-methoxy-2-propanol was slowly added with stirring. This mixed solution was stirred at room temperature for 6 hours and concentrated under reduced pressure. The resulting concentrate was distilled under reduced pressure (distillation temperature: 107° C., pressure: 1.0×10² Pa), whereby (N,N'-di-tert-butyl-1,2-vinylenediamide-κ²N,N')bis(1-methyl-2-methoxyethyloxo)titanium(Ti(ᵗBuNCH=CHNᵗBu)(OCHMeCH₂OMe)₂) was obtained as a dark red liquid. Yield: 6.87 g (percentage yield: 88%).

¹H NMR (500 MHz, C₆D₆) δ 5.98 (s, 2H), 5.20-3.90 (br, 2H), 3.60-3.10 (br, 4H), 3.19 (s, 6H), 1.31 (s, 18H), 1.40-1.15 (br, 6H). ¹³C NMR (125 MHz, C₆D₆) δ 102.6, 102.53, 102.49, 80.2, 76.7 (br), 58.9, 58.03, 57.98, 57.92, 31.6, 23.0.

Example-65

[Chem. 21]

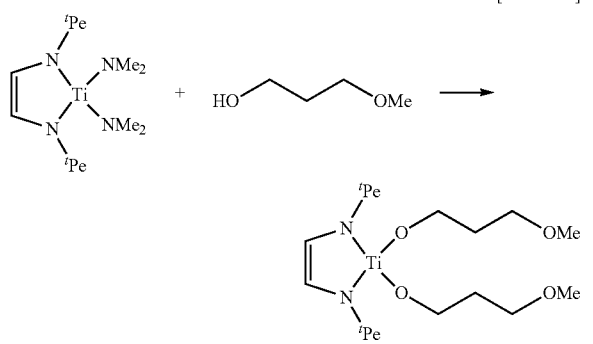

A solution obtained by dissolving 5.10 g (15.3 mmol) of (N,N'-di-tert-pentyl-1,2-vinylenediamide-κ²N,N')bis(dimethylamide)titanium Ti(ᵗPeNCH=CHNᵗPe)(NMe₂)₂ in 20 mL of hexane was cooled to −70° C., and 2.77 g (30.7 mmol) of 3-methoxypropanol was slowly added with stirring. This mixed solution was stirred at room temperature for 17 hours and concentrated under reduced pressure. The resulting concentrate was distilled under reduced pressure (distillation temperature: 134° C., pressure: 1.0×10² Pa), whereby (N,N'-di-tert-pentyl-1,2-vinylenediamide-κ²N,N')bis(3-methoxypropyloxo)titanium(Ti(ᵗPeNCH=CHNᵗPe)(OCH₂CH₂CH₂OMe)₂) was obtained as a dark red liquid. Yield: 5.45 g (percentage yield: 84%).

¹H NMR (500 MHz, C₆D₆) δ 5.91 (s, 2H), 5.00-3.60 (br, 4H), 3.60-3.35 (br, 4H), 3.16 (s, 6H), 2.20-1.60 (br, 4H), 1.53 (q, J=7 Hz, 4H), 1.24 (s, 12H), 0.79 (t, J=7 Hz, 6H). ¹³C NMR (125 MHz, C₆D₆) δ 102.2, 70.6 (br), 70.0, 60.9, 58.7, 36.6, 35.5, 29.1 (br), 9.2.

Example-66

[Chem. 22]

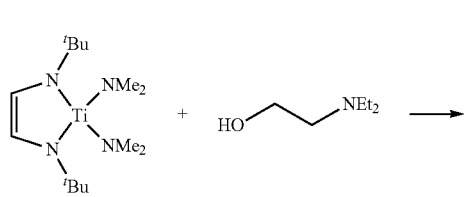

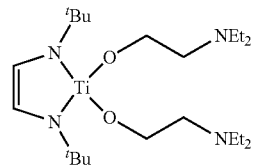

A solution obtained by dissolving 6.07 g (20.0 mmol) of Ti(ᵗBuNCH=CHNᵗBu)(NMe₂)₂ in 15 mL of hexane was cooled to −70° C., and 4.68 g (40.0 mmol) of 2-(diethylamino)ethanol was slowly added with stirring. This mixed solution was stirred at room temperature for 14 hours and concentrated under reduced pressure. The resulting concentrate was distilled under reduced pressure (distillation temperature: 143° C., pressure: 1.2×10² Pa), whereby (N,N'-di-tert-butyl-1,2-vinylenediamide-κ²N,N')bis(2-(diethylamino)ethyloxo)titanium(Ti(ᵗBuNCH=CHNᵗBu)(OCH₂CH₂NEt₂)₂) was obtained as a dark red liquid. Yield: 6.20 g (percentage yield: 69%).

¹H NMR (500 MHz, C₆D₆) δ 6.02 (s, 2H), 5.30-3.60 (br, 4H), 2.70 (br, 4H), 2.49 (q, J=7 Hz, 8H), 1.31 (s, 18H), 0.99 (t, J=7 Hz, 12H). ¹³C NMR (125 MHz, C₆D₆) δ 102.4, 72.5 (br), 58.2, 58.0, 48.5, 31.6, 12.9.

Example-67

[Chem. 23]

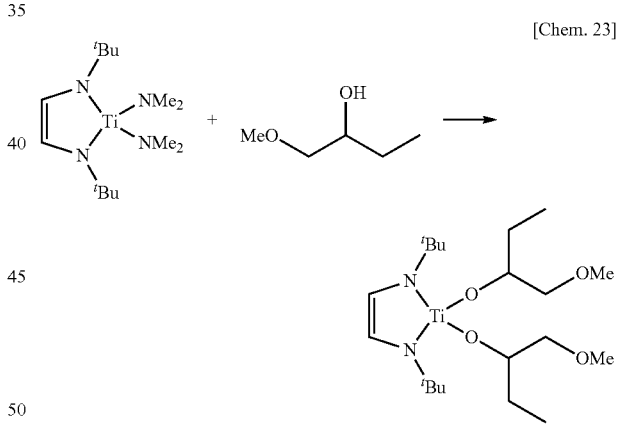

A solution obtained by dissolving 3.83 g (12.6 mmol) of Ti(ᵗBuNCH=CHNᵗBu)(NMe₂)₂ in 18 mL of hexane was cooled to −70° C., and 2.62 g (25.2 mmol) of 1-methoxy-2-butanol was slowly added with stirring. This mixed solution was stirred at room temperature for 18 hours and concentrated under reduced pressure. The resulting concentrate was distilled under reduced pressure (distillation temperature: 120-124° C., pressure: 1.2×10² Pa), whereby (N,N'-di-tert-butyl-1,2-vinylenediamide-κ²N,N')bis(1-ethyl-2-methoxyethyloxo)titanium(Ti(ᵗBuNCH=CHNᵗBu)(OCHEtCH₂OMe)₂) was obtained as a dark red liquid. Yield: 3.95 g (percentage yield: 74%).

¹H NMR (500 MHz, C₆D₆) δ 5.98 (s, 2H), 4.80-3.80 (br, 2H), 3.60-3.00 (br, 4H), 3.19 (s, 6H), 1.85-1.35 (br, 4H), 1.31

(s, 18H), 1.13-0.93 (br, 6H). $^{13}$C NMR (125 MHz, C$_6$D$_6$) δ 102.62, 102.56, 102.51, 78.8, 59.0, 58.1, 31.5, 29.43, 29.40, 10.7.

Example-68

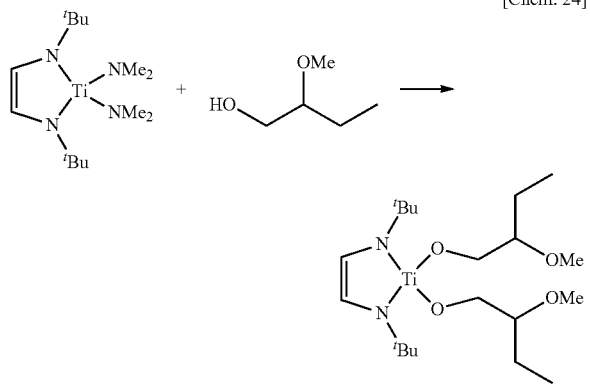

[Chem. 24]

A solution obtained by dissolving 4.11 g (13.5 mmol) of Ti($^t$BuNCH=CHN$^t$Bu)(NMe$_2$)$_2$ in 20 mL of hexane was cooled to −70° C., and 2.82 g (27.1 mmol) of 2-methoxy-1-butanol was slowly added with stirring. This mixed solution was stirred at room temperature for 18 hours and concentrated under reduced pressure. The resulting concentrate was distilled under reduced pressure (distillation temperature: 124-127° C., pressure: 8.6×10$^1$ Pa), whereby (N,N'-di-tert-butyl-1,2-vinylenediamide-κ$^2$N,N')bis(2-methoxybutyloxo)titanium(Ti($^t$BuNCH=CHN$^t$Bu)(OCH$_2$CH(OMe)CH$_2$CH$_3$)$_2$) was obtained as a dark red liquid. Yield: 4.97 g (percentage yield: 87%).

$^1$H NMR (500 MHz, C$_6$D$_6$) δ 6.01 (s, 2H), 4.80-3.80 (br, 4H), 3.55-3.00 (br, 2H), 3.29 (s, 6H), 1.80-1.45 (br, 4H), 1.30 (s, 18H), 0.98 (br, t, J=7 Hz, 6H). $^{13}$C NMR (125 MHz, C$_6$D$_6$) δ 102.4, 102.3, 102.2, 84.6, 58.5, 57.4, 31.5, 24.5, 10.2.

Example-69

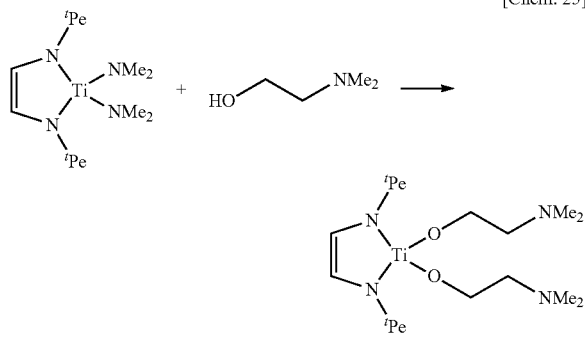

[Chem. 25]

A solution obtained by dissolving 5.56 g (16.7 mmol) of Ti($^t$PeNCH=CHN$^t$Pe)(NMe$_2$)$_2$ in 25 mL of hexane was cooled to −70° C., and 3.00 g (33.7 mmol) of 2-(diethylamino)ethanol was slowly added with stirring. This mixed solution was stirred at room temperature for 14 hours and concentrated under reduced pressure. The resulting concentrate was distilled under reduced pressure (distillation temperature: 140° C., pressure: 8.0×10$^1$ Pa), whereby (N,N'-di-tert-pentyl-1,2-vinylenediamide-κ$^2$N,N')bis(2-(dimethylamino)ethyloxo)titanium(Ti($^t$PeNCH=CHN$^t$Pe)(OCH$_2$CH$_2$NMe$_2$)$_2$) was obtained as a dark red liquid. Yield: 6.22 g (percentage yield: 89%).

$^1$H NMR (500 MHz, C$_6$D$_6$) δ 5.96 (s, 2H), 5.10-3.40 (br, 4H), 3.00-2.00 (br, 4H), 2.17 (s, 12H), 1.57 (q, J=7 Hz, 4H), 1.29 (s, 12H), 0.80 (t, J=7 Hz, 6H). $^{13}$C NMR (125 MHz, C$_6$D$_6$) δ 102.7, 71.8 (br), 61.0, 46.5, 36.9, 28.8 (br), 9.3.

Example-70

In an argon atmosphere, 1.83 g (5.00 mmol) of Ti($^t$BuNCH=CHN$^t$Bu)(OCH$_2$CH$_2$OMe)$_2$ obtained in Example-63 and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at 80° C. for 6 hours while keeping the connection of the balloon to the Schlenk tube, the inside of the Schlenk was depressurized to 10 Pa under heating at 80° C. to obtain Film-Forming Material 7 as a red-brown solid. Yield: 1.36 g. Film-Forming Material 7 (1.36 g) was dissolved in 5 mL of ethylene glycol monomethyl ether, and the resulting solution was passed through a syringe filter (SLLGM25NS, manufactured by Millpore, pore size: 0.20 μm) to remove insoluble matters by filtration, whereby Film-Forming Material Solution Ti-10 was obtained.

Example-71

In an argon atmosphere, 1.83 g (4.36 mmol) of Ti($^t$PeNCH=CHN$^t$Pe)(OCH$_2$CH$_2$NMe$_2$)$_2$ obtained in Example-69 and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at 80° C. for 16 hours while keeping the connection of the balloon to the Schlenk tube, the inside of the Schlenk was depressurized to 10 Pa under heating at 80° C. to obtain Film-Forming Material 8 as a brown solid. Yield: 802 mg. Film-Forming Material 8 (802 mg) was dissolved in 7.5 mL of ethylene glycol monomethyl ether, and the resulting solution was passed through a syringe filter (SLLGM25NS, manufactured by Millpore, pore size: 0.20 μm) to remove insoluble matters by filtration, whereby Film-Forming Material Solution Ti-11 was obtained.

Example-72

In an argon atmosphere, 2.96 g (7.02 mmol) of Ti($^t$BuNCH=CHN$^t$Bu)(OCMe$_2$CH$_2$OMe)$_2$ obtained in Example-62 and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at 80° C. for 72 hours while keeping the connection of the balloon to the Schlenk tube, the inside of the Schlenk was depressurized to 10 Pa under heating at 80° C. to obtain Film-Forming Material 9 as a brown solid. Yield: 1.41 g. Film-Forming Material 9 (1.31 g) was dissolved in 12 mL of ethylene glycol monomethyl ether, and the resulting solution was passed through a syringe filter (SLLGM25NS, manufactured by Millpore, pore size: 0.20 µm) to remove insoluble matters by filtration, whereby Film-Forming Material Solution Ti-12 was obtained.

Reference Example-2

A hexane solution of butyllithium (1.63 M, 190 mL, 310 mmol) was cooled to −70° C. and after adding 23.6 g (310 mmol) of 2-methoxyethanol and 20 mL of tetrahydrofuran, the system was stirred at room temperature for 12 hours to prepare a 2-methoxyethyloxylithium solution. In another flask, a solution obtained by diluting 12.8 g (75.3 mmol) of silicon tetrachloride with 50 mL of hexane was prepared and cooled to −70° C., and the 2-methoxyethyloxylithium solution was slowly added. After stirring this mixed solution at room temperature for 9 hours, insoluble matters were separated by filtration, and the filtrate was concentrated under reduced pressure. The resulting concentrate was distilled under reduced pressure (distillation temperature: 110° C., pressure: $8.0 \times 10^1$ Pa), whereby tetrakis(2-methoxyethyloxy)silane(Si(OCH$_2$CH$_2$OMe)$_4$) was obtained as a colorless liquid. Yield: 22.5 g (percentage yield: 91%).

$^1$H NMR (500 MHz, C$_6$D$_6$) δ 4.02 (t, J=5 Hz, 8H), 3.37 (t, J=5 Hz, 8H), 3.13 (s, 12H). $^{13}$C NMR (125 MHz, C$_6$D$_6$) 74.0, 63.4, 58.8.

Reference Example-3

A hexane solution of butyllithium (1.63 M, 172 mL, 280 mmol) was cooled to −70° C. and after adding 33.2 g (281 mmol) of 2-tert-butoxyethanol and 10 mL of tetrahydrofuran, the system was stirred at room temperature for 12 hours to prepare a 2-tert-butoxyethyloxylithium solution. In another flask, a solution obtained by diluting 11.7 g (68.9 mmol) of silicon tetrachloride with 50 mL of hexane was prepared and cooled to −70° C., and the 2-tert-butoxyethyloxylithium solution was slowly added. After stirring this mixed solution at room temperature for 9 hours, insoluble matters were separated by filtration, and the filtrate was concentrated under reduced pressure. The resulting concentrate was distilled under reduced pressure (distillation temperature: 151° C., pressure: $8.8 \times 10^1$ Pa), whereby tetrakis(2-tert-butoxyethyloxy)silane (Si(OCH$_2$CH$_2$O$^t$Bu)$_4$) was obtained as a colorless liquid. Yield: 25.7 g (percentage yield: 75%).

$^1$H NMR (500 MHz, C$_6$D$_6$) δ 4.13 (t, J=5 Hz, 8H), 3.49 (t, J=5 Hz, 8H), 1.12 (s, 36H). $^{13}$C NMR (125 MHz, C$_6$D$_6$) δ 72.7, 64.2, 63.4, 27.9.

Reference Example-4

A hexane solution of butyllithium (1.63 M, 230 mL, 375 mmol) was cooled to −70° C. and after adding 33.8 g (375 mmol) of 3-methoxypropanol and 10 mL of tetrahydrofuran, the system was stirred at room temperature for 12 hours to prepare a 3-methoxypropyloxylithium solution. In another flask, a solution obtained by diluting 15.7 g (92.4 mmol) of silicon tetrachloride with 30 mL of hexane was prepared and cooled to −70° C., and the 3-methoxypropyloxylithium solution was slowly added. After stirring this mixed solution at room temperature for 18 hours, insoluble matters were separated by filtration, and the filtrate was concentrated under reduced pressure. The resulting concentrate was distilled under reduced pressure (distillation temperature: 122° C., pressure: $1.0 \times 10^2$ Pa), whereby tetrakis(3-methoxypropyloxy)silane(Si(OCH$_2$CH$_2$CH$_2$OMe)$_4$) was obtained as a colorless liquid. Yield: 26.4 g (percentage yield: 74%).

$^1$H NMR (500 MHz, C$_6$D$_6$) δ 4.00 (t, J=6 Hz, 8H), 3.36 (t, J=6 Hz, 8H), 3.11 (s, 12H), 1.86 (quint, J=6 Hz, 8H). $^{13}$C NMR (125 MHz, C$_6$D$_6$) δ 69.5, 61.1, 58.6, 33.3.

Reference Example-5

21.6 g (142 mmol) of tetramethoxysilane and 63.2 g (709 mmol) of 2-(dimethylamino)ethanol were charged in a flask with a Dean-Stark trap and stirred for 20 hours while dipping the flask in an oil bath at 120° C. During this time, 14.2 g of methanol produced was collected through the Dean-Stark trap. Thereafter, 15.4 g (173 mmol) of 2-(dimethylamino)ethanol was added, and the system was stirred for 17 hours while dipping the flask in an oil bath at 140° C. The reaction solution was distilled under reduced pressure (distillation temperature: 119° C., pressure: $6.7 \times 10^1$ Pa), whereby tetrakis(2-(dimethylamino)ethyloxy)silane(Si(OCH$_2$CH$_2$NMe$_2$)$_4$) was obtained as a colorless liquid. Yield: 34.4 g (percentage yield: 64%).

$^1$H NMR (500 MHz, C$_6$D$_6$) δ 4.06 (t, J=6 Hz, 8H), 2.52 (t, J=6 Hz, 8H), 2.15 (s, 24H). $^{13}$C NMR (125 MHz, C$_6$D$_6$) δ 62.6, 61.8, 46.3.

Example-73

[Chem. 26]

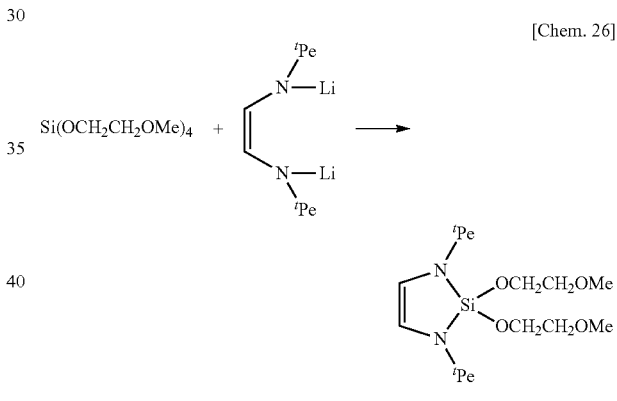

5.17 g (26.3 mmol) of N,N'-di-tert-pentyl-1,4-diaza-1,3-butadiene ($^t$PeNCH=CHN$^t$Pe) obtained in Reference Example-2 was dissolved in a mixture of 10 mL of tetrahydrofuran and 30 mL of hexane and after adding 384 mg (55.3 mmol) of lithium, the system was stirred at room temperature for 14 hours to prepare a vinylenediamide alkali metal salt solution. In another flask, a solution obtained by diluting 8.65 g (26.3 mmol) of Si(OCH$_2$CH$_2$OMe)$_4$ with 20 mL of hexane was prepared, and the vinylenediamide alkali metal salt solution was slowly added. This mixed solution was refluxed for 6 hours and then cooled to room temperature, and after adding 5.72 g (52.7 mmol) of chlorotrimethylsilane, the system was stirred for 12 hours. The produced insoluble matters were separated by filtration, and the filtrate was concentrated under reduced pressure. The resulting concentrate was distilled under reduced pressure (distillation temperature: 119° C., pressure: $1.4 \times 10^2$ Pa), whereby (N,N'-di-tert-pentyl-1,2-vinylenediamide-κ$^2$N,N')bis(2-methoxyethyloxo)silane(Si($^t$PeNCH=CHN$^t$Pe)(OCH$_2$CH$_2$OMe)$_2$) was obtained as a pale yellow liquid. Yield: 9.21 g (percentage yield: 93%).

$^1$H NMR (500 MHz, C$_6$D$_6$) δ 5.72 (d, J=2 Hz, 2H), 3.93 (m, 4H), 3.39 (t, J=5 Hz, 4H), 3.13 (s, 6H), 1.56 (q, J=7 Hz, 4H), 1.31 (s, 12H), 0.91 (t, J=7 Hz, 6H). $^{13}$C NMR (125 MHz, C$_6$D$_6$) δ 110.4, 74.0, 63.1, 58.9, 53.7, 35.4, 28.1, 9.4.

Example-74

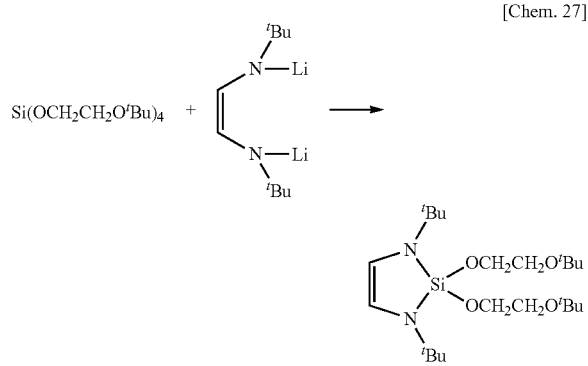

[Chem. 27]

3.91 g (23.2 mmol) of N,N'-di-tert-butyl-1,4-diaza-1,3-butadiene ($^t$BuNCH=CHN$^t$Bu) obtained in Reference Example-3 was dissolved in a mixture of 10 mL of tetrahydrofuran and 30 mL of hexane and after adding 338 mg (48.7 mmol) of lithium, the system was stirred at room temperature for 14 hours to prepare a vinylenediamide alkali metal salt solution. In another flask, a solution obtained by diluting 11.53 g (23.2 mmol) of Si(OCH$_2$CH$_2$O$^t$Bu)$_4$ with 10 mL of hexane was prepared, and the vinylenediamide alkali metal salt solution was slowly added. This mixed solution was refluxed for 2 hours and then cooled to room temperature, and after adding 5.04 g (46.4 mmol) of chlorotrimethylsilane, the system was stirred for 6 hours. The produced insoluble matters were separated by filtration, and the filtrate was concentrated under reduced pressure. The resulting concentrate was distilled under reduced pressure (distillation temperature: 140° C., pressure: 1.0×10$^2$ Pa), whereby (N,N'-di-tert-butyl-1,2-vinylenediamide-κ$^2$N,N')bis(2-tert-butylethyloxy)silane (Si($^t$BuNCH=CHN$^t$Bu)(OCH$_2$CH$_2$O$^t$Bu)$_2$) was obtained as a pale yellow liquid. Yield: 8.60 g (percentage yield: 86%).

$^1$H NMR (500 MHz, C$_6$D$_6$) δ 5.81 (s, 2H), 3.94 (t, J=6 Hz, 4H), 3.47 (t, J=6 Hz, 4H), 1.37 (s, 18H), 1.10 (s, 18H). $^{13}$C NMR (125 MHz, C$_6$D$_6$) δ 110.8, 72.7, 63.6, 63.2, 51.1, 30.9, 27.8.

Example-75

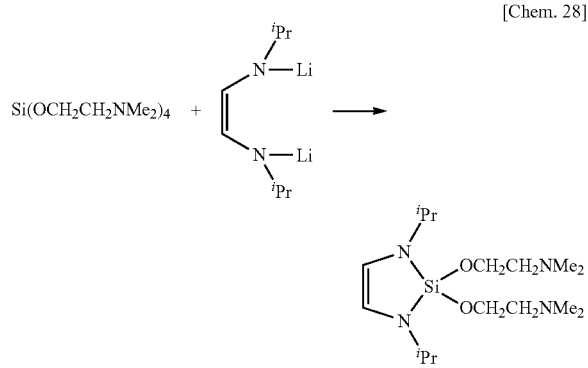

[Chem. 28]

2.09 g (14.9 mmol) of N,N'-diisopropyl-1,4-diaza-1,3-butadiene ($^i$PrNCH=CHN$^i$Pr) obtained in Reference Example-5 was dissolved 15 mL of tetrahydrofuran and after adding 217 mg (31.3 mmol) of lithium, the system was stirred at room temperature for 14 hours to prepare a vinylenediamide alkali metal salt solution. In another flask, a solution obtained by diluting 5.68 g (14.9 mmol) of Si(OCH$_2$CH$_2$NMe$_2$)$_4$ with 20 mL of hexane was prepared, and the vinylenediamide alkali metal salt solution was slowly added. This mixed solution was stirred at room temperature for 8 hours, and after adding 3.24 g (29.8 mmol) of chlorotrimethylsilane, the system was stirred for 19 hours. The produced insoluble matters were separated by filtration, and the filtrate was concentrated under reduced pressure. The resulting concentrate was distilled under reduced pressure (distillation temperature: 112° C., pressure: 9.6×10$^3$ Pa), whereby (N,N'-diisopropyl-1,2-vinylenediamide-κ$^2$N,N')bis(2-dimethylaminoethyloxy)silane(Si($^i$PrNCH=CHN$^i$Pr)(OCH$_2$CH$_2$NMe$_2$)$_2$) was obtained as a pale yellow liquid. Yield: 4.27 g (percentage yield: 83%).

$^1$H NMR (500 MHz, C$_6$D$_6$) δ 5.68 (s, 2H), 3.93 (t, J=6 Hz, 4H), 3.38 (sept, J=7 Hz, 2H), 2.49 (t, J=6 Hz, 4H), 2.13 (s, 12H), 1.25 (d, J=7 Hz, 12H). $^{13}$C NMR (125 MHz, C$_6$D$_6$) δ 112.8, 62.3, 61.8, 47.5, 46.4, 24.4.

Example-76

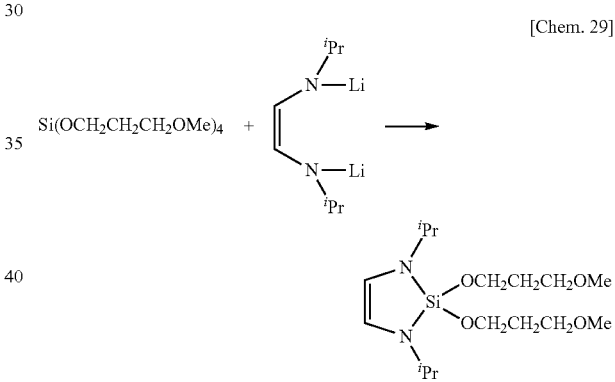

[Chem. 29]

2.38 g (17.0 mmol) of N,N'-diisopropyl-1,4-diaza-1,3-butadiene ($^i$PrNCH=CHN$^i$Pr) obtained in Reference Example-4 was dissolved 20 mL of tetrahydrofuran and after adding 243 mg (35.0 mmol) of lithium, the system was stirred at room temperature for 14 hours to prepare a vinylenediamide alkali metal salt solution. In another flask, a solution obtained by diluting 6.40 g (16.6 mmol) of Si(OCH$_2$CH$_2$CH$_2$OMe)$_4$ with 20 mL of hexane was prepared, and the vinylenediamide alkali metal salt solution was slowly added. This mixed solution was stirred at room temperature for 14 hours, and after adding 3.62 g (33.3 mmol) of chlorotrimethylsilane, the system was stirred for 10 hours. The produced insoluble matters were separated by filtration, and the filtrate was concentrated under reduced pressure. The resulting concentrate was distilled under reduced pressure (distillation temperature: 109° C., pressure: 9.6×10$^1$ Pa), whereby (N,N'-diisopropyl-1,2-vinylenediamide-κ$^2$N,N')bis(3-methoxypropyloxy)silane(Si($^i$PrNCH=CHN$^i$Pr)(OCH$_2$CH$_2$CH$_2$OMe)$_2$) was obtained as a pale yellow liquid. Yield: 5.14 g (percentage yield: 89%).

$^1$H NMR (500 MHz, C$_6$D$_6$) δ 5.66 (s, 2H), 3.90 (t, J=6 Hz, 4H), 3.35 (t, J=6 Hz, 4H), 3.34 (sept, J=6 Hz, 2H), 3.09 (s, 6H), 1.85 (quint, J=6 Hz, 4H), 1.22 (d, J=7 Hz, 12H). $^{13}$C NMR (125 MHz, C$_6$D$_6$) δ 112.9, 69.6, 60.7, 58.6, 47.5, 33.2, 24.3.

Example-77

A toluene 20 ml solution containing 2.1 g (6.09 mmol) of Si($^i$PrNCH=CHN$^i$Pr)(OCH$_2$CH$_2$NMe$_2$)$_2$ obtained in Example-75 was prepared in an argon atmosphere. A Teflon (registered trademark) tube connected to a mixed gas of oxygen and argon (oxygen: 20 vol %, produced by Tomoe Shokai Co., Ltd.) was dipped in this solution, and the system was stirred by flowing the mixed gas at a flow rate of 100 ml/min. After stirring for 12 hours, the tip of the Teflon (registered trademark) tube was pulled out from the solution, and the solution was cooled to room temperature. The cooled solution was concentrated under reduced pressure at room temperature, and by reducing the pressure to 10 Pa under heating at 80° C., 1.2 g of a black liquid was collected. Thereafter, 1.2 g of the black liquid was dissolved in 3.7 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Si-03 was obtained.

Example-78

A toluene 20 ml solution containing 2.3 g (6.14 mmol) of Si($^t$PeNCH=CHN$^t$Pe)(OCH$_2$CH$_2$OMe)$_2$ obtained in Example-73 was prepared in an argon atmosphere. A Teflon (registered trademark) tube connected to a mixed gas of oxygen and argon (oxygen: 20 vol %, produced by Tomoe Shokai Co., Ltd.) was dipped in this solution, and the system was stirred by flowing the mixed gas at a flow rate of 100 ml/min. After stirring for 12 hours, the tip of the Teflon (registered trademark) tube was pulled out from the solution, and the solution was cooled to room temperature. The cooled solution was concentrated under reduced pressure at room temperature, and by reducing the pressure to 10 Pa under heating at 80° C., 1.2 g of a light yellow liquid was collected. Thereafter, 1.2 g of the light yellow liquid was dissolved in 4.0 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Si-04 was obtained.

Examples-79 to 94

Each of Film-Forming Material Solutions Ti-10, Ti-11, Ti-12, Si-03 and Si-04 obtained by the methods described in Example-70 to Example-72, Example-77 and Example-78 was coated on a surface of a substrate by spin coating method, and the substrate was heat-treated to produce a titanium oxide film. Evaluation results of the obtained titanium oxide films are shown in Table 13. The film thickness and refractive index were determined by performing multilayer film analysis of the spectrum at a wavelength of 300 to 800 nm measured by means of an ellipsometer (MEL-30S, manufactured by JASCO Corporation).

TABLE 13

| Example | Sample | Rotation Condition | Substrate | Heat Treatment Temperature | Heat Treatment Time | Film Thickness (nm) | Refractive Index (634 nm) |
|---|---|---|---|---|---|---|---|
| Example-79 | Ti-10 | A | Corning glass | 200° C. | 0.5 h | 129 | 1.79 |
| Example-80 | Ti-10 | A | Corning glass | 400° C. | 0.5 h | 77 | 2.00 |
| Example-81 | Ti-10 | A | Corning glass | 700° C. | 0.5 h | 63 | 2.00 |
| Example-82 | Ti-11 | A | Corning glass | 120° C. | 0.5 h | 92 | 1.68 |
| Example-83 | Ti-11 | A | Corning glass | 200° C. | 0.5 h | 71 | 1.79 |
| Example-84 | Ti-11 | A | Corning glass | 400° C. | 0.5 h | 39 | 2.03 |
| Example-85 | Ti-11 | A | Corning glass | 700° C. | 0.5 h | 33 | 2.11 |
| Example-86 | Ti-12 | B | Corning glass | 120° C. | 0.5 h | 104 | 1.72 |
| Example-87 | Ti-12 | B | Corning glass | 150° C. | 0.5 h | 101 | 1.75 |
| Example-88 | Ti-12 | B | Corning glass | 200° C. | 0.5 h | 102 | 1.77 |
| Example-89 | Ti-12 | B | Corning glass | 300° C. | 0.5 h | 68 | 1.95 |
| Example-90 | Ti-12 | B | Corning glass | 400° C. | 0.5 h | 57 | 2.00 |
| Example-91 | Ti-12 | B | Corning glass | 700° C. | 0.5 h | 60 | 2.00 |
| Example-92 | Si-03 | C | Si wafer | 200° C. | 0.5 h | 298 | 1.42 |
| Example-93 | Si-03 | C | Si wafer | 400° C. | 0.5 h | 277 | 1.40 |
| Example-94 | Si-04 | C | Si wafer | 400° C. | 0.5 h | 296 | 1.45 |

The rotation condition in Table 13 is as follows.
A: The substrate is processed at a rotation speed of 200 rpm for 15 seconds and then processed at 1,000 rpm for 60 seconds.
B: The substrate is processed at a rotation speed of 200 rpm for 15 seconds and then processed at 2,000 rpm for 60 seconds.
C: The substrate is processed at a rotation speed of 500 rpm for 15 seconds and then processed at 2,000 rpm for 30 seconds.

Example-95

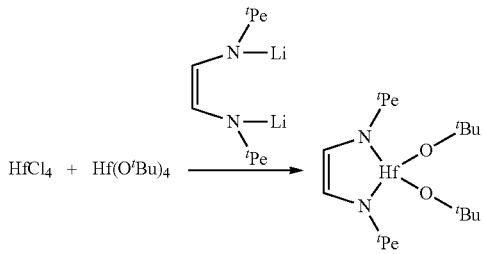

8.39 g (42.7 mmol) of N,N-di-tert-pentyl-1,4-diaza-1,3-butadiene was dissolved in 80 mL of tetrahydrofuran, and 622 mg (89.3 mmol) of lithium was added. After stirring at room temperature for 14 hours, the solvent was removed under reduced pressure, and the remaining solid was dissolved in 50 mL of toluene to prepare a toluene solution of (N,N'-di-tert-pentyl-1,2-vinylenediamide)dilithium. On the other hand, 6.83 g (21.3 mmol) of hafnium tetrachloride was suspended in a mixed solvent of 60 mL of diethyl ether and 20 mL of tetrahydrofuran, and 10.05 g (21.3 mmol) of tetra(tert-butoxo)hafnium was added. After stirring at room temperature for 14 hours, the solvent was removed under reduced pressure from the reaction solution, and 80 mL of toluene was added. The solution was cooled to −70° C. by using a dry ice-methanol bath, and the toluene solution of (N,N'-di-tert-pentyl-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 108° C., back pressure: $1.0 \times 10^2$ Pa), whereby di-tert-butyloxo(N,N'-di-tert-pentyl-1,2-vinylenediamide-$\kappa^2$N,N')hafnium (Hf($^t$PeNCH=CHN$^t$Pe)(O$^t$Bu)$_2$) was obtained as a yellow viscous liquid. Yield: 10.83 g (percentage yield: 48%).

$^1$H NMR (500 MHz, C$_6$D$_6$) δ 5.65 (s, 2H), 1.59 (q, J=7.3 Hz, 4H), 1.29 (s, 18H), 1.28 (s, 12H), 0.89 (t, J=7.3 Hz, 6H). $^{13}$C NMR (125 MHz, C$_6$D$_6$) δ 102.9, 76.0, 57.1, 36.3, 33.4, 29.6, 9.1.

Example-96

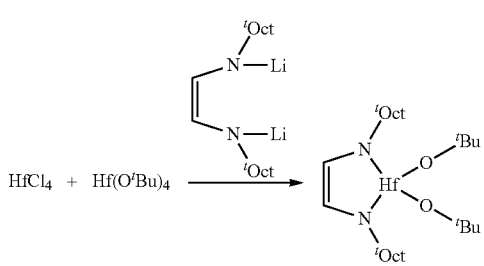

6.56 g (23.4 mmol) of N,N'-bis(1,1,3,3-tetramethylbutyl)-1,4-diaza-1,3-butadiene was dissolved in 50 mL of tetrahydrofuran, and 334 mg (48.1 mmol) of lithium was added. After stirring at room temperature for 15 hours, the solvent was removed under reduced pressure, and the remaining solid was dissolved in 50 mL of toluene to prepare a toluene solution of (N,N'-bis(1,1,3,3-tetramethylbutyl)-1,2-vinylenediamide)dilithium. On the other hand, 3.74 g (11.7 mmol) of hafnium tetrachloride was suspended in a mixed solvent of 30 mL of diethyl ether and 10 mL of tetrahydrofuran, and 5.50 g (11.7 mmol) of tetra(tert-butoxo)hafnium was added. After stirring at room temperature for 14 hours, the solvent was removed under reduced pressure from the reaction solution, and 50 mL of toluene was added. The solution was cooled to −70° C. by using a dry ice-methanol bath, and the toluene solution of (N,N'-bis(1,1,3,3-tetramethylbutyl)-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 90 mL of hexane. The hexane was removed under reduced pressure from the liquid extract, and the residue was distilled under reduced pressure (distillation temperature: 146° C., back pressure: $2.0 \times 10^2$ Pa), whereby di-tert-butyloxo(N,N'-bis(1,1,3,3-tetramethylbutyl)-1,2-vinylenediamide-$\kappa^2$N,N')hafnium(Hf($^t$OctNCH=CHN$^t$Oct)(O$^t$Bu)$_2$) was obtained as a yellow viscous liquid. Yield: 7.43 g (percentage yield: 52%).

$^1$H NMR (500 MHz, C$_6$D$_6$) δ 5.68 (s, 2H), 1.65 (s, 4H), 1.42 (s, 12H), 1.30 (s, 18H), 1.01 (s, 18H). $^{13}$C NMR (125 MHz, C$_6$D$_6$) δ 102.6, 76.0, 58.5, 56.4, 33.5, 32.2, 31.9, 31.8.

Example-97

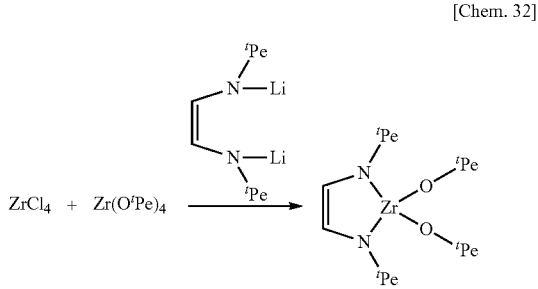

8.51 g (43.3 mmol) of N,N-di-tert-pentyl-1,4-diaza-1,3-butadiene was dissolved in 80 mL of tetrahydrofuran, and 617 mg (88.9 mmol) of lithium was added. After stirring at room temperature for 14 hours, the solvent was removed under reduced pressure, and the remaining solid was dissolved in 50 mL of toluene to prepare a toluene solution of (N,N'-di-tert-pentyl-1,2-vinylenediamide)dilithium. On the other hand, 5.05 g (21.7 mmol) of zirconium tetrachloride was suspended in a mixed solvent of 50 mL of diethyl ether and 20 mL of tetrahydrofuran, and 9.53 g (21.7 mmol) of tetra(tert-pentyloxo)zirconium was added. After stirring at room temperature for 14 hours, the solvent was removed under reduced pressure from the reaction solution, and 80 mL of toluene was added. The solution was cooled to −70° C. by using a dry ice-methanol bath, and the toluene solution of (N,N'-di-tert-pentyl-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 130° C., back pressure: 2.4×10² Pa), whereby di-tert-pentyloxo(N,N'-di-tert-pentyl-1,2-vinylenediamide-κ²N,N')zirconium(Zr($^t$PeNCH=CHN$^t$Pe)(O$^t$Pe)$_2$) was obtained as a yellow viscous liquid. Yield: 15.3 g (percentage yield: 76%).

$^1$H NMR (500 MHz, C$_6$D$_6$) δ 5.64 (s, 2H), 1.59 (q, J=7.3 Hz, 4H), 1.49 (br, q, J=7.3 Hz, 4H), 1.28 (s, 12H), 1.22 (br, s, 12H), 0.99 (br, t, J=7.3 Hz, 6H), 0.86 (t, J=7.3 Hz, 6H). $^{13}$C NMR (125 MHz, C$_6$D$_6$) δ 103.8, 77.7, 57.5, 38.0, 36.3, 31.1, 29.4, 9.3, 9.2.

Example-98

[Chem. 33]

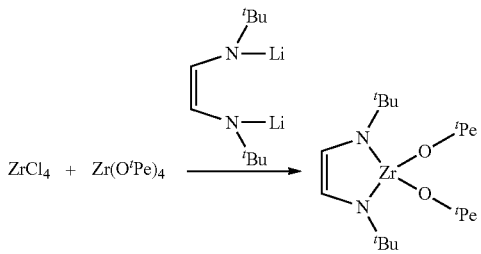

4.17 g (24.8 mmol) of N,N'-di-tert-butyl-1,4-diaza-1,3-butadiene was dissolved in 35 mL of tetrahydrofuran, and 352 mg (50.7 mmol) of lithium was added. After stirring at room temperature for 14 hours, the solvent was removed under reduced pressure, and the remaining solid was dissolved in 30 mL of toluene to prepare a toluene solution of (N,N'-di-tert-butyl-1,2-vinylenediamide)dilithium. On the other hand, 2.88 g (12.4 mmol) of zirconium tetrachloride was suspended in a mixed solvent of 35 mL of diethyl ether and 15 mL of tetrahydrofuran, and 5.44 g (12.4 mmol) of tetra(tert-pentyloxo)zirconium was added. After stirring at room temperature for 10 hours, the solvent was removed under reduced pressure from the reaction solution, and 40 mL of toluene was added. The solution was cooled to −70° C. by using a dry ice-methanol bath, and the toluene solution of (N,N'-di-tert-butyl-1,2-vinylenediamide)dilithium was added dropwise. After the completion of dropwise addition, the dry ice-methanol bath was removed, and the system was stirred at room temperature for 12 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 101° C., back pressure: 9.9×10¹ Pa), whereby (N,N'-di-tert-butyl-1,2-vinylenediamide-κ²N,N')bis(tert-pentyloxo)zirconium(Zr($^t$BuNCH=CHN$^t$Bu)(O$^t$Pe)$_2$) was obtained as a yellow liquid. Yield: 8.40 g (percentage yield: 78%).

$^1$H NMR (500 MHz, C$_6$D$_6$) δ 5.72 (s, 2H), 1.48 (q, J=7.3 Hz, 4H), 1.33 (s, 18H), 1.22 (s, 12H), 0.99 (t, J=7.3 Hz, 6H). $^{13}$C NMR (125 MHz, C$_6$D$_6$) δ 103.8, 77.7, 55.0, 38.0, 31.8, 31.1, 9.4.

Example-99

[Chem. 34]

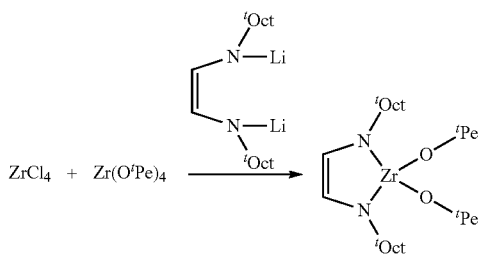

10.9 g (38.9 mmol) of N,N-bis(1,1,3,3-tetramethylbutyl)-1,4-diaza-1,3-butadiene was dissolved in 80 mL of tetrahydrofuran, and 553 mg (79.7 mmol) of lithium was added. After stirring at room temperature for 15 hours, the solvent was removed under reduced pressure, and the remaining solid was dissolved in 50 mL of toluene to prepare a toluene solution of (N,N'-bis(1,1,3,3-tetramethylbutyl)-1,2-vinylenediamide)dilithium. On the other hand, 4.53 g (19.4 mmol) of zirconium tetrachloride was suspended in a mixed solvent of 50 mL of diethyl ether and 20 mL of tetrahydrofuran, and 8.55 g (19.4 mmol) of tetra(tert-pentyloxo)zirconium was added. After stirring at room temperature for 14 hours, the solvent was removed under reduced pressure from the reaction solution, and 50 mL of toluene was added. The solution was cooled to −70° C. by using a dry ice-methanol bath, and the toluene solution of (N,N'-bis(1,1,3,3-tetramethylbutyl)-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 154° C., back pressure: 1.6×10² Pa), whereby di-tert-pentyloxo(N,N'-bis(1,1,3,3-tetramethylbutyl)-1,2-vinylenediamide-κ²N,N')zirconium(Zr($^t$OctNCH=CHN$^t$Oct)(O$^t$Pe)$_2$) was obtained as a yellow viscous liquid. Yield: 10.6 g (percentage yield: 50%).

$^1$H NMR (500 MHz, C$_6$D$_6$) δ 5.69 (s, 2H), 1.64 (s, 4H), 1.49 (br, 4H), 1.43 (s, 12H), 1.24 (brs, 12H), 1.02 (br, 6H), 1.00 (s, 18H). $^{13}$C NMR (125 MHz, C$_6$D$_6$) δ 103.4, 77.8, 58.9, 56.5, 38.0, 32.0, 31.9, 31.8, 31.2, 9.4.

Example-100

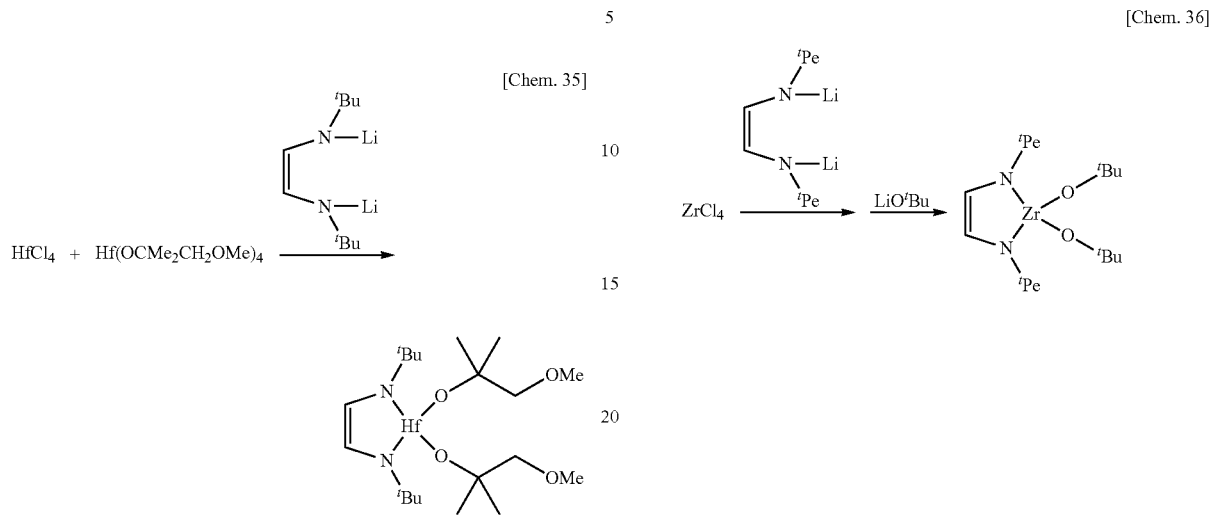

7.14 g (42.4 mmol) of N,N'-di-tert-butyl-1,4-diaza-1,3-butadiene was dissolved in 60 mL of tetrahydrofuran, and 600 mg (86.4 mmol) of lithium was added. After stirring at room temperature for 14 hours, the solvent was removed under reduced pressure, and the remaining solid was dissolved in 50 mL of toluene to prepare a toluene solution of (N,N'-di-tert-butyl-1,2-vinylenediamide)dilithium. On the other hand, 6.77 g (21.1 mmol) of hafnium tetrachloride was suspended in a mixed solvent of 50 mL of diethyl ether and 15 mL of tetrahydrofuran, and 12.5 g (21.1 mmol) of tetrakis(1,1-dimethyl-2-methoxyethyloxo)hafnium was added. After stirring at room temperature for 14 hours, the solvent was removed under reduced pressure from the reaction solution, and 80 mL of toluene was added. The solution was cooled to −70° C. by using a dry ice-methanol bath, and the toluene solution of (N,N'-di-tert-butyl-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 120 mL of hexane. The hexane was removed under reduced pressure from the liquid extract, and the residue was distilled under reduced pressure (distillation temperature: 135° C., back pressure: 1.2×10² Pa), whereby bis(1,1-dimethyl-2-methoxyethyloxo)(N,N'-di-tert-butyl-1,2-vinylenediamide-κ²N,N')hafnium(Hf($^t$BuNCH=CHN$^t$Bu)(OCMe$_2$CH$_2$OMe)$_2$) was obtained as a yellow viscous liquid. Yield: 12.2 g (percentage yield: 52%).

$^1$H NMR (500 MHz, C$_6$D$_6$) δ 5.79 (s, 2H), 3.26 (s, 6H), 3.08 (s, 4H), 1.41 (s, 18H), 1.21 (s, 12H). $^{13}$C NMR (125 MHz, C$_6$D$_6$) δ 105.5, 85.1, 75.1, 60.1, 55.3, 32.0, 29.8, 29.5.

Example-101

10.3 g (52.6 mmol) of N,N'-di-tert-pentyl-1,4-diaza-1,3-butadiene was dissolved in 80 mL of tetrahydrofuran, and after adding 748 mg (108 mmol) of lithium, the system was stirred at room temperature for 14 hours to prepare a tetrahydrofuran solution of (N,N'-di-tert-pentyl-1,2-vinylenediamide)dilithium. On the other hand, 12.3 g (52.6 mmol) of zirconium tetrachloride was suspended in a mixed solvent of 25 mL of diethyl ether and 50 mL of tetrahydrofuran, and after stirring at room temperature for 20 minutes, the solvent was removed under reduced pressure. By adding 50 mL of tetrahydrofuran to the residue, a tetrachlorobis(tetrahydrofuan)zirconium suspension was prepared. The tetrachlorobis(tetrahydrofuan)zirconium suspension was cooled to −70° C. by using a dry ice-methanol bath, and the tetrahydrofuran solution of (N,N'-di-tert-pentyl-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 120 mL of diethyl ether. The liquid extract was cooled to −70° C. by using a dry ice-methanol bath, and a hexane solution of tert-butoxylithium (2.69 mol/L, 40.0 mL, 107.6 mmol) was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 112° C., back pressure: 1.2×10² Pa), whereby di-tert-butyloxo(N,N'-di-tert-pentyl-1,2-vinylenediamide-κ²N,N')zirconium(Zr($^t$PeNCH=CHN$^t$Pe)(O$^t$Bu)$_2$) was obtained as a yellow viscous liquid. Yield: 7.78 g (percentage yield: 34%).

$^1$H NMR (500 MHz, C$_6$D$_6$) δ 5.64 (s, 2H), 1.57 (q, J=7.5 Hz, 4H), 1.28 (s, 30H), 0.86 (t, J=7.3 Hz, 6H). $^{13}$C NMR (125 MHz, C$_6$D$_6$) δ 103.7, 75.5, 57.4, 36.2, 33.4, 29.5, 9.2.

Example-102

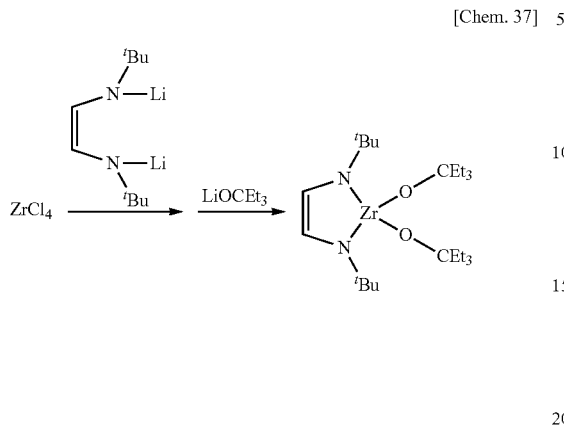

9.90 g (58.8 mmol) of N,N-di-tert-butyl-1,4-diaza-1,3-butadiene was dissolved in 80 mL of tetrahydrofuran, and after adding 836 mg (120 mmol) of lithium, the system was stirred at room temperature for 14 hours to prepare a tetrahydrofuran solution of (N,N'-di-tert-butyl-1,2-vinylenediamide)dilithium. On the other hand, 13.7 g (58.8 mmol) of zirconium tetrachloride was suspended in a mixed solvent of 25 mL of diethyl ether and 50 mL of tetrahydrofuran, and after stirring at room temperature for 20 minutes, the solvent was removed under reduced pressure. By adding 50 mL of tetrahydrofuran to the residue, a tetrachlorobis(tetrahydrofuan)zirconium suspension was prepared. The tetrachlorobis(tetrahydrofuan)zirconium suspension was cooled to −70° C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 13 hours. The solvent was removed under reduced pressure from the obtained slurry, and soluble components were extracted by adding 120 mL of diethyl ether. The liquid extract was cooled to −70° C. by using a dry ice-methanol bath, and a hexane solution of 1,1-diethylpropyloxylithium (2.69 mol/L, 43.7 mL, 118 mmol) was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 137° C., back pressure: $8.6 \times 10^1$ Pa), whereby (N,N'-di-tert-butyl-1,2-vinylenediamide-$\kappa^2$N,N')bis(1,1-diethylpropyloxo)zirconium(Zr($^t$BuNCH=CHN$^t$Bu)(OCEt$_3$)$_2$) was obtained as a yellow viscous liquid. Yield: 13.40 g (percentage yield: 47%).

$^1$H NMR (500 MHz, C$_6$D$_6$) δ 5.74 (s, 2H), 1.47 (q, J=7.3 Hz, 12H), 1.34 (s, 18H), 0.91 (t, J=7.3 Hz, 18H). $^{13}$C NMR (125 MHz, C$_6$D$_6$) δ 103.9, 82.2, 55.2, 32.4, 31.8, 8.7.

Example-103

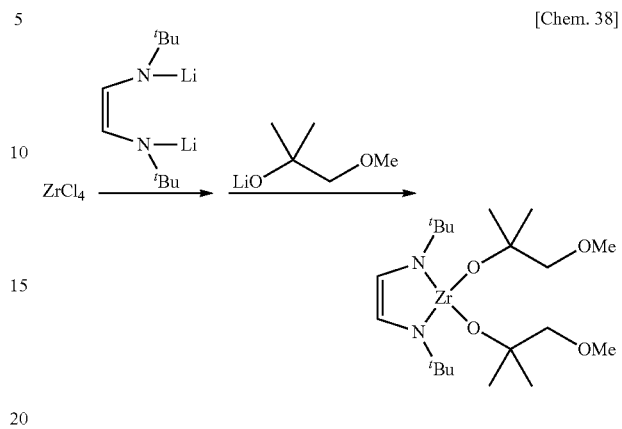

8.00 g (47.5 mmol) of N,N'-di-tert-butyl-1,4-diaza-1,3-butadiene was dissolved in 60 mL of tetrahydrofuran, and after adding 669 mg (96.4 mmol) of lithium, the system was stirred at room temperature for 14 hours to prepare a tetrahydrofuran solution of (N,N'-di-tert-butyl-1,2-vinylenediamide)dilithium. On the other hand, 11.0 g (47.2 mmol) of zirconium tetrachloride was suspended in a mixed solvent of 20 mL of diethyl ether and 40 mL of tetrahydrofuran, and after stirring at room temperature for 20 minutes, the solvent was removed under reduced pressure. By adding 40 mL of tetrahydrofuran to the residue, a tetrachlorobis(tetrahydrofuan)zirconium suspension was prepared. The tetrachlorobis(tetrahydrofuan)zirconium suspension was cooled to −70° C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 13 hours. The solvent was removed under reduced pressure from the obtained slurry, and soluble components were extracted by adding 110 mL of diethyl ether. The liquid extract was cooled to −70° C. by using a dry ice-methanol bath, and a hexane solution of 1,1-dimethyl-2-methoxyethyloxylithium (2.69 mol/L, 35.5 mL, 95.5 mmol) was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 118° C., back pressure: $9.6 \times 10^1$ Pa), whereby (N,N'-di-tert-butyl-1,2-vinylenediamide-$\kappa^2$N,N')bis(1,1-dimethyl-2-methoxyethyloxo)zirconium(Zr($^t$BuNCH=CHN$^t$Bu)(OCMe$_2$CH$_2$OMe)$_2$) was obtained as a yellow-orange viscous liquid. Yield: 14.80 g (percentage yield: 67%).

$^1$H NMR (500 MHz, C$_6$D$_6$) δ 5.79 (s, 2H), 3.27 (s, 6H), 3.09 (brs, 4H), 1.40 (s, 18H), 1.18 (s, 12H). $^{13}$C NMR (125 MHz, C$_6$D$_6$) δ 105.7, 84.8, 74.7, 60.0, 55.2, 31.6, 29.5.

Example-104

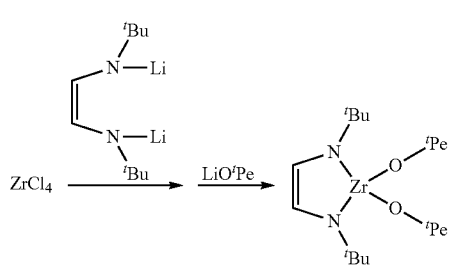

[Chem. 39]

7.60 g (45.2 mmol) of N,N'-di-tert-butyl-1,4-diaza-1,3-butadiene was dissolved in 60 mL of tetrahydrofuran, and after adding 642 mg (92.4 mmol) of lithium, the system was stirred at room temperature for 14 hours to prepare a tetrahydrofuran solution of (N,N'-di-tert-butyl-1,2-vinylenediamide)dilithium. On the other hand, 10.5 g (45.1 mmol) of zirconium tetrachloride was suspended in a mixed solvent of 20 mL of diethyl ether and 40 mL of tetrahydrofuran, and after stirring at room temperature for 20 minutes, the solvent was removed under reduced pressure. By adding 40 mL of tetrahydrofuran to the residue, a tetrachlorobis(tetrahydrofuan)zirconium suspension was prepared. The tetrachlorobis(tetrahydrofuan)zirconium suspension was cooled to $-70°$ C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of diethyl ether. The liquid extract was cooled to $-70°$ C. by using a dry ice-methanol bath, and a hexane solution of tert-pentyloxylithium (2.69 mol/L, 34.0 mL, 91.5 mmol) was added dropwise. After the completion of dropwise addition, the dry ice-methanol bath was removed, and the system was stirred at room temperature for 14 hours. The solvent was removed under reduced pressure from the obtained slurry, and soluble components were extracted by adding 100 mL of hexane. The hexane was removed under reduced pressure from the liquid extract, and the residue was distilled under reduced pressure (distillation temperature: 101° C., back pressure: $9.9×10^1$ Pa), whereby (N,N'-di-tert-butyl-1,2-vinylenediamide-$κ^2$N,N')bis(tert-pentyloxo)zirconium(Zr($^t$BuNCH=CHN$^t$Bu)(O$^t$Pe)$_2$) was obtained as a yellow liquid. Yield: 13.77 g (percentage yield: 70%).

$^1$H NMR (500 MHz, C$_6$D$_6$) δ 5.72 (s, 2H), 1.48 (q, Hz, 4H), 1.33 (s, 18H), 1.22 (s, 12H), 0.99 (t, J=7.3 Hz, 6H). $^{13}$C NMR (125 MHz, C$_6$D$_6$) δ 103.8, 77.7, 55.0, 38.0, 31.8, 31.1, 9.4.

Example-105

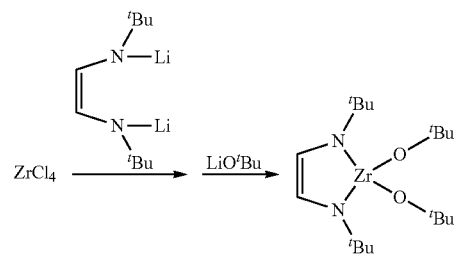

[Chem. 40]

4.91 g (29.2 mmol) of N,N-di-tert-butyl-1,4-diaza-1,3-butadiene was dissolved in 100 mL of tetrahydrofuran, and after adding 425 mg (61.2 mmol) of lithium, the system was stirred at room temperature for 14 hours to prepare a tetrahydrofuran solution of (N,N'-di-tert-butyl-1,2-vinylenediamide)dilithium. On the other hand, 6.80 g (29.2 mmol) of zirconium tetrachloride was suspended in a mixed solvent of 40 mL of hexane and 10 mL of tetrahydrofuran, and after stirring at room temperature for 1 hour, the solvent was removed under reduced pressure. By adding 150 mL of tetrahydrofuran to the residue, a tetrachlorobis(tetrahydrofuan) zirconium suspension was prepared. The tetrachlorobis(tetrahydrofuan)zirconium suspension was cooled to $-70°$ C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 24 hours. The solvent was removed under reduced pressure from the obtained slurry, and soluble components were extracted by adding 150 mL of diethyl ether. The liquid extract was cooled to $-70°$ C. by using a dry ice-methanol bath, and a hexane solution of tert-butoxylithium (2.69 mol/L, 21.7 mL, 58.4 mmol) was added dropwise. After the completion of dropwise addition, the dry ice-methanol bath was removed, and the system was stirred at room temperature for 2 hours. The solvent was removed under reduced pressure from the obtained slurry, and soluble components were extracted by adding 110 mL of hexane. The hexane was removed under reduced pressure from the liquid extract, and the residue was sublimated under reduced pressure, whereby (N,N'-di-tert-butyl-1,2-vinylenediamide-$κ^2$N, N')bis(tert-butoxo)zirconium(Zr($^t$BuNCH=CHN$^t$Bu)(O$^t$Bu)$_2$) was obtained as a yellow solid. Yield: 4.15 g (percentage yield: 35%).

$^1$H NMR (500 MHz, C$_6$D$_6$) δ 5.73 (s, 2H), 1.33 (s, 18H), 1.28 (s, 18H). $^{13}$C NMR (125 MHz, C$_6$D$_6$) δ 103.7, 75.4, 54.8, 33.4, 31.8.

Example-106

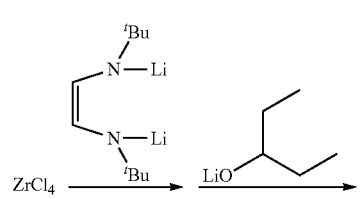

[Chem. 41]

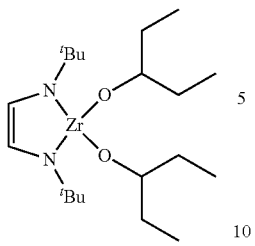

2.30 g (13.7 mmol) of N,N'-di-tert-butyl-1,4-diaza-1,3-butadiene was dissolved in 40 mL of tetrahydrofuran, and after adding 199 mg (28.7 mmol) of lithium, the system was stirred at room temperature for 18 hours to prepare a tetrahydrofuran solution of (N,N'-di-tert-butyl-1,2-vinylenediamide)dilithium. On the other hand, 4.44 g (19.1 mmol) of zirconium tetrachloride was suspended in a mixed solvent of 50 mL of hexane and 200 mL of tetrahydrofuran, and by stirring at room temperature for 30 minutes, a tetrachlorobis(tetrahydrofuan)zirconium suspension was prepared. The tetrachlorobis(tetrahydrofuan)zirconium suspension was cooled to −70° C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 25 hours. The solvent was removed under reduced pressure from the obtained slurry, and soluble components were extracted by adding 100 mL of diethyl ether. The liquid extract was cooled to −70° C. by using a dry ice-methanol bath, and a reaction solution obtained by adding a hexane solution of 1-ethylpropyloxylithium (2.69 mol/L, 10.2 mL, 27.4 mmol) and stirring the solution for 15 hours was added dropwise. After the completion of dropwise addition, the dry ice-methanol bath was removed, and the system was stirred at room temperature for 9 hours. The solvent was removed under reduced pressure from the obtained slurry, and soluble components were extracted by adding 50 mL of hexane. The hexane was removed under reduced pressure from the liquid extract, and the residue was distilled under reduced pressure (distillation temperature: 110° C., back pressure: $1.0 \times 10^2$ Pa), whereby (N,N'-di-tert-butyl-1,2-vinylenediamide-$\kappa^2$N,N')bis(1-ethylpropyloxo)zirconium (Zr($^t$BuNCH=CHN$^t$Bu)(OCHEt$_2$)$_2$) was obtained as a yellow-orange viscous liquid. Yield: 2.06 g (percentage yield: 35%).

$^1$H NMR (500 MHz, C$_6$D$_6$) δ 5.71 (s, 2H), 4.12 (quintet, J=6.0 Hz, 2H), 1.75 (m, 8H), 1.24 (s, 18H), 1.10 (t, J=7.3 Hz, 12H). $^{13}$C NMR (125 MHz, C$_6$D$_6$) δ 103.7, 82.8, 55.2, 31.6, 30.8, 11.1.

Example-107

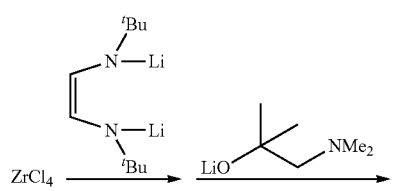

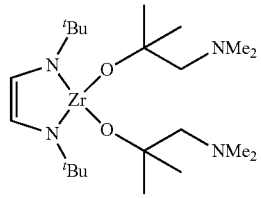

4.86 g (28.9 mmol) of N,N'-di-tert-butyl-1,4-diaza-1,3-butadiene was dissolved in 40 mL of tetrahydrofuran, and after adding 420 mg (60.5 mmol) of lithium, the system was stirred at room temperature for 14 hours to prepare a tetrahydrofuran solution of (N,N'-di-tert-butyl-1,2-vinylenediamide)dilithium. On the other hand, 6.73 g (28.9 mmol) of zirconium tetrachloride was suspended in a mixed solvent of 40 mL of hexane and 10 mL of tetrahydrofuran, and after stirring at room temperature for 1 hour, the solvent was removed under reduced pressure. By adding 150 mL of tetrahydrofuran to the residue, a tetrachlorobis(tetrahydrofuan) zirconium suspension was prepared. The tetrachlorobis(tetrahydrofuan)zirconium suspension was cooled to −70° C. by using a dry ice-methanol bath, and the tetrahydrofuran solution of (N,N'-di-tert-butyl-1,2-vinylenediamide)dilithium was added dropwise. After the completion of dropwise addition, the dry ice-methanol bath was removed, and the system was stirred at room temperature for 24 hours. The solvent was removed under reduced pressure from the obtained slurry, and soluble components were extracted by adding 150 mL of diethyl ether. The solvent was removed under reduced pressure from the liquid extract, and 100 mL of hexane was added to the residue to prepare a suspension. This suspension was cooled to −70° C. by using a dry ice-methanol bath, and a hexane solution of 1,1-dimethyl-2-dimethylaminoethyloxylithium (2.69 mol/L, 21.5 mL, 57.8 mmol) was added dropwise. After the completion of dropwise addition, the dry ice-methanol bath was removed, and the system was stirred at room temperature for 16 hours. The slurry obtained was filtered, and after removing the solvent under reduced pressure from the filtrate, the residue was distilled under reduced pressure (distillation temperature: 111° C., back pressure: 9.8× $10^1$ Pa), whereby (N,N'-di-tert-butyl-1,2-vinylenediamide-$\kappa^2$N,N')bis(1,1-dimethyl-2-dimethylaminoethyloxy) zirconium (Zr($^t$BuNCH=CHN$^t$Bu)(OCMe$_2$CH$_2$NMe$_2$)$_2$) was obtained as a yellow-orange liquid. Yield: 5.85 g (percentage yield: 41%).

$^1$H NMR (500 MHz, C$_6$D$_6$) δ 5.80 (s, 2H), 2.27 (s, 4H), 2.25 (s, 12H), 1.44 (s, 18H), 1.29 (s, 12H). $^{13}$C NMR (125 MHz, C$_6$D$_6$) δ 106.0, 73.6, 73.3, 55.1, 49.0, 31.7, 31.1.

Example-108

[Chem. 42]

ZrCl$_4$ 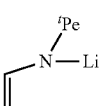

[Chem. 43]

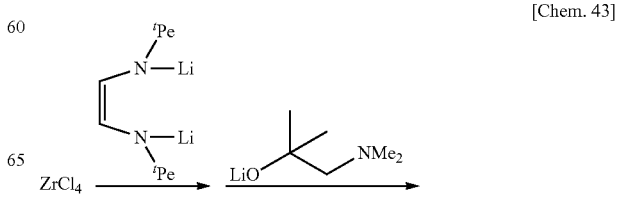

-continued

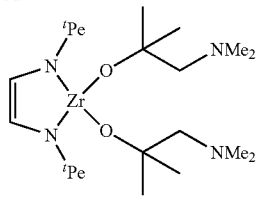

8.08 g (41.2 mmol) of N,N'-di-tert-pentyl-1,4-diaza-1,3-butadiene was dissolved in 80 mL of tetrahydrofuran, and after adding 606 mg (87.3 mmol) of lithium, the system was stirred at room temperature for 15 hours to prepare a tetrahydrofuran solution of (N,N'-di-tert-pentyl-1,2-vinylenediamide)dilithium. On the other hand, 9.59 g (41.2 mmol) of zirconium tetrachloride was suspended in a mixed solvent of 100 mL of hexane and 50 mL of tetrahydrofuran, and by stirring at room temperature for 40 minutes, a tetrachlorobis(tetrahydrofuan)zirconium suspension was prepared. The tetrachlorobis(tetrahydrofuan)zirconium suspension was cooled to −70° C. by using a dry ice-methanol bath, and the tetrahydrofuran solution of (N,N'-di-tert-pentyl-1,2-vinylenediamide)dilithium was added dropwise. After the completion of dropwise addition, the dry ice-methanol bath was removed, and the system was stirred at room temperature for 24 hours. The solvent was removed under reduced pressure from the obtained slurry, and soluble components were extracted by adding 100 mL of diethyl ether. The solvent was removed under reduced pressure from the liquid extract, and 100 mL of hexane was added to the obtained residue to prepare a suspension. This suspension was cooled to −70° C. by using a dry ice-methanol bath, and a hexane solution of 1,1-dimethyl-2-dimethylaminoethyloxylithium (2.69 mol/L, 30.6 mL, 82.3 mmol) was added dropwise. After the completion of dropwise addition, the dry ice-methanol bath was removed, and the system was stirred at room temperature for 15 hours. The slurry obtained was filtered, and after removing the solvent under reduced pressure from the filtrate, the residue was distilled under reduced pressure (distillation temperature: 127° C., back pressure: $4.3 \times 10^1$ Pa), whereby (N,N'-di-tert-pentyl-1,2-vinylenediamide-$\kappa^2$N,N')bis(1-dimethylamino-2-methyl-2-propyloxy)zirconium(Zr($^t$PeNCH=CHN$^t$Pe)(OCMe$_2$CH$_2$NMe$_2$)$_2$) was obtained as a yellow-orange liquid. Yield: 6.92 g (percentage yield: 32%).
$^1$H NMR (500 MHz, C$_6$D$_6$) δ 5.73 (s, 2H), 2.29 (s, 4H), 2.26 (s, 12H), 1.66 (t, J=7.3 Hz, 4H), 1.42 (s, 12H), 1.29 (s, 12H), 0.93 (t, J=7.3 Hz, 6H). $^{13}$C NMR (125 MHz, C$_6$D$_6$) δ105.7, 73.7, 73.3, 57.7, 49.0, 37.3, 31.5, 28.2, 9.3.

Example-109

In an argon atmosphere, 0.5 g of a mixture of Zr($^t$PeNCH=CHN$^t$Pe)(O$^t$Bu)$_2$ obtained in Example-101 and tetra(tert-butoxy)zirconium(molar ratio: 26:74) and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 24 hours while keeping the connection of the balloon to the Schlenk tube, the inside of the Schlenk was depressurized to 10 Pa under heating at 80° C., and volatile components were thereby remove to obtain 0.28 g of a yellow solid. This yellow solid was dissolved in 3 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 0.25 g of Film-forming Material 10 as a black-brown solid. Film-Forming Material 10 (0.25 g) was dissolved in 3.0 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Zr-01 was obtained.

Also, 0.27 g of a yellow solid obtained in the same manner as above was transferred to a Schlenk tube, and the yellow solid was dissolved in 0.6 ml of diethyl ether. After immersing the Schlenk tube in an ice bath for 3 hours, the Schlenk tube is frozen at −30° C. to obtain a white needle-like crystal. Incidentally, the single-crystal X-ray structural analysis revealed that the needle-like crystal is Zr$_3$O(OH)($^t$Bu)$_9$ having 3 zirconium atoms which are bridged by a bridging oxygen atom.
(X-Ray Crystal Analysis)

The final R value in the structural analysis and refinement was 0.06. The final Rw value was 0.13.
Compositional formula: $C_{36}H_{82}O_{11}Zr_3$
Crystal system: monoclinic
Space group: P21/m
Lattice constant: a=10.84 Å, b=20.55 Å, c=11.31 Å, α=γ=90°, β=101°

Example-110

In an argon atmosphere, 6.6 g of a mixture of Zr($^t$PeNCH=CHN$^t$Pe)(O$^t$Pe)$_2$ obtained in Example-97 and tetra(tert-pentoxy)zirconium(molar ratio: 67:33) and a magnetic stirrer were put in a 50-mL Schlenk tube, and the inside of the Schlenk tube was depressurized to 2 Pa. A balloon having an internal volume of 5 L and being filled with a mixed gas of oxygen and argon (oxygen: 20 vol %) was connected to the Schlenk tube, and the inside of the Schlenk tube was filled with the mixed gas of oxygen and argon. After stirring at room temperature for 240 hours while keeping the connection of the balloon to the Schlenk tube, the inside of the Schlenk was depressurized to 10 Pa under heating at 80° C., and volatile components were thereby remove to obtain 4.1 g of a brown liquid. This brown liquid was dissolved in 30 mL of ethylene glycol monomethyl ether in an argon atmosphere, and the resulting solution was heated at 80° C. for 15 hours and further evaporated to dryness over 10 hours under reducing the pressure inside the reaction vessel to 10 Pa at 80° C. to obtain 1.8 g of Film-forming Material 11 as a black solid. Film-Forming Material 11 (0.24 g) was dissolved in 2.2 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Zr-02 was obtained.

Film-Forming Material Solution Zr-03 was obtained in the same manner by dissolving 0.51 g of Film-Forming Material 11 in 2.7 mL of ethylene glycol monomethyl ether in an argon atmosphere, and passing the resulting solution through a syringe filter (SLLGM25NS, manufactured by Millpore, pore size: 0.20 μm) to remove insoluble matters by filtration.

Example-111

In an argon atmosphere, 8.0 g of Zr($^t$PeNCH=CHN$^t$Pe)(O$^t$Bu)$_2$ obtained in Example-101, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 9 hours, the flowing of gas was stopped, and the toluene solution was cooled to room temperature. The toluene was removed under reduced pressure, and 20 mL of acetonitrile was added to the residue. Insoluble matters were collected by filtration, and the insoluble matters collected were dried under reduced pressure to obtain 5.6 g of a yellow solid. The obtained yellow solid (0.3 g) was dissolved in 1.7 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 0.24 g of Film-forming Material 12 as an orange solid. Film-Forming Material 12 (0.24 g) was dissolved in 1.0 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Zr-04 was obtained.

Example-112

In an argon atmosphere, 5.0 g of $Zr(^tBuNCH=CHN^tBu)(OCEt_3)_2$ obtained in Example-102, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 9 hours, the flowing of gas was stopped, and the toluene solution was cooled to room temperature. The toluene was removed under reduced pressure, and 80 mL of acetonitrile was added to the residue. Insoluble matters were collected by filtration, and the insoluble matters collected were dried under reduced pressure to obtain 2.5 g of a yellow solid. The obtained yellow solid (0.6 g) was dissolved in 4.1 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 0.31 g of Film-forming Material 13 as a yellow-brown solid. Film-Forming Material 13 (0.31 g) was dissolved in 2.6 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Zr-05 was obtained.

Example-113

In an argon atmosphere, 8.0 g of $Zr(^tBuNCH=CHN^tBu)(O^tPe)_2$ obtained in Example-98, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 6 hours, the flowing of gas was stopped, and the toluene solution was cooled to room temperature. The toluene was removed under reduced pressure, and 2 mL of toluene and 40 mL of acetonitrile were added to the residue. Insoluble matters were collected by filtration, and the insoluble matters collected were dried under reduced pressure to obtain 5.3 g of an orange viscous solid. The obtained orange viscous solid (0.6 g) was dissolved in 3.4 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 0.34 g of Film-forming Material 14 as an orange solid. Film-Forming Material 14 (0.34 g) was dissolved in 2.6 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Zr-06 was obtained.

Comparative Example-5

In an argon atmosphere, 5.0 g of tetra-tert-butoxyzirconium, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 6 hours, the flowing of gas was stopped, and the toluene solution was cooled to room temperature. The toluene was removed under reduced pressure to obtain 2.4 g of a residue, and 0.6 g of the residue was weighed and dissolved in 3.2 mL of ethylene glycol monomethyl ether. The resulting solution was heated at 80° C. for 18 hours and further concentrated over 10 hours under reducing the pressure inside the reaction vessel to 10 Pa at 22° C. to obtain 0.58 g of Film-forming Material 15 as a white viscous liquid. Film-Forming Material 15 (0.58 g) was dissolved in 2.6 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Zr-07 was obtained.

Example-114

In an argon atmosphere, 8.0 g of $Hf(^tPeNCH=CHN^tPe)(O^tBu)_2$ obtained in Example-95, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 10 hours, the flowing of gas was stopped, and the toluene solution was cooled to room temperature. The toluene was removed under reduced pressure, and 1 mL of toluene and 40 mL of acetonitrile were added to the residue. Insoluble matters were collected by filtration, and the insoluble matters collected were dried under reduced pressure to obtain 4.8 g of a yellow solid. The obtained yellow solid (0.6 g) was dissolved in 2.7 mL of ethylene glycol monomethyl ether in an argon atmosphere, and the resulting solution was heated at 80° C. for 18 hours and further evaporated to dryness over 10 hours under reducing the pressure inside the reaction vessel to 10 Pa at 22° C. to obtain 0.42 g of Film-forming Material 16 as a red-brown solid. Film-Forming Material 16 (0.42 g) was dissolved in 3.4 mL of ethylene glycol monomethyl ether in an argon atmosphere and passed through a syringe filter (SLLGM25NS, manufactured by Millipore, pore size: 0.20 µm) to remove insoluble matters by filtration, whereby Film-Forming Material Solution Hf-01 was obtained.

Comparative Example-6

In an argon atmosphere, 8.0 g of tetra-tert-butoxyhafnium, 20 mL of toluene and a magnetic stirrer were put in a 50-mL Schlenk tube to prepare a toluene solution of vinylenediamide complex, and a mixed gas of argon (oxygen: 20 vol %) was flowed at a flow rate of 100 mL/min to the toluene solution through a Teflon (registered trademark) tube with stirring. After 6 hours, the flowing of gas was stopped, and the toluene solution was cooled to room temperature. The toluene was removed under reduced pressure to obtain 4.8 g of a residue, and 0.6 g of the residue was weighed and dissolved in 2.7 mL of ethylene glycol monomethyl ether. The resulting solution was heated at 80° C. for 18 hours and further concentrated over 10 hours under reducing the pressure inside the reaction vessel to 10 Pa at 22° C. to obtain 0.42 g of Film-forming Material 17 as a white liquid. Film-Forming Material 17 (0.42 g) was dissolved in 3.4 mL of ethylene glycol monomethyl ether in an argon atmosphere and passed through a syringe filter (SLLGM25NS, manufactured by Millipore, pore size: 0.20 μm) to remove insoluble matters by filtration, whereby Film-Forming Material Solution Hf-02 was obtained.

Example-115 to Example-135 and Comparative Example-7 to Comparative Example-11

Each of the film-forming material solutions produced by the methods described in Example-109 to Example-114, Comparative Example-5 and Comparative Example-6 was coated on a surface of Corning 1737 glass substrate by spin coating method, and the substrate was heat-treated for 30 minutes to produce an oxide film. Evaluation results of the obtained metal oxide films are shown in Table 14. Incidentally, as for the rotation condition in the spin coating method, the substrate was processed at a rotation speed of 500 rpm for 10 seconds and then processed at 2,000 rpm for 30 seconds. The film thickness and refractive index were determined by performing multilayer film analysis of the spectrum at a wavelength of 300 to 800 nm measured by means of an ellipsometer (MEL-30S, manufactured by JASCO Corporation).

Test Example-9

An oxide film obtained by coating Film-Forming Material Solution Zr-03 on a surface of a substrate by spin coating method and heat-treating the substrate was subjected to a plasma resistance test. A Kapton tape was attached to the central part on the substrate surface to serve as a mask, and plasma etching of this substrate was performed at an output of 300 W for 2 minutes while flowing a mixed gas of $CF_4$ (flow rate: 25.2 sccm)-$O_2$ (flow rate: 6.34 sccm)-Ar (flow rate: 126 sccm) by using a parallel plate reactive ion etching apparatus (DEM-451, manufactured by ANELVA). After the plasma etching, the Kapton tape was peeled off, and the step generated at the interface between the Kapton tape-attached part and the non-attached part was measured at three portions in the same sample by using a contact surface roughness meter (DEKTAK3030, manufactured by Sloan). The average value thereof was taken as the plasma etching amount, and a value obtained by dividing the plasma etching amount by the etching time was taken as the plasma etching speed. Incidentally, when plasma etching was performed under the same conditions, the plasma etching speed of quartz glass used as the substrate was 60.0 nm/min. The results of this test are shown in Table 15. As for the rotation condition in the spin coating method, the substrate was processed at a rotation speed of 500 rpm for 15 seconds and then processed at 1,000 rpm for 30 seconds.

Test Example-10

An oxide film obtained by coating Film-Forming Material Solution Zr-03 on a surface of a substrate by spin coating method and heat-treating the substrate for 0.5 hours was subjected to a hydrofluoric acid solution resistance test. A Kapton tape was attached to the central part on the substrate surface to serve as a mask, and this substrate was dipped in an aqueous 0.5 wt % hydrofluoric acid solution at 20° C., thereby performing wet etching. After the etching for a predetermined time, the Kapton tape was peeled off, and the step generated at the interface between the Kapton tape-attached part and the non-attached part was measured at three portions in the same sample by using a contact surface roughness meter (DEKTAK3030, manufactured by Sloan). The average value thereof was taken as the wet etching amount, and a value obtained by dividing the wet etching amount by the etching time was taken as the wet etching speed. Incidentally, when wet etching was performed under the same conditions, the wet etching speed of quartz glass used as the substrate was 1.5 nm/min. The results of this test are shown in Table 16. As for the rotation condition in the spin coating method, the substrate was processed at a rotation speed of 500 rpm for 15 seconds and then processed at 5,000 rpm for 60 seconds.

TABLE 14

| Example | Sample | Heat Treatment Temperature | Film Thickness (nm) | Refractive Index |
|---|---|---|---|---|
| Example-115 | Zr-01 | 120° C. | 105 | 1.64 |
| Example-116 | ↑ | 200° C. | 88 | 1.67 |
| Example-117 | ↑ | 400° C. | 53 | 1.81 |
| Example-118 | Zr-02 | 120° C. | 89 | 1.67 |
| Example-119 | ↑ | 200° C. | 75 | 1.69 |
| Example-120 | ↑ | 400° C. | 44 | 1.86 |
| Example-121 | ↑ | 700° C. | 41 | 1.86 |
| Example-122 | Zr-04 | 120° C. | 185 | 1.74 |
| Example-123 | ↑ | 200° C. | 153 | 1.77 |
| Example-124 | ↑ | 400° C. | 107 | 1.91 |
| Example-125 | ↑ | 700° C. | 97 | 1.90 |
| Example-126 | Zr-05 | 120° C. | 209 | 1.52 |
| Example-127 | ↑ | 200° C. | 188 | 1.74 |
| Example-128 | ↑ | 400° C. | 119 | 1.82 |
| Example-129 | ↑ | 700° C. | 118 | 1.81 |
| Example-130 | Zr-06 | 120° C. | 191 | 1.55 |
| Example-131 | ↑ | 200° C. | 106 | 1.66 |
| Example-132 | ↑ | 400° C. | 63 | 1.60 |
| Example-133 | ↑ | 700° C. | 74 | 1.51 |
| Comparative Example-7 | Zr-07 | 200° C. | 174 | 1.59 |
| Comparative Example-8 | ↑ | 400° C. | 156 | 1.66 |
| Comparative Example-9 | ↑ | 700° C. | 150 | 1.55 |
| Example-134 | Hf-01 | 400° C. | 152 | 1.60 |
| Example-135 | ↑ | 700° C. | 124 | 1.57 |
| Comparative Example-10 | Hf-02 | 400° C. | 194 | 1.46 |
| Comparative Example-11 | ↑ | 700° C. | 156 | 1.45 |

TABLE 15

| Film-Forming Material Solution | Substrate | Heat Treatment Temperature | Heat Treatment Time | Etching Speed (nm/min) |
|---|---|---|---|---|
| Zr-03 | quartz glass | 300° C. | 0.5 h | 9.7 |
| Zr-03 | quartz glass | 500° C. | 0.5 h | 9.5 |

TABLE 15-continued

| Film-Forming Material Solution | Substrate | Heat Treatment Temperature | Heat Treatment Time | Etching Speed (nm/min) |
|---|---|---|---|---|
| Zr-03 | quartz glass | 700° C. | 0.5 h | 5.9 |
| Zr-03 | quartz glass | 1000° C. | 0.5 h | 5.4 |
| Zr-03 | Si wafer | 300° C. | 0.5 h | 16.5 |
| Zr-03 | Si wafer | 500° C. | 0.5 h | 10.0 |
| Zr-03 | Si wafer | 700° C. | 0.5 h | 14.7 |
| Zr-03 | Si wafer | 1000° C. | 0.5 h | 11.4 |

TABLE 16

| Film-Forming Material Solution | Substrate | Heat Treatment Temperature | Heat Treatment Time | Etching Amount | Etching Speed |
|---|---|---|---|---|---|
| Zr-03 | quartz glass | 300° C. | 40 sec | 130 nm | 200 nm/min |
| Zr-03 | quartz glass | 500° C. | 42 min | <10 nm | <0.3 nm/min |
| Zr-03 | quartz glass | 700° C. | 40 min | <10 nm | <0.3 nm/min |

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2011-192739) filed on Sep. 5, 2011, Japanese Patent Application (Patent Application No. 2011-192740) filed on Sep. 5, 2011, Japanese Patent Application (Patent Application No. 2011-218284) filed on Sep. 30, 2011, Japanese Patent Application (Patent Application No. 2012-026203) filed on Feb. 9, 2012, and Japanese Patent Application (Patent Application No. 2012-058232) filed on Mar. 15, 2012, the contents of which are incorporated herein by way of reference.

INDUSTRIAL APPLICABILITY

By virtue of using a film-forming material produced by reacting a vinylenediamide complex (1) or (2) with one or more kinds of oxidizing agents selected from the group consisting oxygen gas, air, ozone, water and hydrogen peroxide, a Group IV metal oxide film can be obtained even by heat treatment at a low temperature. Accordingly, the industrial value of the present invention is remarkable.

The invention claimed is:

1. A film-forming material, obtained by a process comprising:
    dissolving a compound comprising a titanium atom or a zirconium atom, with the titanium atom or the zirconium atom being bridged by a bridging oxygen atom, in an alcohol comprising two or more oxygen atoms, thereby obtaining a solution, and
    heating the solution.
2. The film-forming material according to claim 1, wherein the alcohol is a cellosolve.
3. The film-forming material according to claim 2, wherein the cellosolve is ethylene glycol monomethyl ether.

* * * * *